United States Patent
Patel et al.

(10) Patent No.: US 9,168,231 B2
(45) Date of Patent: Oct. 27, 2015

(54) FIBROUS POLYMER SCAFFOLDS HAVING DIAMETRICALLY PATTERNED POLYMER FIBERS

(75) Inventors: Shyam Patel, Oakland, CA (US); Kyle Kurpinski, San Leandro, CA (US)

(73) Assignee: NANONERVE, INC., Berkeley, CA (US)

( * ) Notice: Subject to any disclaimer, the term of this patent is extended or adjusted under 35 U.S.C. 154(b) by 250 days.

(21) Appl. No.: 13/988,491

(22) PCT Filed: Dec. 2, 2011

(86) PCT No.: PCT/US2011/063142
§ 371 (c)(1),
(2), (4) Date: Dec. 3, 2013

(87) PCT Pub. No.: WO2012/078472
PCT Pub. Date: Jun. 14, 2012

(65) Prior Publication Data
US 2014/0079759 A1    Mar. 20, 2014

Related U.S. Application Data

(60) Provisional application No. 61/419,869, filed on Dec. 5, 2010.

(51) Int. Cl.
| | |
|---|---|
| B29C 47/00 | (2006.01) |
| A61L 15/00 | (2006.01) |
| A61L 15/16 | (2006.01) |
| A61K 38/00 | (2006.01) |
| D01D 5/00 | (2006.01) |
| A61K 9/70 | (2006.01) |
| A61L 27/50 | (2006.01) |

(Continued)

(52) U.S. Cl.
CPC ............ *A61K 9/70* (2013.01); *A61K 31/765* (2013.01); *A61K 45/06* (2013.01); *A61L 27/50* (2013.01); *A61L 27/54* (2013.01); *D01D 5/0076* (2013.01); *D01F 1/10* (2013.01); *A61L 2300/64* (2013.01)

(58) Field of Classification Search
None
See application file for complete search history.

(56) References Cited

U.S. PATENT DOCUMENTS

| | | | |
|---|---|---|---|
| 4,323,525 | A | 4/1982 | Bornat |
| 4,968,590 | A | 11/1990 | Kuberasampath et al. |

(Continued)

FOREIGN PATENT DOCUMENTS

| | | |
|---|---|---|
| EP | 2045375 A1 | 4/2009 |
| WO | 02092667 A1 | 11/2002 |

(Continued)

OTHER PUBLICATIONS

Baker, et al., "The Potential to Improve Cell Infiltration in Composite Fiber-Aligned Electrospun Scaffolds by the Selective Removal of Sacrificial Fibers", Biomaterials, vol. 29, Issue 15, 2008, 2348-2358.

(Continued)

*Primary Examiner* — Jeffrey T Palenik
(74) *Attorney, Agent, or Firm* — Dorsey & Whitney LLP

(57) ABSTRACT

Fibrous polymer scaffolds having at least one layer of diametrically patterned fibers, as well as methods of manufacture, are provided. The scaffolds can be formed of multiple layers and the extent and direction of alignment of each layer can be controlled. Fabrication systems and methods for producing such scaffolds including apparatuses and processes are also provided.

14 Claims, 9 Drawing Sheets

(51) Int. Cl.
*A61L 27/54* (2006.01)
*D01F 1/10* (2006.01)
*A61K 31/765* (2006.01)
*A61K 45/06* (2006.01)

(56) References Cited

U.S. PATENT DOCUMENTS

| | | | |
|---|---|---|---|
| 4,975,526 | A | 12/1990 | Kuberasampath et al. |
| 5,011,691 | A | 4/1991 | Oppermann et al. |
| 5,013,649 | A | 5/1991 | Wang et al. |
| 5,108,753 | A | 4/1992 | Kuberasampath et al. |
| 5,162,114 | A | 11/1992 | Kuberasampath et al. |
| 5,166,058 | A | 11/1992 | Wang et al. |
| 5,171,574 | A | 12/1992 | Kuberasampath et al. |
| 5,258,494 | A | 11/1993 | Oppermann et al. |
| 5,266,683 | A | 11/1993 | Oppermann et al. |
| 5,324,819 | A | 6/1994 | Oppermann |
| 5,354,557 | A | 10/1994 | Oppermann et al. |
| 5,496,552 | A | 3/1996 | Kuberasampath et al. |
| 5,618,924 | A | 4/1997 | Wang et al. |
| 5,631,142 | A | 5/1997 | Wang et al. |
| 5,674,292 | A | 10/1997 | Tucker et al. |
| 5,750,651 | A | 5/1998 | Oppermann et al. |
| 5,840,325 | A | 11/1998 | Kuberasampath et al. |
| 5,861,034 | A | 1/1999 | Taira et al. |
| 5,863,758 | A | 1/1999 | Oppermann et al. |
| 5,958,441 | A | 9/1999 | Oppermann et al. |
| RE36,370 | E | 11/1999 | Li |
| 6,013,856 | A | 1/2000 | Tucker et al. |
| 6,028,242 | A | 2/2000 | Tucker et al. |
| 6,103,255 | A | 8/2000 | Levene et al. |
| 6,309,423 | B2 | 10/2001 | Hayes |
| 6,347,930 | B1 | 2/2002 | Muscat et al. |
| 6,616,435 | B2 | 9/2003 | Lee et al. |
| 6,673,285 | B2 | 1/2004 | Ma |
| 6,676,675 | B2 | 1/2004 | Mallapragada et al. |
| 6,716,225 | B2 | 4/2004 | Li et al. |
| 6,790,528 | B2 | 9/2004 | Wendorff et al. |
| 7,135,134 | B2 | 11/2006 | Tepper et al. |
| 7,163,545 | B2 | 1/2007 | Yaszemski et al. |
| 7,172,765 | B2 | 2/2007 | Chu et al. |
| 7,209,616 | B2 | 4/2007 | Welker et al. |
| 7,214,242 | B2 | 5/2007 | Abraham et al. |
| 7,276,271 | B2 | 10/2007 | Dubson et al. |
| 7,374,774 | B2 | 5/2008 | Bowlin et al. |
| 7,622,299 | B2 | 11/2009 | Sanders et al. |
| 2003/0171053 | A1 | 9/2003 | Sanders |
| 2004/0037813 | A1 | 2/2004 | Simpson et al. |
| 2004/0052861 | A1 | 3/2004 | Hatcher |
| 2004/0267362 | A1 | 12/2004 | Hwang et al. |
| 2005/0079470 | A1 | 4/2005 | Rutherford et al. |
| 2006/0002978 | A1 | 1/2006 | Shea et al. |
| 2006/0226580 | A1 | 10/2006 | Xia et al. |
| 2006/0273279 | A1 | 12/2006 | Kaplan et al. |
| 2007/0009570 | A1 | 1/2007 | Kim et al. |
| 2007/0026039 | A1 | 2/2007 | Drumheller et al. |
| 2007/0087027 | A1 | 4/2007 | Greenhalgh et al. |
| 2007/0269481 | A1 | 11/2007 | Li et al. |
| 2008/0038352 | A1 | 2/2008 | Simpson et al. |
| 2008/0220042 | A1 | 9/2008 | Hashi et al. |
| 2009/0091065 | A1 | 4/2009 | Katti et al. |
| 2010/0233115 | A1 | 9/2010 | Patel et al. |

FOREIGN PATENT DOCUMENTS

| | | | |
|---|---|---|---|
| WO | 02102432 | A1 | 12/2002 |
| WO | 03053216 | A2 | 7/2003 |
| WO | 03059965 | A1 | 7/2003 |
| WO | 2004032713 | A2 | 4/2004 |
| WO | 2005032418 | A2 | 4/2005 |
| WO | 2006096791 | A2 | 9/2006 |
| WO | 2006105441 | A2 | 10/2006 |
| WO | 2007089259 | A1 | 8/2007 |
| WO | 2007090102 | A2 | 8/2007 |
| WO | 2007112446 | A2 | 10/2007 |
| WO | 2007146261 | A2 | 12/2007 |
| WO | 2008013713 | A2 | 1/2008 |
| WO | 2008098220 | A1 | 8/2008 |

OTHER PUBLICATIONS

Barbolt, et al., "Biocompatibility evaluation of dura mater substitutes in an animal model", Neurol Res., vol. 23, 2001, 813-820.
Bejjani, et al., "Safety and efficacy of the porcine small intestinal submucosa dural substitute: results of a prospective multicenter study and literature review", J Neurosurg, Vo. 106, 2007, 1028-1033.
Bhatia, et al., "A synthetic dural prosthesis constructed from hydroxyethylmethacrylate hydrogels", J Neurosurg, vol. 83, 1995, 897-902.
Biroli, et al., "Novel Equine Collagen-Only Dural Substitute", Neurosurg [ONS Suppl 1], vol. 62, 2008, 273-274.
Brostrom, et al., "Biodegradable Films of Partly Branched Poly(L-lactide)- co-poly(ϵ-caprolactone) Copolymer: Modultation of Phase Morphology, Plasticization Properties and Thermal Depolymerization", Biomacromolecules, vol. 5, Issue 3, Abstract, 2004, 1124-1134.
Burger, et al., "Nanofibrousmaterials and their applications", Annu. Rev. Mater. Res., vol. 36, 2006, 333-368.
Castelnuovo, et al., "Endonasal Endoscopic Duraplasty: Our Experience", Skull Base, vol. 16, Issue 1, 2006, 19-23.
Dufrane, et al., "Clinical application of a physically and chemically processed human substitute for dura mater", J. Neurosurg, Vo. 98, 2003, 1198-1202.
Ekaputra, et al., "Dura Mater Regeneration with a Novel Synthetic, Bilayered Nanofibrous Dural Substitute: An Experimental Study", Nanomedicine, vol. 6., Issue 2, 2011, 325-337.
Haq, et al., "Postoperative fibrosis after surgical treatment of the porcine spinal cord: a comparison of dural substitutes", J Neurosurg Spine, vol. 2, 2005, 50-54.
Hida, et al., "Nonsuture dural repair using polyglycolic acid mesh and fibrin glue: clinical application to spinal surgery", Surgical Neurology, vol. 65, 2006, 136-143.
Hieb, et al., "Spontaneous Postoperative Cerebrospinal Fluid Leaks Following Application of Anti-Adhesion Barrier Gel", Spine, vol. 26, Issue 7, 2001, 748-751.
Klopp, et al., "Comparison of a Caprolactone/Lactide Film (Mesofol) to Two Polylactide Film Products as a Barrier to Postoperative Peridural Adhesion in an Ovine Dorsal Laminectomy Model", Spine, vol. 33, Issue. 14, 2008, 1518-1526.
Kurpinski, et al., "Dura mater regeneration with a novel synthetic, bilayered nanofibrous dural substitute: an experimental study", Nanomedicine, vol. 6, Issue 2, 2011, 325-337.
Laquerriere, et al., "Experimental evaluation of bilayered human collagen as a dural substitute", J Neurosurg, vol. 78, 1993, 487-491.
Leong, et al., "Solid Freeform Fabrication of Three-Dimensional Scaffolds for Engineering Replacement Tissues and Organs", Biomaterials, vol. 24, 2003, 2363-2378.
Li, et al., "Electrospinning of Polymeric and Ceramic Fibers as Uniaxially Aligned Arrays", Nano Letters, vol. 3, Issue 8, 2003, 1167-1171.
Maikos, et al., "Mechanical Properties of Dura Mater from the Rat Brain and Spinal Cord", J Neurotrauma, vol. 25, 2008, 38-51.
Martin, et al., "Wound Healing—Aiming for Perfect Skin Regeneration", Science, vol. 276, 1997, 75-81.
McCall, et al., "Use of resorbable collagen dural substitutes in the presence of cranial and spinal infections—report of 3 cases", Surg Neurol, vol. 70, Issue 1, 2008, 92-96.
Mello, et al., "Duraplasty with biosynthetic cellulose: An experimental study", J. Neurosurg., vol. 86, 1997, 143-150.
Mukai, et al., "Development of Watertight and Bioabsorbable Synthetic Dural Substitutes", Artif Organs, vol. 32, Issue 6, 2008, 473-483.
Narotam, et al., "A clinicopathological study of collagen sponge as a dural graft in neurosurgery", J Neurosurg, vol. 82, 1995, 406-412.
Narotam, et al., "Collagen Matrix (DuraGen) in Dural Repair: Analysis of a New Modified Technique", Spine, vol. 29, Issue 24, 2004, 2861-2867.

(56) References Cited

OTHER PUBLICATIONS

Narotam, et al., "Collagen matrix duraplasty for cranial and spinal surgery: a clinical and imaging study", J Neurosurg, vol. 106, 2007, 45-51.
Parizek, et al., "Ovine pericardium: A new material for duraplasty", J Neurosurg, vol. 84, 1996, 508-513.
Preul, et al., "A Unique Dual-Function Device: A Dural Sealant with Adhesion Prevention Properties", DuraSeal Spine White Paper, 2005, 5 pages.
Preul, et al., "Obtaining Watertight Closures of Duraplasty Onlay Grafts in a Craniotomy Preclinical Model", DuraSeal Package Insert, 2005, 8 pages.
Rabinowitz, et al., "Growth of rat cortical neurons on DuraGen, a collagen-based dural graft matrix", Neurol Res, vol. 27, 2005, 887-894.
Rosen, et al., "Artificial Nerve Graft Using Collagen as an Extracellular Matrix for Nerve Repair Compared with Sutured Autograft in a Rat Model", Ann. of Plast. Surg., vol. 25 Issue 5, 1990, 375-387.
Runza, et al., "Lumbar Dura Mater Biomechanics: Experimental Characterization and Scanning Electron Microscopy Observations", Anesth. Analg., vol. 88, 1999, 1317-1321.
Sacks, et al., "Local Mechanical Anisotropy in Human Cranial Dura Mater Allografts", Journal of Biomechanical Engineering, vol. 120, 1998, 541-544.
Salgado, et al., "Bone Tissue Engineering: State of the Art and Future Trends", Macromol. Biosci., vol. 4, 2004, 743-765.
Tachibana, et al., "Evaluation of the healing process after dural reconstruction achieved using a free fascial graft", J Neurosurg, vol. 96, 2002, 280-286.
Tatsui, et al., "Evaluation of DuraGen in preventing peridural fibrosis in rabbits", J Neurosurg Spine, vol. 4, 2006, 51-59.
Yamada, et al., "Clinical application of a new bioabsorbable artificial dura mater", J Neurosurg, vol. 96, 2002, 731-735.
Yamada, et al., "Development of a dural substitute from synthetic bioabsorbable polymers", J Neurosurg, vol. 86, 1997, 1012-1017.
Yao, et al., "Fabrication of Polycaprolactone Scaffolds Using a Sacrificial Compression-Molding Process", Journal of Biomedical Materials Research Part B: Applied Biomaterials, vol. 77B, Issue 2 (Wiley InterScience at www.interscience.wiley.com), 2007, 287-295.
Zerris, et al., "Repair of the Dura Mater with Processed Collagen Devices", Journal of Biomedical Materials Research Part B: Applied Biomaterials, vol. 83B, Issue 2, 2007, 580-588.
European Patent Office, "Extended European Search Report dated Dec. 11, 2013", European Patent Application No. 09819836.9, 6 pages.
International Bureau, "PCT International Search Report and Written Opinion dated Jan. 4, 2010", PCT Application No. PCT/US2009/059890, 10 pages.
International Bureau, "PCT International Search Report dated Jul. 10, 2012", PCT Application No. PCT/US2011/063142, 3 pages.
Xie, et al., "Radially Aligned, Electrospun Nanofibers as Dural Substitutes for Wound Closure and Tissue Regeneration Applications", ACS Nano, 2010, vol. 4, Issue 9, 2010, 5027-5036.
U.S. Patent and Trademark Office, "Restriction Requirement dated Dec. 29, 2011", U.S. Appl. No. 12/575,432, 9 pages.
Prosecution Document, "Response to Restriction Requirement filed Jan. 27, 2012", U.S. Appl. No. 12/575,432, 7 pages.
U.S. Patent and Trademark Office, "Non final Office Action dated Feb. 17, 2012", U.S. Appl. No. 12/575,432, 7 pages.
Prosecution Document, "Response to Non final Office Action filed May 17, 2012", U.S. Appl. No. 12/575,432, 10 pages.
U.S. Patent and Trademark Office, "Final Office Action dated Jun. 26, 2012", U.S. Appl. No. 12/575,432, 8 pages.
Prosecution Document, "Response to Final Office Action filed Aug. 27, 2012", U.S. Appl. No. 12/575,432, 14 pages.
U.S. Patent and Trademark Office, "Advisory Action dated Sep. 21, 2012", U.S. Appl. No. 12/575,432, 3 pages.
Prosecution Document, "RCE and Response to Final Office Action and Advisory Action filed Dec. 19, 2012", U.S. Appl. No. 12/575,432, 11 pages.
U.S. Patent and Trademark Office, "Interview Summary dated Jan. 2, 2013", U.S. Appl. No. 12/575,432, 3 pages.
U.S. Patent and Trademark Office, "Non final Office Action dated Dec. 23, 2013", U.S. Appl. No. 12/575,432, 8 pages.
Prosecution Document, "Response to Non final Office Action filed Apr. 22, 2014", U.S. Appl. No. 12/575,432, 13 pages.
U.S. Patent and Trademark Office, "Notice of Allowance dated Jun. 2, 2014", U.S. Appl. No. 12/575,432, 7 pages.

FIBROUS POLYMER SCAFFOLDS HAVING DIAMETRICALLY PATTERNED POLYMER FIBERS

CROSS-REFERENCE TO RELATED APPLICATIONS

This application claims the benefit under 35 U.S.C. §119(e) of U.S. Provisional Patent Application No. 61/419,869 filed Dec. 5, 2010, and is the U.S. National Stage entry under 35 U.S.C. §371 of PCT Patent Application No. PCT/US2011/063142, the contents of both of which are incorporated by reference herein in their entirety.

FIELD

The disclosure relates to fibrous scaffolds with at least one layer of diametrically patterned polymer fibers finding application as medical devices for the repair of wounds, surgical incisions and/or biopsies and for promoting and/or improving the regeneration of anatomical biological components (i.e., biological tissues including, without limitation, abdominal wall, amniotic sac, bladder, blood vessels, brain, cardiac tissue, fascia, gingival tissue, intestine, ligaments, meningeal tissue, mucous membranes, muscle, nerves, skin, spinal cord, stomach, tendons, etc.).

BACKGROUND

Electrospinning is a technique known in the art for producing articles composed of polymer fibers. See U.S. Pat. No. 4,323,525. More recently, U.S. Pat. No. 7,276,271 disclosed a fibrous polymer tubular structure. Substrates with nanoscale aligned geometries are disclosed in U.S. Pat. No. 6,676,675. The use of electrospun fibrous polymer grafts in medical applications is disclosed in U.S. Pat. No. 7,172,765.

Modified electrospinning methods for forming directed fibers are also disclosed in U.S. Pat. No. 7,135,134. PCT Publication Nos. WO 2007/146261 and WO 2007/090102 disclose various aspects of polymer fibrous scaffold sheets.

SUMMARY

There is a need in the art for fibrous polymer scaffolds having at least one layer of diametrically patterned polymer fibers for promoting rapid tissue growth across tissue defects, and for providing flexibility and tensile strength in multiple directions. Such scaffolds provide stability in a wide range of applications, particularly biomedical applications. Further, there is a need for apparatuses designed to manufacture such scaffolds. The present disclosure addresses these and other needs.

Fibrous polymer scaffolds having at least a first layer of diametrically patterned polymer fibers are disclosed. Fibrous polymer scaffolds with at least one layer of diametrically patterned fibers may be used to repair, heal and/or regenerate wounded tissues and organs. These uses can include, without limitation, uses as tissue substitutes and/or tissue regeneration matrices for wounds and/or defects in biological tissues including, without limitation, abdominal wall, amniotic sac, bladder, blood vessels, brain, cardiac tissue, fascia, gingival tissue, intestine, ligaments, meningeal tissue, mucous membranes, muscle, nerves, skin, spinal cord, stomach, tendons, etc., uses in combination with cells, uses in combination with biomolecules, and uses in combination with pharmaceutically acceptable excipients. In various embodiments, the diametrically patterned fiber layer of the fibrous polymer scaffold is placed in contact with a tissue defect or wound. In various embodiments the convergence region of the diametrically patterned fiber layer is positioned over the center of the tissue defect or wound. The diametrically patterned fibers direct cell and tissue growth from the entire periphery of the defect toward the center.

In various aspects, the fibrous polymer scaffolds have a second layer that can include aligned, unaligned or randomly oriented fibers. In various aspects, the scaffolds can include a plurality of layers including, without limitation, three, four, five, six, seven, eight, nine, ten or more layers.

The polymer scaffolds of the disclosure can be formed into a variety of shapes. In various aspects, the polymer scaffolds can be in the shape of a membrane. The membrane may take any desired geometrical shape including, without limitation, a square, rectangle, circle, oval and other shapes as in FIG. 1. The shape of the scaffolds may be designed to correspond to a specific tissue or specific tissue defect.

Additional layers can be formed from different polymers than the first layer, or the same polymer as the first layer. In some embodiments, the polymer fibers of the first layer and the polymer fibers of the secondary layers comprise a single, unbroken polymer fiber. In some embodiments, the polymer fibers of the first layer and the polymer fibers of the secondary layers comprise multiple, unbroken polymer fibers. In some embodiments, at least one polymer fiber in the first layer and at least one polymer fiber in the secondary layers is the same, continuous polymer fiber. In some embodiments, the fibers of the first layer and the fibers of the secondary layers comprise two polymers present in two continuous fibers. In some embodiments, the fibers of the first layer and the fibers of the secondary layers comprise three polymers present in three continuous fibers. In some embodiments, the fibers of the first layer and the fibers of the secondary layers comprise four polymers present in four continuous fibers. In some embodiments, the fibers of the first layer and the fibers of the secondary layers comprise five polymers present in five continuous fibers.

In some embodiments, the first layer is formed from diametrically patterned polymer fibers. The secondary layers can be formed from aligned polymer fibers, or from polymer fibers that are substantially unaligned or randomly oriented. In those embodiments where the secondary layers are formed from aligned polymer fibers, the orientation of the aligned fibers of the secondary layers can be offset from the alignment of the fibers of the first layer.

In various aspects, the scaffold ranges from about 100 microns to about 500 microns thick. In some embodiments, the thickness of the first layer is less than the thickness of the secondary layers. In some embodiments, the thickness of the first layer is greater than about 1 micron and less than about 70 microns thick. In some embodiments, the thickness of the first layer is greater than about 70 microns and less than about 150 microns thick. In some embodiments, the thickness of the first layer is greater than about 150 microns and less than about 300 microns thick. In some embodiments, the thickness of the secondary layers of fibers is greater than about 150 microns and less than about 330 microns thick. In some embodiments, the total thickness of the scaffold is about 100 to about 200 microns, about 150 to about 250 microns, about 300 to about 400 microns, or about 500 microns. In some embodiments, the total thickness of the scaffold is greater than about 500 microns.

In various aspects, the polymer fibers of the first layer and the polymer fibers of the secondary layers are comprised of biodegradable polymers.

In various aspects, the polymer fibers of the fibrous polymer scaffolds can further optionally comprise an additive selected from the group consisting of poly(propylene glycol), poly(ethylene oxide), triethyl citrate, glycerol, poly(ethylene glycol), and combinations thereof.

In various aspects, the polymer fibers of the scaffolds can further optionally comprise a salt. In some embodiments, the salt can be sodium acetate.

In various aspects, kits for the repair of wounds, surgical incisions or biopsies are provided. In some embodiments, the kits comprise at least one fibrous polymer scaffold and instructions for using the scaffold to repair wounds, surgical incisions and/or biopsies.

In various aspects, methods of implanting fibrous polymer scaffolds are provided. In some embodiments, the methods are directed toward treating an injury or defect in a subject and comprise applying a scaffold to an injury or defect site on or in said subject, in an amount, and under conditions, sufficient to treat the injury.

The polymer fibers comprising any one or more of the layers can comprise a material selected from an aliphatic polyester, a poly(alkylene) oxide, poly(L-lactic acid), 70/30 L-lactide/e-caprolactone co-polymer, poly(caprolactone), poly(DL-lactide-co-caprolactone), poly(D-lactide-co-caprolactone), poly(L-lactide-co-caprolactone), poly(lactide-co-glycolic acid), poly(vinylpyrrolidine), poly(dimethylsiloxane), poly(lysine), collagen, laminin, fibronectin, elastin, alginate, fibrin, hyaluronic acid, proteoglycans, polypeptides, poly(ethylene-co-vinyl) alcohol, poly(vinyl) alcohol, poly(ethylene)glycol, poly(propylene)glycol, poly-L-lactide-co-glycolide-co-ε-caprolactone, poly(tetrafluoroethylene), poly(dioxanone), polyglactin 910 and combinations thereof.

The aliphatic polyester can be selected from D-lactide, L-lactide, poly(lactic acid), poly(lactide)glycolic acid, poly(glycolic acid), poly(glycolide), glycolide, poly(lactide-co-glycolide), poly(lactic acid-co-glycolic acid), epsilon-caprolactone, poly(epsilon-caprolactone) and a combination thereof. The poly(alkylene) oxide can be selected from poly(ethylene) oxide and poly(propylene) oxide.

The polymer fibers of the first layer and the polymer fibers of the second layer can comprise poly(L-lactide-co-caprolactone). The polymer fibers of the first layer and the polymer fibers of the second layer can comprise poly(L-lactic acid). The polymer fibers of the first layer and the polymer fibers of the second layer can comprise poly(L-lactide-co-caprolactone) and poly(L-lactic acid). One of a plurality of continuous fibers can comprise poly(L-lactide-co-caprolactone) and another of a plurality of continuous fibers can comprise poly(L-lactic acid).

The fibrous polymer scaffolds can also comprise an additive. The additive can be selected from poly(propylene glycol), poly(ethylene oxide), triethyl citrate, glycerol, poly(ethylene glycol), and combinations thereof. The additive can be poly(propylene glycol). The additive can be present in an amount ranging from about 0.1% to about 10% (wt %) of the total weight of the polymer. The additive can be present in an amount selected from about 1.0% to about 2.0%, about 2.0% to about 3.0%, about 3.0% to about 4.0%, about 4.0% to about 5.0%, about 5.0% to about 6.0%, about 6.0% to about 7.0%, about 7.0% to about 8.0%, about 8.0% to about 9.0%, and about 9.0% to about 10.0% of the total weight of the polymer.

In various aspects, kits for the repair of wounds, surgical incisions or biopsies are disclosed, the kits comprising (i) a fibrous polymer scaffold comprising at least a first layer of diametrically aligned polymer fibers and a second layer of polymer fibers, wherein the fibers of the second layer are substantially unaligned, and wherein at least one fiber in the first layer of fibers and at least one fiber in the second layer of fibers is the same continuous fiber; and (ii) instructions for using the scaffold to repair wounds, surgical incisions or biopsies by promoting the regeneration of anatomical biological components. The anatomical biological components can be selected from abdominal wall, amniotic sac, bladder, blood vessels, brain, cardiac tissue, fascia, gingival tissue, intestine, ligaments, meningeal tissue, mucous membranes, muscle, nerves, skin, spinal cord, stomach, and tendons. The first layer of fibers of the scaffold and the second layer of fibers of the scaffold can comprise a single continuous fiber. The first layer of fibers of the scaffold and the second layer of fibers of the scaffold can comprise two continuous fibers. The fibers of the second layer of the scaffold can have a random orientation. The fibers of the second layer can be aligned, in which case they will be offset from the diametrical alignment of the fibers of the first layer. The first layer of the scaffold can be the innermost layer and the second layer can be the outermost layer. The scaffold can be a membrane.

In various aspects, methods of implanting fibrous polymer scaffolds are provided, the methods comprising: contacting a defect in a tissue of a subject with a single layer of a fibrous polymer scaffold, the scaffold comprising at least a first layer of diametrically patterned polymer fibers. The defect can be selected from wounds, surgical incisions and biopsies. The contacting can comprise placing the scaffold over the defect. The contacting can comprise placing the scaffold completely within the defect. The contacting can comprise placing the scaffold underneath the defect. The scaffold can be secured in place at the defect. The securing can comprise suturing the scaffold and/or gluing the scaffold.

In various aspects, fibrous polymer scaffolds are disclosed comprising at least a first layer of diametrically aligned polymer fibers and a second layer of polymer fibers having a different alignment than the fibers in the first layer. At least one fiber in the first layer of fibers and at least one fiber in the second layer of fibers can be the same continuous fiber. The first and second layers of fibers can comprise a single continuous fiber. The scaffold can be a membrane. The first layer of diametrically aligned fibers can be greater than 1 micron and less than 70 microns thick. The first layer of diametrically aligned fibers can be greater than 70 microns and less than 150 microns thick. The first layer of diametrically aligned fibers can be greater than 150 microns and less than 300 microns thick. The second layer of diametrically aligned fibers can be greater than 150 microns and less than 330 microns thick. The total thickness of all layers can be greater than 20 microns and less than 150 microns. The total thickness of all layers can be greater than 150 microns and less than 250 microns. The total thickness of all layers can be greater than 250 microns and less than 300 microns. The total thickness of all layers can be greater than 300 microns and less than 400 microns. The second layer can comprise fibers uniaxially aligned in parallel with an axis of the fibrous scaffold.

The fibers can comprise a material selected from the group consisting of aliphatic polyesters, polyhydroxyalkanoates, polyurethanes, polyalkylene oxides, polydimethylsiloxane, polyvinylalcohol, polyvinylpyrrolidone, polylysine, collagen, gelatin, laminin, fibronectin, elastin, alginate, fibrin, hyaluronic acid, proteoglycans, polypeptides, polysaccharides and combinations thereof. The aliphatic polyester can be selected from the group consisting of D-lactide, L-lactide, poly(lactic acid), poly(lactide)glycolic acid, poly(glycolic acid), poly(glycolide), glycolide, poly(lactide-co-glycolide) or PLGA, poly(lactic acid-co-glycolic acid), epsilon-caprolactone, poly(epsilon-caprolactone), and combinations thereof. The aliphatic polyester can be poly(L-lactide). The aliphatic polyester can be poly(L-lactide-co-caprolactone.

The scaffolds can further comprise an additive. The additive can be selected from triethyl citrate, glycerol, poly(ethylene glycol), poly(propylene glycol), glycerol, and combinations thereof. The additive can be from 0.01% to 25% of the weight of the polymer.

The fibrous polymer scaffolds can comprise a salt selected from NaCl, KH2PO4, K2HPO4, KIO3, KCl, MgSO4, MgCl2, NaHCO3, CaCl2, salt of acetic acid, salt of ascorbic acid, salt of citric acid, salt of lactic acid, salt of glycolic acid, and mixtures thereof.

In other aspects, apparatuses for making fibrous polymer scaffolds are provided. In some embodiments, an apparatus for making fibrous polymer scaffolds is provided that includes a rotational collector assembly having an electrically insulating disk in front of and conformally contacting a thin grounded metal strip extending across the diameter of the disk and two electrically charged point electrodes positioned equidistant from the center of the disk. A charged electrically conducting spinneret configured to release a polymer solution onto the rotating disk is positioned normal disk surface.

In various aspects, the rate of revolution of the rotational assemblies of the apparatuses can be varied. In some embodiments, the rotational assemblies are rotated at a rate of greater than 1 revolution per minute (RPM), greater than 5 RPM, greater than 20 RPM, greater than 100 RPM, greater than 800 RPM, greater than 1,000 RPM, greater than 2,000 RPM, greater than 3,000 RPM, greater than 4,000 RPM, or greater than 5,000 RPM during the formation of the layers. In some embodiments, the rotational assemblies are rotated at a rate of less than 5,000 RPM, less than 4,000 RPM, less than 3,000 RPM, less than 2,000 RPM, less than 1,000 RPM, less than 800 RPM, less than 100 RPM, less than 20 RPM, less than 5 RPM, or less than 1 RPM during the formation of the layers. In some embodiments, the rotational assemblies are rotated during the formation of at least one layer of fibers at a rate selected from 1 RPM, 5 RPM, 10 RPM, 15 RPM, 20 RPM, 25 RPM, 30 RPM and 35 RPM. In some embodiments, the rotational assemblies are rotated at a rate of 20 RPM during the formation of at least one layer of fibers.

The rotational assembly can be positioned a distance of 5 cm to 30 cm from a spinneret from which a polymer solution is released. The spinneret can move parallel to the diametrical axis of the rotational assembly during formation of at least one layer. The spinneret can traverse the length parallel to the diametrical axis of the electrospinning assembly at a rate of 1 cm/min.

In some embodiments, the apparatuses are configured for the polymer-containing spinneret to move laterally to the diametrical surfaces of the rotational assemblies during formation of one or more layers.

DETAILED DESCRIPTION

Definitions

"Aligned" refers to the orientation of fibers in a fibrous polymer scaffold wherein at least 80% of the fibers are oriented in a defined direction and their orientation forms either a single axis or multiple axes of alignment. The orientation of any given fiber can deviate from a given axis of alignment and the deviation can be expressed as the angle formed between the alignment axis and orientation of the fiber. A deviation angle of 0° exhibits perfect alignment with the given axis and 90° (or −90°) exhibits orthogonal alignment of the fiber with respect to the given axis of alignment. When multiple axes of alignment exist in a given layer, the alignment of a particular fiber is determined in relation to its closest axis. In exemplary embodiments, the standard deviation of the aligned fibers from their closest axes of alignment can be an angle selected from between 0° and 1°, between 0° and 3°, between 0° and 5°, between 0° and 10°, between 0° and 20°, or between 0° and 25°. Where the fibers of a layer of a fibrous polymer scaffold are comprised of a single fiber that loops over itself, the term "aligned" refers to the portion of the fiber spanning either between two points on the periphery of the membrane or between a point on the periphery and a point in a defined region of the membrane, such as a fiber convergence region.

Figure 1:
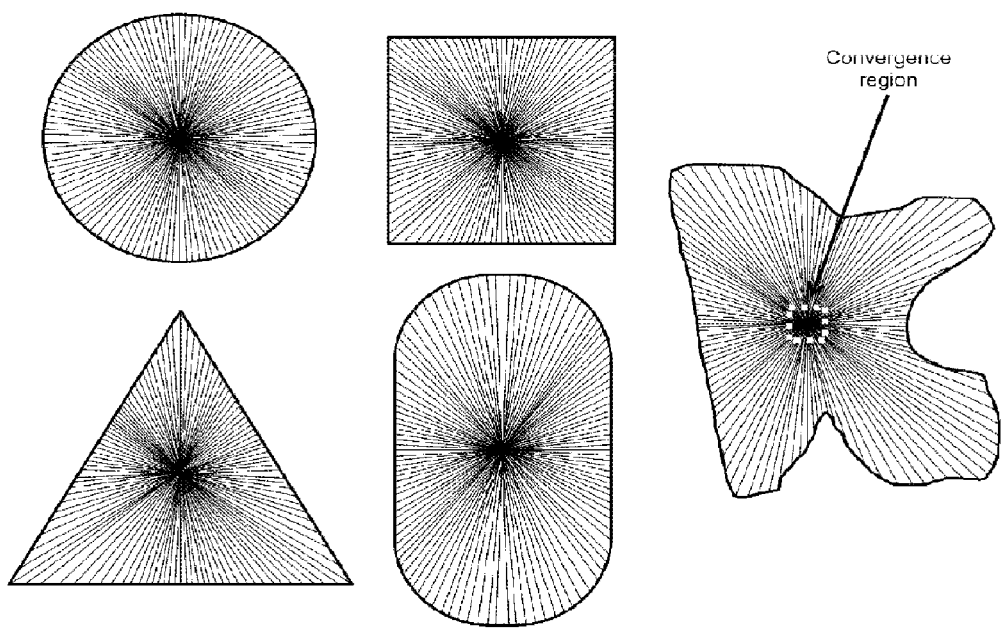
FIG. 1 depicts examples of membranes according to the present disclosure of various shapes and having diametrically patterned fibers. This figure also provides examples of a convergence region.

The term "convergence region," as used herein in the context of a fibrous polymer scaffold, refers to an area through which at least 80% of diametrical fibers in the scaffold intersect. A convergence region does not necessarily refer to the center or middle of the scaffold. An example of a convergence region is depicted in FIG. 1.

The term "diametrical axis," as used herein in the context of a fibrous polymer scaffold, refers to any straight axis that spans between two discrete points located on the periphery of the scaffold while also passing through a defined convergence region located within the boundary of the periphery.

The term "diametrical fiber," as used herein in the context of a fibrous polymer scaffold, refers to a fiber within the scaffold that spans two points on the periphery of the scaffold and is aligned along a diametrical axis of the scaffold.

The term "diametrically patterned" or "diametrically aligned," as used herein in the context of a fibrous polymer scaffold, refers to a plurality of diametrical fibers that are oriented along individual diametrical axes sharing a defined convergence region within the scaffold. In a diametrically patterned scaffold, there are multiple diametrical axes that pass through a defined convergence region.

The term "membrane," as used herein, refers to a fibrous polymer scaffold that is essentially flat, or planar in shape. As used herein, a membrane has at least a first layer of fibers and may or may not have additional layers of fibers. In varying embodiments, a membrane can have more than two layers of fibers. Each layer of a membrane may have a different orientation of fiber alignment.

The term "periphery," as used herein in the context of a fibrous polymer scaffold, refers to the boundary line encompassing the plane of the scaffold. The periphery of a scaffold is not necessarily circular.

The term "uniaxially aligned," as used herein in the context of a fibrous polymer scaffold, refers to aligned fibers that are oriented parallel to a single axis of alignment in a scaffold.

Reference is now made in detail to certain embodiments of scaffolds, methods of use, and methods of making. The disclosed embodiments are not intended to be limiting of the claims. To the contrary, the claims are intended to cover all alternatives, modifications, and equivalents.

Diametrically Patterned Polymer Fibers

Fibrous polymer scaffolds of this disclosure comprise at least one layer of diametrically patterned polymer fibers. The current disclosure comprises diametrical fibers that each span two edges of the scaffold and also pass through a convergence region with no bends or discontinuities of the fibers at the convergence region. Diametrical patterning of a plurality of fibers within the fibrous polymer scaffold results in diametrical fibers sharing a defined convergence region within the scaffold. The diametrical fibers are thereby arranged in a pattern in which the fibers appear to radiate from the convergence point toward the periphery of the scaffold.

Diametrical patterning within a scaffold is distinguished from radial patterning or radial alignment wherein the radially aligned fibers span straight across only one edge and the convergence region within the scaffold and may have discontinuities at the convergence region. A radially aligned fiber only spans a location between the center, or convergence region, of a scaffold and the periphery of a scaffold. Radially aligned fibers thus do not cross the entire scaffold. In this regard, because of the electrospinning process, scaffolds comprising radially aligned fibers may have discontinuities at the convergence region. In contrast, a diametrically aligned fiber crosses the entire scaffold, from one discrete point on the periphery of the scaffold to another, and also passes across a convergence region of the scaffold. Fibrous polymer scaffolds provided according to the current disclosure comprise diametrically aligned fibers and thus may be expected to demonstrate higher tensile strength than fibrous polymer scaffolds comprising radially aligned fibers. This is because diametrical fibers are diametrically aligned straight through a convergence region in a scaffold, whereas radially aligned fibers loop back over themselves within the convergence region, thereby producing a fiber structure with reduced organization of the tensile elements in that region. Diametrically patterned fibrous polymer scaffolds may also be expected to promote enhanced wound healing and cell migration characteristics when compared to radially aligned fibrous polymer scaffolds, particularly near the convergence region, because the diametrical fibers are diametrically aligned straight through the convergence region whereas radially aligned fibers may have discontinuities, thereby reducing overall alignment in that region.

Fibrous polymer scaffolds can be made through electrospinning, as described herein. The individual fibers within one or more layers of the scaffolds can be diametrically aligned during electrospinning, as described herein. In several aspects, the individual polymer fibers comprising one or more layers of the scaffolds are diametrically aligned during electrospinning.

Diametrically Patterned Fibrous Polymer Scaffolds

The present disclosure relates to a fibrous polymer scaffold with one or more layers of fibers wherein at least one layer comprises diametrically patterned fibers. In some embodiments, the fibrous polymer scaffold may be in the shape of a membrane or sheet. In some embodiments, the membrane or sheet may be a circle, oval, rectangle, square or other shape. The present disclosure is generally directed to fibrous scaffolds having at least one layer of diametrically patterned polymer fibers, apparatuses and methods of their manufacture, methods of use, and kits comprising the scaffolds.

Scaffolds generally refer to, but are not limited to, membrane structures formed from polymer microfibers or polymer fibers as described herein. In various embodiments, greater than 50%, greater than 60%, greater than 70%, greater than 80%, greater than 90%, greater than 91%, greater than 92%, greater than 93%, greater than 94%, greater than 95%, greater than 96%, greater than 97%, greater than 98%, or greater than 99% of a scaffold is w/w comprised of the polymer fibers as described herein.

Scaffolds can include, without limitation, membrane structures formed from polymer microfibers or nanofibers as described herein. Diametrically patterned polymer scaffolds disclosed herein can be diametrically patterned fibrous polymer scaffolds, such as nanofiber polymer scaffolds. In various aspects, the fibrous polymer scaffolds can also be micropatterned polymer scaffolds. The scaffolds of the present disclosure contain at least one layer and can contain a plurality of layers. In some embodiments, the composition has between about 1 and about 10 fibrous layers. In various aspects, scaffolds can include more than two layers. In some embodiments, the first and second layers are adjacent, and one or more additional layers can be disposed on the outside of the second layer.

In various aspects, a single layer of fibers in a scaffold can be constructed from one, two, three, four, five, or more continuous, unbroken polymer fibers. Similarly, in various aspects a plurality of layers of fibers in a single scaffold can also be constructed from one, two, three, four, five or more continuous, unbroken polymer fibers. Each polymer fiber may be deposited via the use of a spinneret, as described herein. For example, when it is desired for a single layer of a scaffold to have diametrically patterned polymer fibers, the fiber can loop back upon itself at the edges and pass through the convergence region of the scaffold repeatedly. Where the diametrically aligned fibers are comprised of one, two, three or more continuous polymer fibers, each continuous fiber can loop back upon itself to form a diametrically aligned layer of fibers.

In some embodiments, the scaffolds can comprise multiple layers of fibers wherein the layers are differentiated by chemical composition or average fiber alignment within each individual layer. Scaffolds of multiple layers of polymer fibers may have multiple differential alignments for each layer, providing tensile strength, suture retention strength, elasticity, flexibility, and rigidity while minimizing delamination of the layers of fibers.

Each layer can contain fibers in a unique pattern or alignment, wherein each layer of the multilayer polymer scaffolds can optionally be unaligned, diametrically aligned, or aligned with a non-diametrical orientation. For example, at least one layer may contain diametrically patterned fibers and at least one further layer may contain randomly oriented fibers.

The layers of fibers in a single scaffold can be distinguished by differential alignment of the fibers composing each of the layers. Each layer of the multilayer polymer scaffolds can have polymer fibers that are unaligned, diametrically aligned, or aligned with a non-diametrical orientation. For example, the first layer of the scaffold membranes may comprise diametrically patterned fibers around a convergence region of the scaffold membrane. A second layer of fibers may comprise fibers that are uniaxially aligned or that are randomly oriented, thereby providing a difference in the alignment of the fibers between the two layers. The different alignment of polymer fibers between the different layers of the scaffolds provides additional mechanical integrity and tensile strength in multiple directions. In some embodiments, the multilayer scaffolds display greater structural integrity due to the presence of at least one layer comprising randomly oriented fibers. Randomly oriented fibers can provide mechanical integrity to the scaffold membranes by increasing its flexibility, tensility and/or suturability.

Each layer of fibers in a single scaffold may comprise diametrically aligned fibers or randomly oriented fibers. For example, in embodiments with at least two adjacent layers that are formed from continuous polymer fibers, each layer can comprise diametrically aligned fibers, each layer can comprise non-diametrically aligned fibers, each layer can comprise randomly oriented fibers, or the individual layers may comprise differing alignment. The layers of fibers can thus be distinguished by differential alignment of fibers composing the layers. For example, a first layer can comprise diametrically aligned fibers and a second layer of fibers can comprise unaligned fibers. In some embodiments, a first layer of a multilayer polymer scaffold comprises diametrically aligned fibers and a second layer of the scaffold comprises randomly oriented fibers, wherein the fibers of the first layer and the fibers of the second layer are formed from at least one continuous polymer fiber.

In various embodiments, a single layer of a scaffold can have an alignment which can be defined relative to at least one axis of the layer. In some embodiments, the scaffold has an asymmetrical shape such as an oval or rectangle. In some embodiments, a single layer of a scaffold having an asymmetrical shape can be defined relative to a long axis of the scaffold. In some embodiments, a single layer of a scaffold having an asymmetrical shape can be defined relative to a short axis of the scaffold. In some embodiments, a scaffold having an asymmetrical shape can have at least one layer of polymer fibers that are aligned essentially parallel to its long axis. In some embodiments, a scaffold having an asymmetrical shape can have at least one layer of polymer fibers that are aligned essentially parallel to its short axis. In some embodiments, fibers can be randomly aligned, or orthogonally aligned, with respect to an axis of the scaffold. In some embodiments, the alignment of fibers in a single layer of a scaffold having an asymmetrical shape may be at an angle relative to either the short axis of the scaffold, or the long axis of the scaffold. In some embodiments, the angle can be from 0° to 90°. In some embodiments, the angle can be from 10° to 80°. In some embodiments, the angle can be from 20° to 70°. In some embodiments, the angle can be from 30° to 60°. In some embodiments, the angle can be from 40° to 50°. In some embodiments, the angle can be 45°.

In various aspects, scaffolds can include more than two layers. In various aspects, scaffolds can comprise a plurality of layers of fibers. In some embodiments, the first layer of polymer fibers contacts the second layer of polymer fibers, or the first and second layers are adjacent, and one or more additional layers can be disposed on the outside of one of the two layers as a third layer, a fourth layer, a fifth layer, and so on. In other embodiments, one of the plurality of layers in a scaffold can be one or more intervening, non-electrospun, non-polymer and/or non-fibrous layers. In various embodiments, an intervening layer can be an adhesive layer. In some embodiments, the adhesives can be any biocompatible adhesive known in the art. In some embodiments, an intervening layer can provide additional mechanical strength and/or integrity, flexibility, tensility, or other desired properties. In some embodiments, an intervening layer can comprise a molecule or therapeutic compound.

In certain embodiments, the fibrous polymer scaffold comprises a first layer of diametrically patterned fibers and a second layer of uniaxially aligned fibers with average fiber alignment parallel to one axis of the scaffold. In certain embodiments, the fibrous polymer scaffold comprises a first layer of diametrically patterned fibers and a second layer of unaligned fibers.

Fibrous layers of polymer fibers may also be oriented in the same direction (or in a similar random orientation) continuously or discontinuously. For example, in embodiments with at least two adjacent layers that are formed from discontinuous fibers, each layer can comprise diametrically patterned fibers within a membrane. In embodiments where at least two adjacent layers are formed from continuous fibers, the layers can differ in their alignment relative to a particular axis or set of axes as disclosed herein.

The fibrous scaffolds have specific properties, including the ability to retain a specific shape or geometry, flexibility, and alignment of fiber components in the absence of any non-fiber component. The scaffolds can thus be formed into specific or desired shapes or geometries including, without limitation, square, round, oval, and rectangular shaped membranes. The scaffolds may optionally be cut or trimmed into any desired shape or size without any loss of function.

The mechanical integrity of the diametrically patterned polymer scaffolds allow them to be readily suturable, with minimal leak points created from the use of sutures with the scaffolds. Additionally, the structure of the scaffolds make them sufficiently rigid such that they hold their shape, remain in place at a defect site in a subject, and are not prone to falling apart in the hands of the user, thereby facilitating their use.

The layers of fibers comprising a scaffold can be distinguished by differential alignment of fibers between the layers. For example, in the context of a membrane, the first layer of the scaffold may comprise diametrically patterned fibers around the convergence region of the membrane. The second layer of fibers can be selected from diametrically aligned, uniaxially aligned, and unaligned. Different alignment of polymer fibers between different layers can provide additional tensile strength in multiple directions.

In various aspects, a layer of a scaffold can be constructed from a single unbroken polymer fiber, or from a plurality of unbroken polymer fibers. For example, where fibers are patterned diametrically within a scaffold membrane, the fiber can loop back and forth upon itself during manufacture of the layer. For example, layers of fibers diametrically aligned along diametrical axes within a single layer of a scaffold membrane traverse these axes of the layer and are connected at the periphery of the scaffold.

As described herein, in certain embodiments, different layers of fibers can be constructed from the same fiber (continuous) or different fibers (discontinuous). In some embodiments, each layer of the scaffolds can be comprised of at least one continuous polymer fiber and at least one polymer fiber can also be continuous between the layers of the scaffolds as well, as described herein. The use of continuous fibers between the layers of the scaffolds makes the layers resistant to separation as the polymer chemistry between the layers is similar. The layers thus resist delamination or separation, contributing to the mechanical integrity and strength of the scaffolds.

In various aspects, the fibrous polymer scaffolds having at least one layer of diametrically patterned fibers are produced by electrospinning polymers onto the surface of a rotational disk assembly. In some aspects, the rotational disk assembly comprises an electrically insulating disk with its back surface in conformal contact with a grounded metal strip and two or more charged point electrodes. In some aspects, the rotational disk assembly comprises an electrically insulating disk with its front face in conformal contact with a smaller electrically conducting disk and its back face in conformal contact with two or more charged point electrodes, as disclosed herein.

Fibrous Polymer Scaffold Membranes

In some embodiments, the polymer scaffold has the shape of a sheet or membrane. The individual fibers within the membrane can be diametrically aligned during electrospinning using a rotating disc as a collector, as disclosed herein. The individual fibers within a different layer of the membrane can be randomly oriented during electrospinning using a rotating disc as a collector.

In some embodiments, the polymer scaffold has the shape of a membrane and has diametrically patterned polymer fibers. The fibers within the membrane create a diametrical pattern by spanning across two edges and a convergence region of the membrane. Examples of diametrically patterned polymer fibers are depicted in FIG. 1.

In various aspects, the disclosure relates to multilayer fibrous scaffold membranes. In some embodiments, the scaffolds may comprise at least one biodegradable polymer, one or more salts and, optionally, one or more additives. In some embodiments, the membrane is a shape that is substantially planar or sheet-like, having at least one flat surface. In some embodiments, a scaffold membrane in the shape of a membrane can be of varying thickness, with a homogeneous or a heterogeneous structure and/or composition. In some embodiments, the membrane can be substantially planar or sheet-like with a curvature such that at least one surface is concave or convex.

In various aspects, the scaffold membranes can be used in tissue engineering to improve, regenerate or replace biological tissues. Diametrically patterned fibers within a scaffold membrane promote growth of tissues from the periphery toward the convergence region on the surface of the scaffold, thereby allowing the scaffold membranes to repair and/or replace a defect in a tissue of a subject. Analogously, non-diametrically aligned fibers promote the growth of tissues along the scaffold membranes in the direction of fiber alignment. In some embodiments, repairing and/or replacing a defect comprises contacting the scaffold membranes with the defect such that the scaffold membranes patch and/or cover all or any portion of a defect in a patient, thereby taking the place of at least some of the biological tissue that would otherwise be present in the defect. Scaffold membranes of the present disclosure can be used to repair and/or replace a defect when placed on top of a defect, below a defect, or within the physical boundaries of a defect. In some embodiments, scaffold membranes can repair and/or replace a defect when used as an onlay. In some embodiments, scaffold membranes can repair and/or replace a defect when sutured in place. In some embodiments, the convergence region of the diametrical fibers may be positioned in the center of the wound or defect such that new tissue growth is directed specifically toward the center of the wound or defect from all points on the periphery. In various embodiments, scaffold membranes of the present disclosure can completely or partially repair and/or replace a defect, at the option of the user.

Therefore, in several aspects, the fibrous scaffold membranes can be used medically to patch and/or regrow tissue in a subject, particularly in defect areas including, without limitation, surgical wounds, non-surgical wounds, biopsy defects, and areas of tissue damage or trauma.

Continuous Fibers in Individual Layers and Between Layers

As described herein, in certain embodiments, different layers of fibers can be constructed from the same fiber (continuous) or different fibers (discontinuous). In various embodiments, all of the layers of multilayer scaffolds are comprised of a single polymer fiber that is continuous between the layers. In various embodiments, all of the layers of multilayer scaffolds are comprised of two continuous polymer fibers. It will be understood that the total number of continuous polymer fibers that comprise the layers of the scaffolds can be increased or decreased as may be desired.

In some embodiments, the multilayer fibrous polymer scaffolds are constructed of a plurality of layers that collectively comprise a single, continuous polymer fiber. In other embodiments, the multilayer fibrous polymer scaffolds are constructed of a plurality of layers that collectively comprise at least two, at least three, at least four, or at least five continuous polymer fibers.

In some embodiments, the polymer fibers of a first layer of the scaffolds can be continuous with the polymer fibers of a second layer of the scaffolds. For example, if a two-layer scaffold created from a single polymer is desired, the polymer stream used to create the first layer can be used to create the second layer without stopping the flow of polymer from the spinneret, and thus both layers will be constructed with a single, continuous polymer fiber. In some embodiments, a two-layer scaffold is created from a single polymer, wherein the polymer stream used to create the first layer is used to create the second layer without stopping the flow of polymer from the spinneret, thus both layers are constructed from a single, continuous polymer fiber. In some embodiments, a two-layer scaffold is created from two polymers, wherein the polymer streams used to create the first layer are used to create the second layer without stopping the flow of the polymers from the spinnerets, thus both layers are constructed from two continuous polymer fibers. In some embodiments, a two-layer scaffold is created from three polymers, wherein the polymer streams used to create the first layer are used to create the second layer without stopping the flow of the polymers from the spinnerets, thus both layers are constructed from three continuous polymer fibers. In some embodiments, a two-layer scaffold is created from four polymers, wherein the polymer streams used to create the first layer are used to create the second layer without stopping the flow of the polymers from the spinnerets, thus both layers are constructed from four continuous polymer fibers. In some embodiments, a two-layer scaffold is created from five polymers, wherein the polymer streams used to create the first layer are used to create the second layer without stopping the flow of the polymers from the spinnerets, thus both layers are constructed from five continuous polymer fibers.

In various embodiments, the continuous layers of fibers may be formed of the same polymer solution. In various embodiments, the continuous layers of fibers may be formed of two or more different polymer solutions. A series of different polymer solutions can be sequentially fed through the same tube into the same electrospinner jet to create a continuous flow even while changing the composition of the solution used to spin fibers.

In some embodiments, the layers of fibers may be discontinuous. The discontinuity between fibrous layers may be achieved, for example, by: (i) pausing or stopping the process of fiber formation (i.e., solution flow and/or mandrel rotation) for an amount of time sufficient to break the trajectory of fiber-forming solution and/or cause solvent in the deposited layer to evaporate; and/or (ii) physically cutting or disturbing (i.e., putting objects in the pathway) the jet trajectory of fiber-forming solution with or without stopping the process (i.e., solution flow and/or mandrel rotation).

Non-continuously formed fibrous layers (in addition to continuously formed fibrous layers) may be associated with each other in various degrees depending upon the application desired. The fibrous layers may be randomly intertwined, non-covalently associated, chemically adhered, physically fused, etc. Thus, even though the fibrous layers can be formed in a non-continuous process of more than one electrospinning session, the layers can be made essentially integral.

Polymers, Additives, Salts

A variety of polymers from synthetic and/or natural sources can be used to compose the fibrous polymer scaffolds. A fiber can be made from a polymer comprising one monomer or subunit or from a polymer comprising a plurality of monomers or subunits. For example, lactic or polylactic acid or glycolic or polyglycolic acid can be utilized to form poly(lactide) (PLA) or poly(L-lactide) (PLLA) nanofibers or poly(glycolide) (PGA) nanofibers. Fibers can also be made from polymers comprising more than one monomer or subunit thus forming a co-polymer, terpolymer, etc. For example, lactic or polylactic acid and be combined with glycolic acid or polyglycolic acid to form the copolymer poly(lactide-co-glycolide) (PLGA). Other copolymers of use in the present disclosure include poly(ethylene-co-vinyl) alcohol.

The polymer(s) may be natural polymers, biological polymers, synthetic polymers, or a combination thereof. In various embodiments, the polymer fibers used to create the scaffolds of the present disclosure are selected from aliphatic polyesters, polyhydroxyalkanoates, polyurethanes, poly(ester urethane), poly(ether urethane), poly(trimethylene carbonate), poly(glycerol sebacate), poly(pyrrole), poly(acetylene), polyalkylene oxides, polydimethylsiloxane, polyvinylalcohol, polyvinylpyrrolidone, polylysine, collagen, gelatin, laminin, fibronectin, elastin, alginate, fibrin, hyaluronic acid, proteoglycans, polypeptides, polysaccharides, silk fibroin and combinations and copolymers thereof.

In some embodiments, a fiber comprises a single polymer or subunit which is a member selected from aliphatic polyesters, polyhydroxyalkanoates, polyurethanes, poly(ester urethane), poly(ether urethane), poly(trimethylene carbonate), poly(glycerol sebacate), poly(pyrrole), poly(acetylene), polyalkylene oxides, polydimethylsiloxane, polyvinylalcohol, polyvinylpyrrolidone, polylysine, collagen, gelatin, laminin, fibronectin, elastin, alginate, fibrin, hyaluronic acid, proteoglycans, polypeptides, polysaccharides and combinations and copolymers thereof.

In some embodiments, a fiber comprises two different polymers or subunits which are members selected from aliphatic polyesters, polyhydroxyalkanoates, polyurethanes, poly(ester urethane), poly(ether urethane), poly(trimethylene carbonate), poly(glycerol sebacate), poly(pyrrole), poly (acetylene), polyalkylene oxides, polydimethylsiloxane, polyvinylalcohol, polyvinylpyrrolidone, polylysine, collagen, gelatin, laminin, fibronectin, elastin, alginate, fibrin, hyaluronic acid, proteoglycans, polypeptides, polysaccharides, silk fibroin and combinations and copolymers thereof.

In some embodiments, a fiber comprises three different polymers or subunits which are members selected from aliphatic polyesters, polyhydroxyalkanoates, polyurethanes, poly(ester urethane), poly(ether urethane), poly(trimethylene carbonate), poly(glycerol sebacate), poly(pyrrole), poly (acetylene), polyalkylene oxides, polydimethylsiloxane, polyvinylalcohol, polyvinylpyrrolidone, polylysine, collagen, gelatin, laminin, fibronectin, elastin, alginate, fibrin, hyaluronic acid, proteoglycans, polypeptides, polysaccharides, silk fibroin and combinations and copolymers thereof.

In some embodiments, a fiber comprises four different polymers or subunits which are members selected from aliphatic polyesters, polyhydroxyalkanoates, polyurethanes, poly(ester urethane), poly(ether urethane), poly(trimethylene carbonate), poly(glycerol sebacate), poly(pyrrole), poly (acetylene), polyalkylene oxides, polydimethylsiloxane, polyvinylalcohol, polyvinylpyrrolidone, polylysine, collagen, gelatin, laminin, fibronectin, elastin, alginate, fibrin, hyaluronic acid, proteoglycans, polypeptides, polysaccharides, silk fibroin, and combinations and copolymers thereof.

In another embodiment, a fiber comprises five different polymers or subunits which are members selected from aliphatic polyesters, polyhydroxyalkanoates, polyurethanes, poly(ester urethane), poly(ether urethane), poly(trimethylene carbonate), poly(glycerol sebacate), poly(pyrrole), poly (acetylene), polyalkylene oxides, polydimethylsiloxane, polyvinylalcohol, polyvinylpyrrolidone, polylysine, collagen, gelatin, laminin, fibronectin, elastin, alginate, fibrin, hyaluronic acid, proteoglycans, polypeptides, polysaccharides, silk fibroin, and combinations and copolymers thereof.

The aliphatic polyester can be linear or branched. In some embodiments, the aliphatic polyester is linear and is selected from D-lactic acid, L-lactic acid, lactide, poly(lactic acid), poly(lactide)glycolic acid, poly(glycolic acid), poly(glycolide), glycolide, poly(lactide-co-glycolide), poly(lactic acid-co-glycolic acid), polycaprolactone and combinations thereof. In some embodiments, the aliphatic polyester is branched and is selected from D-lactic acid, L-lactic acid, lactide, poly(lactic acid), poly(lactide)glycolic acid, poly(glycolic acid), poly(glycolide), glycolide, poly(lactide-co-glycolide), poly(lactic acid-co-glycolic acid), polycaprolactone and combinations thereof. In some embodiments, the aliphatic polyester is conjugated to a linker or a biomolecule.

In some embodiments, the polyalkylene oxide is selected from polyethylene oxide, polyethylene glycol, polypropylene oxide, polypropylene glycol and combinations thereof.

The fibrous polymer scaffolds can comprise a fiber of at least one composition. In some embodiments, the fibrous polymer scaffolds comprise a number of different types of fibers selected from at least one fiber, at least two fibers, at least three fibers, at least four fibers, at least five fibers, at least six fibers, at least seven fibers, at least eight fibers, at least nine fibers and at least ten fibers.

In some embodiments, the fiber or fibers of the fibrous polymer scaffolds are biodegradable. In some embodiments, the fibers of the fibrous polymer scaffolds comprise biodegradable polymers. In some embodiments, the biodegradable polymers comprise a monomer which is a member selected from lactic acid and glycolic acid. In another embodiment, the biodegradable polymers are poly(lactic acid), poly(glycolic acid) or a copolymer thereof. In some embodiments, the biodegradable polymers are those which are approved by the FDA for clinical use, such as poly(lactic acid) and poly(glycolic acid).

In various aspects, scaffolds comprising biodegradable polymers can be used to guide the morphogenesis of tissue and/or to gradually degrade after the assembly of the tissue. The degradation rate of the polymers can be tailored by one of skill in the art to match the tissue generation rate. For example, if a polymer that biodegrades quickly is desired, a combination of approximately 50:50 polylactic acid to glycolic acid or polyglycolic acid can be selected to form the copolymer poly(lactide-co-glycolide). Additional ways to increase polymer biodegradability can involve selecting a hydrophilic copolymer (for example, polyethylene glycol), decreasing the molecular weight of the polymer, as higher molecular weight often means a slower degradation rate, and decreasing the fiber density in the scaffolds, as lower fiber density can lead to more water absorption and faster degradation.

The tissue can include, without limitation, abdominal wall, amniotic sac, bladder, blood vessels, brain, cardiac tissue, fascia, gingival tissue, intestine, ligaments, meningeal tissue, mucous membranes, muscle, nerves, skin, spinal cord, stomach, tendons, etc. In some embodiments, scaffolds comprising biodegradable polymers can be used to guide the morphogenesis of dura mater and gradually degrade after the assembly, repair or replacement of the dura mater.

In various embodiments, greater than 50%, greater than 60%, greater than 70%, greater than 80%, greater than 90%, greater than 91%, greater than 92%, greater than 93%, greater than 94%, greater than 95%, greater than 96%, greater than 97%, greater than 98%, or greater than 99% of a single layer of a scaffold is w/w comprised of at least one of the polymers described herein.

To improve flexibility and hydrophilic properties of the polymer fibers, an additive may be blended with the polymer. In various embodiments, the additive is present in the scaffold in an amount of from 0.1% to 10% of the total weight of the polymer. In various embodiments, the additive is present in the scaffold in an amount of from 1.0% to 2.0%, from 2.0% to 3.0%, from 3.0% to 4.0%, from 4.0% to 5.0%, from 5.0% to 6.0%, from 6.0% to 7.0%, from 7.0% to 8.0%, from 8.0% to 9.0%, or from 9.0% to 10.0% of the total weight of the polymer. In some embodiments, the additive is 3.1% of the total weight of the polymer. In some embodiments, the additive is 6.2% of the total weight of the polymer.

The additive can be a plasticizer including, but not limited to, triethyl citrate, poly(ethylene glycol), poly(propylene glycol), glycerol, and similar materials. In various embodiments, the plasticizer is present in the scaffold in an amount of from 0.1%-25% of the total weight of the polymer.

Poly(propylene glycol) can be used as a plasticizer for certain rigid polymers, including, without limitation, poly(L-lactide-co-caprolactone), it can also be used to increase water uptake into the scaffold and to allow for the formation of a thick layer of unaligned polymer fibers on top of another layer of polymer fibers, such as a diametrically aligned fiber layer. In some embodiments, the additive is poly(propylene glycol). In some embodiments, the additive is poly(propylene glycol) with an average molecular weight between 100-10,000. In some embodiments, the additive is poly(propylene glycol) with an average molecular weight between 100-1,000. In some embodiments, poly(propylene glycol) is blended with the polymer in an amount of from 0.01%-25% of the total weight of the polymer. In some embodiments, poly(propylene glycol) is blended with the polymer in an amount of from 0.01%-10% of the total weight of the polymer.

To improve electrospinning and to decrease the average diameter of the polymer fibers, a dopant may be added to the polymer solution. In various embodiments, the dopant is a salt. Salt produces an excess charge to facilitate the electrospinning process. Salts can include, for example, NaCl, $KH_2PO_4$, $K_2HPO_4$, $KIO_3$, KCl, $MgSO_4$, $MgCl_2$, $NaHCO_3$, $CaCl_2$, $NaCH_3COOH$, as well as salts of organic compounds including, for example, acetic acid, ascorbic acid, citric acid, lactic acid, glycolic acid, and mixtures thereof. In some embodiments, the salt is sodium acetate. In some embodiments, the salt is anhydrous sodium acetate.

In various embodiments, the fibers comprise a copolymer of L-lactide and epsilon-caprolactone, with molar ratios of L-lactide between 40%-90%, and molar ratios of epsilon-caprolactone between 10%-60%. For example, the fibers can comprise a copolymer of L-lactide and epsilon-caprolactone with molar ratios of L-lactide between 50%-80% and molar ratios of epsilon-caprolactone between 20%-50%. In an additional example, the fibers can comprise a copolymer of L-lactide and epsilon-caprolactone with molar ratios of L-lactide between 50%-70% and molar ratios of epsilon-caprolactone between 30%-50%.

In various embodiments, the fibers are formed from polymer solutions, wherein one or more polymers are dissolved in a solvent. In some embodiments, the polymer solution is at least 20% (weight/volume) of poly(L-lactide) dissolved in a solvent. In this embodiment, polymer fibers comprising 100 wt % poly(L-lactide) are formed upon electrospinning.

In some embodiments, the polymer solution is poly(L-lactide), glycerol and sodium acetate dissolved in hexafluoroisopropanol at weight/volume concentrations of wt %, 2 wt % and 0.2 wt %, respectively. In this embodiment, polymer fibers comprising 90 wt % poly(L-lactide are formed), 9 wt % glycerol and 1 wt % sodium acetate are formed upon electrospinning.

In some embodiments, the polymer solution is poly(L-lactide), triethyl citrate, and sodium acetate dissolved in hexafluoroisopropanol at weight/volume concentrations of wt %, 6 wt % and 0.2 wt %, respectively. In this embodiment, polymer fibers comprising 80.1 wt % poly(L-lactide), 19.2 wt % triethyl citrate and 0.7 wt % sodium acetate are formed upon electrospinning.

In some embodiments, the polymer solution is poly(L-lactide-co-caprolactone) (lactide:caprolactone molar ratio: 70:30), poly(propylene glycol) (MW: 425) and sodium acetate dissolved in hexafluoroisopropanol at weight/volume concentrations of 15 wt %, 1 wt % and 0.2 wt %, respectively. In this embodiment, polymer fibers comprising 93 wt % poly(L-lactide-co-caprolactone), 6 wt % poly(propylene glycol) and 1 wt % sodium acetate are formed upon electrospinning.

In some embodiments, the polymer solution is poly(DL-lactide-co-caprolactone)(lactide:caprolactone molar ratio: 85:15) and sodium acetate dissolved in hexafluoroisopropanol at weight/volume concentrations of 20 wt % and 0.2 wt %, respectively. In this embodiment, polymer fibers comprising 99 wt % poly(DL-lactide-co-caprolactone) and 1 wt % sodium acetate are formed upon electrospinning.

In some embodiments, the polymer solution is poly(L-lactide-co-caprolactone) (lactide:caprolactone molar ratio: 70:30) and sodium acetate dissolved in hexafluoroisopropanol at weight/volume concentrations of 15 wt % and 0.2 wt %, respectively. In this embodiment, polymer fibers comprising 99 wt % poly(L-lactide-co-caprolactone) and 1 wt % sodium acetate are formed upon electrospinning.

In some embodiments, the polymer solution is poly(L-lactide), poly(lactide-co-glycolide) and sodium acetate dissolved in hexafluoroisopropanol at weight/volume concentrations of 15 wt %, 15 wt % and 0.2 wt %, respectively. In this embodiment, polymer fibers comprising 49.7 wt % poly(1-lactide), 49.7 wt % poly(lactide-co-glycolide) and 0.6 wt % sodium acetate are formed upon electrospinning.

In some embodiments, the polymer solution is poly(L-lactide) and sodium acetate dissolved in hexafluoroisopropanol at weight/volume concentrations of 28 wt % and 0.2 wt %, respectively. In this embodiment, polymer fibers comprising 99.3 wt % poly(L-lactide) and 0.7 wt % sodium acetate are formed upon electrospinning.

In some embodiments, the polymer solution is poly(dioxanone) and sodium acetate dissolved in hexafluoroisopropanol at weight/volume concentrations of 10 wt % and 0.2 wt %, respectively. In this embodiment, polymer fibers comprising 98 wt % poly(dioxanone) and 2 wt % sodium acetate are formed upon electrospinning.

In some embodiments, the polymer solution is poly(dioxanone) dissolved in hexafluoroisopropanol at weight/volume concentration of 10 wt %. In this embodiment, polymer fibers comprising 100 wt % poly(dioxanone) are formed upon electrospinning.

In some embodiments, the polymer solution is collagen dissolved in hexafluoroisopropanol at weight/volume concentrations of 8 wt %. In this embodiment, polymer fibers comprising 100 wt % collagen are formed upon electrospinning.

In some embodiments, the polymer solution is poly(ethylene oxide) dissolved in 90% ethanol, 10% water at weight/volume concentration of 8 wt %. In this embodiment, polymer fibers composed of 100 wt % poly(ethylene oxide) are formed upon electrospinning.

In various embodiments, the polymer fibers of one or more layers of the scaffolds comprise one or more materials selected from an aliphatic polyester, a poly(alkylene) oxide, poly(L-lactic acid), 70/30 poly(L-lactide-co-caprolactone), poly(caprolactone), poly(DL-lactide-co-caprolactone), poly(lactide-co-glycolic acid), poly(vinylpyrrolidine), poly(dimethylsiloxane), poly(lysine), collagen, laminin, fibronectin, elastin, alginate, fibrin, hyaluronic acid, proteoglycans, polypeptides, silk fibroin, poly(urethanes), poly(ester urethanes), poly(ether urethanes), poly(trimethylene carbonate), poly(glycerol sebacate), poly(pyrrole), poly(acetylene), poly (ethylene-co-vinyl) alcohol, poly(vinyl) alcohol, poly(ethylene)glycol, poly(propylene)glycol, poly-L-lactide-co-glycolide-co-ε-caprolactone, poly(tetrafluoroethylene), poly(dioxanone), polyglactin 910, and/or combinations and copolymers thereof.

In various embodiments, the polymer fibers of one or more layers of the scaffolds comprise one or more materials selected from aliphatic polyesters, polyhydroxyalkanoates, polyurethanes, polyalkylene oxides, polydimethylsiloxane, polyvinylalcohol, polyvinylpyrrolidone, polylysine, collagen, gelatin, laminin, fibronectin, elastin, alginate, fibrin, hyaluronic acid, proteoglycans, polypeptides, polysaccharides and combinations thereof.

The aliphatic polyesters can be, for example, lactic acid (D- or L-), lactide, poly(lactic acid), poly(lactide)glycolic acid, poly(glycolic acid), poly(glycolide), glycolide, poly(lactide-co-glycolide), poly(lactic acid-co-glycolic acid), epsilon-caprolactone, poly(epsilon-caprolactone), and/or combinations and copolymers thereof.

The polyalkylene oxides can be, for example poly(ethylene) oxide, poly(propylene) oxide, and/or combinations thereof.

In some embodiments, the fibers of one or more layers of the scaffolds comprise one or more materials selected from poly(L-lactide-co-caprolactone), poly(L-lactic acid), and/or combinations thereof.

In some embodiments, the first layer of fibers and the second layer of fibers in a multilayer scaffold comprise a single continuous polymer fiber comprising poly(L-lactide-co-caprolactone) and poly(propylene glycol). In some embodiments the continuous polymer fiber also comprises sodium acetate. In some embodiments, the continuous fiber comprises 92.6% poly(L-lactide-co-caprolactone), 6.2% poly(propylene glycol) and 1.2% sodium acetate.

Poly(L-lactide-co-caprolactone) is a flexible elastomeric polymer. In various embodiments, poly(propylene glycol) is added to poly(L-lactide-co-caprolactone) as it serves to plasticize poly(L-lactide-co-caprolactone), to increase water uptake into the scaffold membrane, and it allows for the formation of a thicker unaligned fiber layer as a second layer, on top of a diametrically aligned fiber layer. Poly(L-lactic acid) is a rigid polymer. In various embodiments, poly(L-lactic acid) is used to provide structural integrity to a scaffold. In some embodiments, a combination of poly(L-lactide-co-caprolactone) polymer fibers and poly(L-lactic acid) polymer fibers is used to generate scaffolds as the use of poly(L-lactic acid) makes the scaffolds more rigid and less elastic than poly(L-lactide-co-caprolactone) with poly(propylene glycol) alone.

In some embodiments, the first layer of fibers and the second layer of fibers comprise two continuous polymer fibers, wherein one of the polymer fibers comprises poly(L-lactide-co-caprolactone), and the other polymer fiber comprises poly(L-lactic acid). In some embodiments, one of the two continuous fibers comprises 100% poly(L-lactide-co-caprolactone). In some embodiments, one of the two continuous fibers comprises 100% poly(L-lactic acid).

In some embodiments, the first layer of fibers and the second layer of fibers comprise a single continuous polymer fiber, wherein continuous fiber comprises poly(L-lactide-co-caprolactone), poly(propylene glycol) and sodium acetate. In some embodiments, the fiber comprises 92.6% poly(L-lactide-co-caprolactone), 6.2% poly(propylene glycol) and 1.2% sodium acetate.

In some embodiments, the first layer of fibers and the second layer of fibers comprise two continuous polymer fibers, wherein the first of the two continuous fibers comprises poly(L-lactide-co-caprolactone) and poly(propylene glycol), and the second of the two continuous fibers comprises poly(L-lactic acid). In some embodiments both fibers also comprise sodium acetate. In some embodiments, one of the two continuous fibers comprises 92.6% poly(L-lactide-co-caprolactone), 6.2% poly(propylene glycol) and 1.2% sodium acetate. In some embodiments, one the two continuous fibers comprises 98.7% poly(L-lactic acid) and 1.3% sodium acetate.

In some embodiments, the first layer of fibers and the second layer of fibers comprise two continuous polymer fibers, wherein the first of the two continuous fibers comprises poly(L-lactide-co-caprolactone) and poly(propylene glycol), and the second of the two continuous fibers comprises poly(glycolic acid). In some embodiments both fibers also comprise sodium acetate. In some embodiments, one of the two continuous fibers comprises 92.6% poly(L-lactide-co-caprolactone), 6.2% poly(propylene glycol) and 1.2% sodium acetate. In some embodiments, one of the two continuous fibers comprises greater than 98% poly(glycolic acid) and less than 2% sodium acetate.

Poly(L-lactide-co-caprolactone) is a flexible elastomeric polymer. In various embodiments, poly(propylene glycol) is added to poly(L-lactide-co-caprolactone) to plasticize poly(L-lactide-co-caprolactone), to increase water uptake into the scaffold membrane, and to generate a thicker unaligned fiber layer as a second layer of the scaffold, on top of a diametrically aligned fiber layer.

Poly(glycolic acid) is a rigid polymer. In various embodiments, poly(glycolic acid) is used to provide structural integrity to a scaffold and because it biodegrades quickly.

In some embodiments, a combination of polymer streams of poly(L-lactide-co-caprolactone) with poly(propylene glycol) and poly(glycolic acid) is used to generate scaffolds because the addition of poly(glycolic acid) may operate to make the scaffold more rigid and less elastic than poly(L-lactide-co-caprolactone) with poly(propylene glycol) alone. Additionally, poly(glycolic acid) has a faster rate of biodegradation than poly(L-lactide-co-caprolactone) or poly(L-lactic acid).

In some embodiments, the first layer of fibers and the second layer of fibers comprise two continuous polymer fibers, wherein the first of the two continuous fibers comprises poly(L-lactide-co-caprolactone) and poly(propylene glycol), and the second of the two continuous fibers comprises collagen. In some embodiments both fibers also comprise sodium acetate. In some embodiments, one of the two continuous fibers comprises 92.6% poly(L-lactide-co-caprolactone), 6.2% poly(propylene glycol) and 1.2% sodium acetate. In some embodiments, one of the two continuous fibers comprises greater than 98% collagen and less than 2% sodium acetate.

Collagen is a rigid polymer that is present in a large number of biological tissues. In some embodiments, collagen is used as one of a plurality of polymer fibers comprising the scaffolds to provide structural integrity and because it biodegrades quickly. Collagen also provides cell adhesion regions within the scaffolds.

In some embodiments, a combination of polymer streams of poly(L-lactide-co-caprolactone) with poly(propylene glycol) and collagen is used to generate scaffolds because the addition of collagen may make the scaffolds more rigid and less elastic than poly(L-lactide-co-caprolactone) with poly(propylene glycol) alone. Additionally, because collagen has a faster rate of biodegradation than poly(L-lactide-co-caprolactone), the rate of biodegradation can be tailored to suit several specific uses.

In various embodiments, two polymer streams can be used to generate the fibrous polymer scaffolds. In some embodiments, the two polymer streams comprise a first stream of poly(L-lactide-co-caprolactone) with poly(propylene glycol) and a second stream of poly(L-lactic acid), wherein the relative population of the two polymer fibers may be varied when creating a scaffold. In general, the higher the population of poly(L-lactic acid) fibers, the more rigid the scaffold will be. The higher the population of poly(L-lactide-co-caprolactone) with poly(propylene glycol) fibers, the more elastic the scaffold. In some embodiments, the relative population of the two polymer fibers is selected from: 50% poly(L-lactide-co-caprolactone) with poly(propylene glycol) and 50% poly(L-lactic acid); 90% poly(L-lactide-co-caprolactone) with poly(propylene glycol) and 10% poly(L-lactic acid); 80% poly(L-lactide-co-caprolactone) with poly(propylene glycol) and 20% poly(L-lactic acid); 70% poly(L-lactide-co-caprolactone) with poly(propylene glycol) and 30% poly(L-lactic acid); 60% poly(L-lactide-co-caprolactone) with poly(propylene glycol) and 40% poly(L-lactic acid); 40% poly(L-lactide-co-caprolactone) with poly(propylene glycol) and 60% poly(L-lactic acid); 30% poly(L-lactide-co-caprolactone) with poly(propylene glycol) and 70% poly(L-lactic acid); 20% poly(L-lactide-co-caprolactone) with poly(propylene glycol) and 80% poly(L-lactic acid); and 10% poly(L-lactide-co-caprolactone) with poly(propylene glycol) and 90% poly(L-lactic acid).

In some embodiments, the two polymer streams comprise a first stream of poly(L-lactide-co-caprolactone) with poly(propylene glycol) and a second stream of poly(glycolic acid), wherein the relative population of the two polymer fibers may be varied when creating a scaffold. In general, the higher the population of poly(glycolic acid) fibers, the more rigid the scaffold will be. Additionally, the biodegradation rate increases with an increase in the poly(glycolic acid) population. The higher the population of poly(L-lactide-co-caprolactone) with poly(propylene glycol) fibers, the more elastic the scaffold. In some embodiments, the relative population of the two polymer fibers is selected from: 50% poly(L-lactide-co-caprolactone) with poly(propylene glycol) and 50% poly(glycolic acid); 90% poly(L-lactide-co-caprolactone) with poly(propylene glycol) and 10% poly(glycolic acid); 80% poly(L-lactide-co-caprolactone) with poly(propylene glycol) and 20% poly(glycolic acid); 70% poly(L-lactide-co-caprolactone) with poly(propylene glycol) and 30% poly(glycolic acid); 60% poly(L-lactide-co-caprolactone) with poly(propylene glycol) and 40% poly(glycolic acid); 40% poly(L-lactide-co-caprolactone) with poly(propylene glycol) and 60% poly(glycolic acid), 30% poly(L-lactide-co-caprolactone) with poly(propylene glycol) and 70% poly(glycolic acid); 20% poly(L-lactide-co-caprolactone) with poly(propylene glycol) and 80% poly(glycolic acid); and 10% poly(L-lactide-co-caprolactone) with poly(propylene glycol) and 90% poly(glycolic acid).

In some embodiments, the two polymer streams comprise a first stream of poly(L-lactide-co-caprolactone) with poly(propylene glycol) and a second stream of collagen, wherein the relative population of the two polymer fibers may be varied when creating a scaffold. In general, the higher the population of collagen fibers, the more rigid the scaffold will be. Additionally, the biodegradation rate increases with an increase in the collagen population. The higher the population of poly(L-lactide-co-caprolactone) with poly(propylene glycol) fibers, the more elastic the scaffold. In some embodiments, the relative population of the two polymer fibers is selected from: 50% poly(L-lactide-co-caprolactone) with poly(propylene glycol) and 50% collagen; 90% poly(L-lactide-co-caprolactone) with poly(propylene glycol) and 10% collagen; 80% poly(L-lactide-co-caprolactone) with poly(propylene glycol) and 20% collagen; 70% poly(L-lactide-co-caprolactone) with poly(propylene glycol) and 30% collagen; 60% poly(L-lactide-co-caprolactone) with poly(propylene glycol) and 40% collagen; 40% poly(L-lactide-co-caprolactone) with poly(propylene glycol) and 60% collagen; 30% poly(L-lactide-co-caprolactone) with poly(propylene glycol) and 70% collagen; 20% poly(L-lactide-co-caprolactone) with poly(propylene glycol) and 80% collagen; and 10% poly(L-lactide-co-caprolactone) with poly(propylene glycol) and 90% collagen.

Plasma Treatment

It is known in the art that various chemical and physical properties of a substrate can be altered through surface exposure to plasma, an ionized gas consisting of positive ions and free electrons in proportions resulting in essentially no net electrical charge. Diametrically patterned fibrous polymer scaffolds may be treated with plasma to influence scaffold properties such as hydrophilicity/wettability, cell binding, attachment of biomolecules, adhesion to other polymers or substrates. Treating a scaffold with plasma can include, for example, placing the scaffold into contact with plasma for a period of time. The type and duration of the effects of plasma treatment depend on the type of gas used in plasma formation and the duration of scaffold exposure to the plasma.

In various embodiments, the type of gas used to create the plasma is selected without limitation from oxygen, hydrogen, nitrogen, helium, argon, freon, neon, air, nitrous oxide, carbon dioxide and combinations thereof.

In various embodiments, the plasma treatment lasts for a duration selected from greater than 1 s, greater than 2 s, greater than 3 s, greater than 4 s, greater than 5 s, greater than 10 s, greater than 15 s, greater than 30 s, greater than 45 s, greater than 60 s, greater than 2 min, greater than 5 min, greater than 10 min, greater than 20 min, greater than 30 min, or greater than 60 min. In some embodiments, the scaffold is exposed to plasma for a duration selected from less than 60 min, less than 30 min, less than 20 min, less than 10 min, less than 5 min, less than 2 min, less than 60 s, less than 45 s, less than 30 s, less than 15 s, less than 10 s, less than 5 s, less than 4 s, less than 3 s, less than 2 s, or less than 1 s. In some embodiments, the scaffold is exposed to plasma for a duration of 60 s.

In various embodiments, fibrous polymer scaffolds made from naturally hydrophobic polymers may be treated with plasma in order to increase hydrophilicity/wettability. In one embodiment, a diametrically patterned fibrous polymer scaffold comprising poly(L-lactide-co-caprolactone) and poly(propylene glycol) is exposed to oxygen plasma in order to increase hydrophilicity/wettability.

In various embodiments, all surfaces of the fibrous polymer scaffold may be exposed to the plasma treatment. In various embodiments, select surfaces may be exposed to the plasma treatment while others are blocked or masked from treatment. In one embodiment, the first layer of fibrous polymer membrane is directly exposed to plasma treatment while the last layer is blocked from plasma treatment through close contact with a masking surface, thereby resulting in different final properties for first layer and the last layer in a single scaffold.

In various embodiments, the plasma treatment may be applied after the complete fibrous scaffold has been formed. In various embodiments, the plasma treatment may be applied in between the formation of two discrete layers. In various embodiments, more than one plasma treatment may be applied at various points during the creation of the scaffold.

Dimensions

The fibrous polymer scaffolds of the disclosure can have a variety of dimensions which can be varied to suit the needs of a particular application. In various embodiments, the scaffolds are nanofiber polymer scaffolds. Nanofiber polymer scaffolds have submicron-scale features, with each layer comprising polymer fibers having an average fiber diameter of, for example, between 10 nm and 1,000 nm and/or between 50 nm and 1,000 nm. In various embodiments, nanofiber polymer scaffolds can resemble the physical structure at the area of treatment, such as native collagen fibrils or other extracellular matrices.

In various embodiments, the scaffolds are microfiber polymer scaffolds. Microfiber polymer scaffolds have micron-scale features, with each layer comprising polymer fibers having an average fiber diameter of, for example, between 1,000 nm and 50,000 nm and/or between 1,000 nm and 20,000 nm. In various embodiments, microfiber polymer scaffolds can resemble the physical structure at the area of treatment, such as native collagen fibrils or other extracellular matrices.

The layers of fibers within a single scaffold may have the same thickness and/or composition with respect to one another. For some embodiments, the thickness and/or composition may be varied within a single layer.

The fiber diameters can vary both between and within layers. In some embodiments, the fiber diameters can vary from 1 nm-10,000 nm. In some embodiments, the fiber diameters can vary from 100 nm-2000 nm. Different fiber diameters may be desirable for different applications. In formulating a desired fiber diameter, one should consider whether any components (i.e., drugs, growth factors, differentiation factors, etc.) will be seeded between fibers and/or the size of any cells expected to be attracted to and deposited along the fibers in vivo.

In some embodiments, the scaffold membranes have a diameter selected from greater than 1 cm, greater than 2 cm, greater than 3 cm, greater than 4 cm, greater than 5 cm, greater than 6 cm, greater than 7 cm, greater than 8 cm, greater than 9 cm, greater than 10 cm, greater than 11 cm, greater than 12 cm, greater than 13 cm, greater than 14 cm, greater than 15 cm, greater than 16 cm, greater than 17 cm, greater than 18 cm, greater than 19 cm, greater than 20 cm, greater than 21 cm, greater than 22 cm, greater than 23 cm, greater than 24 cm, greater than 25 cm, greater than 26 cm, greater than 27 cm, greater than 28 cm, greater than 29 cm, or greater than 30 cm. In some embodiments, the scaffold membranes have a diameter selected from less than 30 cm, less than 29 cm, less than 28 cm, less than 27 cm, less than 26 cm, less than 25 cm, less than 24 cm, less than 23 cm, less than 22 cm, less than 21 cm, less than 20 cm, less than 19 cm, less than 18 cm, less than 17 cm, less than 16 cm, less than 15 cm, less than 14 cm, less than 13 cm, less than 12 cm, less than 11 cm, less than 10 cm, less than 9 cm, less than 8 cm, less than 7 cm, less than 6 cm, less than 5 cm, less than 4 cm, less than 3 cm, less than 2 cm, or less than 1 cm.

The thickness of the layers of the scaffolds can vary from layer to layer. In various embodiments, the first layer of the scaffolds comprises diametrically aligned fibers and is thinner than a second layer of the scaffolds, which can comprise aligned or unaligned fibers.

The thickness or diameter of the polymer fibers can be varied from layer to layer within a single scaffold by controlling several factors. For example, fiber diameter may be decreased by: (i) adding more salt to the polymer solution; (ii) using a more polar solvent in the polymer solution; (iii) increasing the distance between the spinneret(s) and the mandrel; (iv) increasing the voltage; (v) increasing the concentration of the polymer solution; (vi) decreasing the flow rate of the polymer solution; and (vii) increasing the spin rate of the mandrel. See, e.g., U.S. Patent Application Publication No. 2007/0269481 at paragraphs [0027], [0030], [0127], [0139], [0162], [0165], [0176], and [0179].

In some embodiments, the diameter of the fibers comprising a fibrous polymer scaffold ranges from 1 nm-10,000 nm. In some embodiments, the average diameter of the fibers comprising a fibrous polymer scaffold ranges from 500 nm-1,000 nm. In various embodiments, the average diameter of the fibers is within the range of 10 nm-1,000 nm.

In some embodiments, the average diameter of the fiber or fibers comprising a single layer of a multilayer fibrous polymer scaffold is within a range selected from: 100 nm to 10 microns; 1,000 nm to 20,000 nm; 10 nm to 1,000 nm; 2,000 nm to 10,000 nm; 0.5 nm to 100 nm; 0.5 nm to 50 nm; 1 nm to 35 nm; 2 nm to 25 nm; 90 nm to about 1,000 nm; and 500 nm to 1,000 nm.

In various embodiments, greater than 50%, greater than 60%, greater than 70%, greater than 80%, greater than 90%, greater than 91%, greater than 92%, greater than 93%, greater than 94%, greater than 95%, greater than 96%, greater than 97%, greater than 98%, or greater than 99% of the fibers in a single layer of a scaffold have the same average diameter.

The dimensions of each of the fibrous layers comprising a scaffold can be controlled. In some embodiments, the first layer of a fibrous polymer scaffold comprises diametrically aligned polymer fibers and has a thickness ranging from 1 micron to 70 microns. In various embodiments, each layer of a multilayer polymer scaffold has a thickness selected from: greater than 1 micron; greater than 20 microns; greater than 30 microns; greater than 40 microns; greater than 50 microns; greater than 60 microns; greater than 70 microns; greater than 80 microns; greater than 90 microns; greater than 100 microns; greater than 120 microns; greater than 140 microns; greater than 160 microns; greater than 180 microns; greater than 200 microns; greater than 220 microns; greater than 240 microns; greater than 260 microns; greater than 280 microns; and greater than 300 microns.

In various embodiments, the first layer of a multilayer polymer scaffold comprises diametrically aligned fibers and has an average thickness selected from: less than 600 microns; less than 580 microns; less than 560 microns; less than 540 microns; less than 520 microns; less than 500 microns; less than 480 microns; less than 460 microns; less than 440 microns; less than 420 microns; less than 400 microns; less than 380 microns; less than 360 microns; less than 340 microns; less than 330 microns; less than 320 microns; less than 300 microns; less than 280 microns; less than 260 microns; less than 240 microns; less than 220 microns; less than 200 microns; less than 180 microns; less than 160 microns; less than 140 microns; less than 120 microns; less than 100 microns; less than 90 microns; less than 80 microns; less than 70 microns; less than 60 microns; less than 50 microns; less than 40 microns; less than 30 microns; and less than 20 microns.

In various embodiments, the total thickness of the entire fibrous polymer scaffold is selected from: greater than 20 microns; greater than 40 microns; greater than 60 microns; greater than 80 microns; greater than 100 microns; greater than 120 microns; greater than 140 microns; greater than 160 microns; greater than 180 microns; greater than 200 microns; greater than 220 microns; greater than 240 microns; greater than 260 microns; greater than 280 microns; greater than 300 microns; greater than 320 microns; greater than 340 microns; greater than 360 microns; greater than 380 microns; greater than 400 microns; greater than 420 microns; greater than 440 microns; greater than 460 microns; greater than 480 microns; greater than 500 microns; greater than 520 microns; greater than 540 microns; greater than 560 microns; greater than 580 microns; and greater than 600 microns.

Therapeutic Uses

The fibrous polymer scaffolds can be used in any manner known in the art. These uses can include, without limitation, uses as tissue substitutes and/or tissue regeneration matrices for wounds and/or defects in biological tissues including, without limitation, abdominal wall, amniotic sac, bladder, blood vessels, brain, cardiac tissue, fascia, gingival tissue, intestine, ligaments, meningeal tissue, mucous membranes, muscle, nerves, skin, spinal cord, stomach, tendons, etc., uses in combination with cells, uses in combination with biomolecules, and uses in combination with pharmaceutically acceptable excipients, as described in PCT Publication No. WO 2007/090102. Similarly, uses in compositions, and as grafts for nerves, skin, vascular tissue, and muscle may be used as described in PCT Publication No. WO 2007/090102.

A diametrically aligned layer of polymer fibers can affect cell alignment, cell migration and cellular function. Diametrically aligned polymer fibers can induce and direct cell migration along the direction of the fiber orientation, thus enhancing tissue regeneration in such a direction.

The diametrically aligned polymer fibers function by first promoting directed outgrowth of tissue in contact with the diametrically aligned fibers and second by continuously guiding the regenerating tissue in the direction of the axis or axes of alignment of the diametrically aligned fibers. Therefore, when placed in contact with a wound or defect, a layer of diametrically patterned polymer fibers promotes healing by promoting directed outgrowth of tissue in contact with the diametrically aligned fibers at the periphery of the wound or defect and by continuously guiding the regenerating tissue across the wound or defect gap along the direction of alignment of the diametrically aligned fibers toward the convergence region of the scaffold, which can be positioned at the center of the tissue defect or at any other desired location.

Therefore, diametrically patterned polymer fibers can be used to help regenerate a variety of tissues including, without limitation, abdominal wall, amniotic sac, bladder, blood vessels, brain, cardiac tissue, fascia, gingival tissue, intestine, ligaments, meningeal tissue, mucous membranes, muscle, nerves, skin, spinal cord, stomach, tendons, etc. For example, the diametrically patterned layer of a multilayer fibrous polymer scaffold can enhance and specifically direct the growth of biological tissue from the entire periphery toward the center of a tissue defect. In some embodiments, the scaffolds can be used in this manner to promote rapid cell and/or tissue coverage within a wound or defect area.

The scaffolds can be sized to completely cover, or to partially cover, a wound or defect gap in a tissue. In some embodiments, the scaffolds are cut or trimmed into a desired shape and sized to completely cover, or to partially cover, a wound or defect. In various embodiments, the scaffolds are used to patched large tissue defects. In some embodiments, defect to be patched can have a length selected from greater than 1 cm, greater than 2 cm, greater than 3 cm, greater than 4 cm, greater than 5 cm, greater than 6 cm, greater than 7 cm, greater than 8 cm, greater than 9 cm, greater than 10 cm, greater than 15 cm, greater than 20 cm, greater than 25 cm, greater than 30 cm. In some embodiments, defect gaps to be bridged can have a length selected from less than 30 cm, less than 25 cm, less than 20 cm, less than 15 cm, less than 10 cm, less than 9 cm, less than 8 cm, less than 7 cm, less than 6 cm, less than 5 cm, less than 4 cm, less than 3 cm, less than 2 cm, or less than 1 cm.

In some embodiments, defects to be patched can have a width selected from greater than 1 cm, greater than 2 cm, greater than 3 cm, greater than 4 cm, greater than 5 cm, greater than 6 cm, greater than 7 cm, greater than 8 cm, greater than 9 cm, greater than 10 cm, greater than 15 cm, greater than 20 cm, greater than 25 cm, or greater than 30 cm. In some embodiments, defect gaps to be bridged can have a width selected from less than 30 cm, less than 25 cm, less than 20 cm, less than 15 cm, less than 10 cm, less than 9 cm, less than 8 cm, less than 7 cm, less than 6 cm, less than 5 cm, less than 4 cm, less than 3 cm, less than 2 cm, or less than 1 cm.

In some embodiments, defects to be patched can have a diameter selected from greater than 1 cm, greater than 2 cm, greater than 3 cm, greater than 4 cm, greater than 5 cm, greater than 6 cm, greater than 7 cm, greater than 8 cm, greater than 9 cm, greater than 10 cm, greater than 15 cm, greater than 20 cm, greater than 25 cm, or greater than 30 cm. In some embodiments, defect gaps to be bridged can have a width selected from less than 30 cm, less than 25 cm, less than 20 cm, less than 15 cm, less than 10 cm, less than 9 cm, less than 8 cm, less than 7 cm, less than 6 cm, less than 5 cm, less than 4 cm, less than 3 cm, less than 2 cm, or less than 1 cm.

The wound or defect area can be asymmetrical, having a long axis and a short axis. In various embodiments, the layer of diametrically patterned fibers within a scaffold can be contacted with an asymmetrical wound or defect such that the convergence region of the scaffold is positioned at the center of the wound or defect area to promote rapid cell ingrowth and coverage of the defect or wound from the entire periphery toward the center.

In several aspects, diametrically patterned fibrous polymer scaffolds can be contacted with a subject to replace, regenerate or improve a biological function and/or a biological tissue. In some embodiments, the scaffolds replace, regenerate or improve the structure and/or function of a biological tissue, wherein the biological tissue is selected from abdominal wall, amniotic sac, bladder, blood vessels, brain, cardiac tissue, fascia, gingival tissue, intestine, ligaments, meningeal tissue, mucous membranes, muscle, nerves, skin, spinal cord, stomach, tendons, and other biological tissues in a subject.

In several aspects, the present disclosure provides methods of treating an injury or defect in a subject, the methods comprising contacting the subject with a therapeutically effective amount of the scaffolds of the disclosure, sufficient to treat the injury or defect. A therapeutically effective amount is an amount of contact between a scaffold and a subject sufficient to provide the desired local or systemic effect or to affect the desired therapeutic result. In some embodiments, the subject is contacted with one or more scaffolds at the site of the injury or defect. In some embodiments, the defect or injury is selected from wounds, defects arising due to disease, defects arising due to infection, surgical incisions and/or biopsies; the foregoing can include, without limitation, a severed meninx, a damaged meninx, severed fascia, damaged fascia, a severed nerve, a damaged nerve, a severed muscle, a damaged muscle, a severed blood vessel, a damaged blood vessel, a skin wound and bruised skin.

In several aspects, the present disclosure provides methods of growing tissue in a subject, the methods comprising contacting the subject with a therapeutically effective amount of a scaffold disclosed herein, sufficient to facilitate growth of the tissue. In some embodiments, the tissue is a biologically-simple connective tissue having a sheet-like architecture. In some embodiments, the tissue is a member selected from meninx tissue, fascia, skin tissue, cardiac tissue, gastrointestinal tissue, stomach tissue, tissue of the abdominal wall, muscle tissue, vascular tissue, nerve tissue, and similar tissues. In some embodiments, the tissue is a biological tissue selected from abdominal wall, amniotic sac, bladder, blood vessels, brain, cardiac tissue, fascia, gingival tissue, intestine, ligaments, meningeal tissue, mucous membranes, muscle, nerves, skin, spinal cord, stomach, tendons, and other biological tissues.

In several aspects, the present disclosure provides methods of treating an injury or defect in a subject, the methods comprising contacting the defect or injury in a subject with a fibrous polymer scaffold such that the scaffold at least partially replaces the defect or injury. The scaffolds of the present disclosure can be used in vitro or in vivo to test for their efficacy.

Scaffolds are suitable for use with a variety of subjects. In some embodiments, the subject is an animal. In some embodiments, the animal is selected from a human, a dog, a cat, a horse, a rat and a mouse.

In several aspects, diametrically aligned layers of polymer fibers comprise biodegradable polymers. These layers can be used to guide the morphogenesis of tissue types having anisotropic structure, e.g., biological tissues such as nerve, skin, blood vessel, skeletal muscle, cardiac muscle, tendon and ligament. These diametrically aligned layers can also be used in the development of three-dimensional tissue constructs. Using the scaffolds described herein, three-dimensional constructs of nerve tissue, spinal cord tissue, skin tissue, vascular tissue, muscle tissue, and many other tissues can be created.

Diametrically patterned fibrous polymer scaffolds of the present disclosure have numerous characteristics that are useful in wound healing. For example, the scaffolds can be both nano-porous and breathable, thus preventing microbes and infectious particles from crossing through to the wound or defect, while allowing air flow and moisture penetration, which are important to natural wound healing. Additionally, in some embodiments the polymer fibers comprising the scaffolds are biodegradable, which allows for temporary wound coverage followed by eventual ingrowth of new tissue.

The materials comprising the scaffolds can be varied to approximate the characteristics of natural tissue including, for example, mechanical strength, rate of degradation, and rate of tissue regeneration.

The scaffolds of the present disclosure are useful for clinical and personal wound care and soft tissue regeneration. In some embodiments, a diametrically patterned fibrous polymer scaffold can be used as a wound dressing or as a graft to treat external skin wounds. In a clinical setting, the scaffolds can be used to treat wounds resulting from trauma, burns, ulcers, abrasions, lacerations, surgery, or other damage or trauma. A user can use the scaffolds to cover and protect the wound area, to temporarily replace lost or damaged skin tissue, and to guide new tissue generation and wound healing into the damaged area. The scaffolds can be used as an onlay, or may be secured to the wound area using sutures, adhesives, or overlaying bandages. The scaffolds may be cut to match the size of the wound, or may overlap the wound edges.

The scaffolds may be tailored for personal/home care by combining the scaffold with an adhesive to create a diametrically patterned fibrous polymer scaffold bandage. The adhesive can serve to hold the scaffold in place on a wound or defect area and can be removed when the fibers degrade or fuse with the tissue. The scaffolds may be secured with any suitable adhesive including, for example, liquid or gel adhesives.

Large sized scaffolds can be used as gauze to absorb fluid and protect large wounds or defects. When used in this manner, the scaffolds can be wrapped around a wounded area, secured with tape, or with secondary bandages.

The scaffolds can be used to treat internal soft tissue wounds or defects in biological tissues including, without limitation, the amniotic sac, ulcers in the gastrointestinal tract or mucous membranes, gingival damage or recession, internal surgical incisions or biopsies, etc. The scaffolds can be used as an onlay or may be sutured or adhered into place to fill or cover the damaged tissue area. The nano-scale architecture of nanofibrous scaffolds closely mimics the architecture of the extracellular matrix of many common soft tissues. For example, nano-scale polymer fibers are structurally similar to collagen fibrils found in skin and other tissues. This architecture may prevent scar formation in a wound or defect by providing an organized, diametrically aligned layer of a scaffold for cells to migrate into a wound.

Diametrically patterned polymer fibers in the scaffolds can be used to keep cells aligned and organized during regrowth into the defect or wound area, rather than allowing them to arrange randomly. Random arrangement of cells typically results in the formation of scar tissue and thus the scaffolds may be used to minimize the formation of scar tissue.

In several embodiments, a molecule is covalently attached, either directly or through a linker, to the fibrous polymer scaffolds, and the molecule is capable of either covalently or non-covalently attaching to a member selected from an extracellular matrix component, a growth factor, a differentiation factor and combinations thereof. In some embodiments, the molecule is covalently attached to the scaffold through a linker, and the linker is selected from di-amino poly(ethylene glycol), poly(ethylene glycol) and combinations thereof. The molecule can be structural or alternatively can be related to a tissue. In some embodiments, the extracellular matrix component is selected from laminin, collagen, fibronectin, elastin, vitronectin, fibrinogen, polylysine and combinations thereof. In some embodiments, the growth factor is selected from acidic fibroblast growth factor, basic fibroblast growth factor, nerve growth factor, brain-derived neurotrophic factor, insulin-like growth factor, platelet derived growth factor, transforming growth factor beta, vascular endothelial growth factor, epidermal growth factor, keratinocyte growth factor and combinations thereof. In some embodiments, the differentiation factor is selected from stromal cell derived factor, sonic hedgehog, bone morphogenic proteins, notch ligands, Wnt and combinations thereof. Molecules can also be incorporated with the scaffolds either during electrospinning or post-fabrication. The molecules can be incorporated via blending, direct covalent attachment, attachment through various linkers, or by adsorption. In some embodiments, the molecules are organic molecules typically made by living organisms. In some embodiments, the molecules are selected from nucleotides, amino acids, sugars, fatty acids, steroids, nucleic acids, polypeptides, peptides, peptide fragments, carbohydrates, lipids, and combinations thereof (e.g., glycoproteins, ribonucleoproteins, lipoproteins, or the like). In some embodiments, the molecules are selected from receptor molecules, extracellular matrix components or biochemical factors. Biochemical factors can include, for example, growth factors or differentiation factors. In some embodiments, the molecule is selected from glycosaminoglycans and proteoglycans.

The following are examples of certain specific uses of the scaffolds of the disclosure and are not intended to be limiting. Rather, the present disclosure is intended to include uses of the disclosed polymer scaffolds with a plurality of biological tissues including, without limitation, abdominal wall, amniotic sac, bladder, blood vessels, brain, cardiac tissue, fascia, gingival tissue, intestine, ligaments, meningeal tissue, mucous membranes, muscle, nerves, skin, spinal cord, stomach, tendons, etc.

Uses Involving Meninges

In some embodiments, the scaffolds are used to repair, regenerate and/or replace a severed or damaged meninx, or one or more severed or damaged meninges. One use is for the regeneration of damaged dura mater. The dura mater is a membrane that surrounds the brain and spinal cord. It is the outermost of the three meninges, which help protect the brain and spinal cord and provide a retention barrier for the cerebrospinal fluid. In a normal subject, the dura mater is attached directly to the skull, or to the bones of the vertebral canal in the spinal cord. Damage to the dura mater can be caused by trauma, surgical incisions, subdural hematoma, epidural hematoma, meningitis, meningiomas, tumor involvement, etc. The tissue of the dura mater is capable of repair and/or regeneration but it is unable to do so efficiently over large gaps or defects.

The scaffolds described herein can serve as replacements for all known dural graft matrices, such as xenogeneic collagen-based dural graft substitutes, which are currently a popular form of treatment for dura mater defects.

In some embodiments, the scaffolds may be used to repair the dura mater at one or more locations where it is damaged or otherwise contains a defect and is no longer in continuity. The scaffolds may be used in all situations involving discontinuous and/or damaged dura mater. In some embodiments, the scaffolds are used where the defect gap is large enough to either greatly hinder or prevent direct regeneration of the dura mater. In some embodiments, the scaffolds are contacted with a defect gap in the dura mater and at least partially bridge the defect gap to enhance and direct the regeneration of dura mater into the defect gap.

In some embodiments, the scaffolds are placed and/or contacted with a defect gap such that a single layer of a scaffold, comprising diametrically patterned polymer fibers, contacts the defect site and the remaining layers of the scaffold do not contact the defect. In some embodiments, the diametrically patterned fibers in contact with the defect promote rapid cell and tissue growth from the entire periphery toward the center of the defect and/or toward the convergence region of the scaffold. Rapid cell and tissue coverage of the defect helps lower the risk for complications such as cerebrospinal fluid leakage, neural tissue adhesions and infections.

In various embodiments, the scaffolds are used as an onlay either on top of, or underneath, the dura mater to bridge the wound or defect. In some embodiments, the scaffolds are inserted directly into the wound or defect. In some embodiments, the scaffolds are put in contact with a wound or defect so that a layer of diametrically aligned fibers contacts the wound or defect. In some embodiments, the scaffolds are sutured in place.

In various embodiments, the polymer content of the scaffolds is adjusted to match the architecture and physical properties of the dura mater. Dura mater is composed mainly of collagen and elastic fibers embedded in an amorphous extracellular substance. Various studies have observed the tensile strength of human cranial and spinal dura mater as being between 6-20 MPa (see, e.g., J. Neurosurg. 86:1012-1017 (1997); J. Biomech. Eng. 4:541-544 (1998); and Anesth. Analg. 88:1317-21 (1999)). The dura mater is also characterized as being tough, inelastic and flexible. In some embodiments, the scaffolds are created to have the tensile strength, elasticity and flexibility similar to that of human dura mater by comprising at least two continuous polymer fibers, wherein the first of the two continuous fibers comprises poly(L-lactide-co-caprolactone) plus poly(propylene glycol) the second of the two continuous fibers comprises poly(L-lactic acid), and both fibers further comprise sodium acetate. In some embodiments, the scaffolds are created to have the tensile strength and flexibility similar to that of human dura mater by comprising at least two continuous polymer fibers, wherein both of the continuous fibers comprise poly(L-lactide-co-caprolactone) plus poly(propylene glycol) and sodium acetate.

Uses Involving Fascia

In some embodiments, the scaffolds are used to repair, regenerate and/or replace severed or damaged fascia. One use is for the regeneration of damaged abdominal fascia. Fascia comprises both superficial fascia and deep fascia. In a normal subject, superficial fascia surrounds organs, glands and neurovascular bundles, fills otherwise unoccupied space in the subject's body and can serve to store fat and water, can serve as a passageway for lymph, nerve and blood vessels, and can act as a protective padding. In a normal subject, deep fascia interpenetrates and surrounds the muscles, bones, nerves and blood vessels of the body where it serves to protect and insulate these structures. Damage to the fascia can be caused by trauma, surgical incisions, tumor involvement, etc. The tissue of fascia is capable of repair and/or regeneration but it is unable to do so efficiently over large gaps or defects.

The scaffolds described herein can serve as a replacement for all known means of fascia repair including surgical sutures, which are currently a popular form of treatment for fascia defects but are far from perfect.

In some embodiments, the scaffolds may be used to repair fascia at one or more locations where it is damaged or otherwise contains a defect and is no longer in continuity. The scaffolds may be used in all situations involving discontinuous and/or damaged fascia. In some embodiments, the scaffolds are used where the defect gap is large enough to either greatly hinder or prevent direct regeneration of fascia. In some embodiments, the scaffolds are contacted with a defect gap in fascia and at least partially bridge the defect gap to enhance and direct the regeneration of fascia into the defect gap.

In some embodiments, the scaffolds are placed and/or contacted with a defect gap such that a single layer of a scaffold, comprising diametrically patterned polymer fibers, contacts the defect site and the remaining layers of the scaffold do not contact the defect. In some embodiments, the diametrically patterned fibers in contact with the fascia defect promote rapid cell and fascia tissue growth from the entire periphery toward the center of the defect and/or toward the convergence region of the scaffold. Rapid cell and fascia tissue coverage of the defect helps lower the risk for complications such as infections, hernias and tissue adhesions.

In various embodiments, the scaffolds are used as an onlay either on top of, or underneath, the fascia in order to bridge the wound or defect. In some embodiments, the scaffolds are inserted directly into the wound or defect. In some embodiments, the scaffolds are put in contact with a wound or defect so that a layer of diametrically aligned fibers contacts the wound or defect. In some embodiments, the scaffolds are sutured in place.

In various embodiments, the polymer content of the scaffolds is adjusted to match the architecture and physical properties of fascia. Fascia is composed mainly of collagen and the amount of elastin fibers included in the fascia determines the level of extensibility and resilience the fascia will have. Other collagen-rich soft tissues, such as tendons, ligaments, and skin, display mechanical properties that strongly depend on the collagen fiber quantity and orientation. Accordingly, the mechanical properties of fascia can correlate to the underlying dense collagen structure. The observed elastic spring constant for collagen in humans is generally about 3.7 GPa-about 4.0 GPa. In some embodiments, the polymer content of the scaffolds is adjusted to closely match an elastic spring constant of about 3.7 GPa-about 4.0 GPa. In some embodiments, the polymer content of the scaffolds is adjusted to closely match the physical properties of collagen. In some embodiments, the physical properties of collagen may be matched in a scaffold that comprises at least two continuous polymer fibers, wherein the first of the two continuous fibers comprises poly(L-lactide-co-caprolactone) plus poly(propylene glycol) the second of the two continuous fibers comprises poly(L-lactic acid), and both fibers further comprise sodium acetate. In some embodiments, the physical properties of collagen may be matched in a scaffold that comprises at least one continuous polymer fiber, wherein the continuous fiber comprises poly(L-lactide-co-caprolactone) plus poly(propylene glycol) and sodium acetate.

Uses Involving Skin

In some embodiments, the scaffolds are used to repair, regenerate and/or replace damaged skin. One use is for the regeneration of damaged skin. The skin is the outer covering of the body of an animal. The skin is the largest organ of the integumentary system and is made up of epidermal and dermal tissue layers. Damage to the skin can be caused by trauma, burns, surgical incisions, tumor involvement, etc. The skin is capable of repair and/or regeneration but it is unable to do so efficiently over large gaps or defects without creating scar tissue.

The scaffolds described herein can serve as a replacement for all known means of skin repair including, without limitation, surgical sutures or stitches, adhesive bandages, gauze bandages, and synthetic skin replacements, each of which are currently popular forms of treatment for skin defects but are far from perfect.

In some embodiments, the scaffolds may be used to repair skin at one or more locations where it is damaged or otherwise contains a defect and is no longer in continuity. The scaffolds may be used in all situations involving discontinuous and/or damaged skin. In some embodiments, the scaffolds are used where the defect gap is large enough to either greatly hinder or prevent direct regeneration of skin without the generation of scar tissue. In some embodiments, the scaffolds are contacted with a defect gap in skin and at least partially bridge the defect gap to enhance and direct the regeneration of the skin into the defect gap.

In some embodiments, the scaffolds are placed and/or contacted with a defect gap such that a single layer of a scaffold, comprising diametrically patterned polymer fibers, contacts the defect site and the remaining layers of the scaffold do not contact the defect. In some embodiments, the diametrically patterned fibers in contact with the defect promote rapid cell and tissue growth from the entire periphery toward the center of the defect and/or toward the convergence region of the scaffold. Rapid cell and tissue coverage of the defect helps lower the risk for complications such as infections.

In various embodiments, the scaffolds are used as an onlay either on top of, or underneath, the skin in order to bridge the wound or defect. In some embodiments, the scaffolds are inserted directly into the wound or defect. In some embodiments, the scaffolds are put in contact with a wound or defect so that a layer of diametrically aligned fibers contacts the wound or defect. In some embodiments, the scaffolds are sutured in place. In some embodiments, the scaffolds are held in place via the use of secondary bandages. In some embodiments, the scaffolds are held in place by adhesives.

In various embodiments, the polymer content of the scaffolds is adjusted to match the architecture and physical properties of the skin. The underlying structure of skin is composed primarily of collagen. Other collagen-rich soft tissues, such as tendons and ligaments, display mechanical properties that strongly depend on the collagen fiber quantity and orientation. Accordingly, the mechanical properties of skin can correlate to the underlying collagen structure. The observed elastic spring constant for collagen in humans is generally about 3.7 GPa-about 4.0 GPa. In some embodiments, the polymer content of the scaffolds is adjusted to closely match an elastic spring constant of about 3.7 GPa-about 4.0 GPa. In some embodiments, the polymer content of the scaffolds is adjusted to closely match the physical properties of skin. In some embodiments, the physical properties of skin may be matched in a scaffold that comprises at least two continuous polymer fibers, wherein the first of the two continuous fibers comprises poly(L-lactide-co-caprolactone) plus poly(propylene glycol) the second of the two continuous fibers comprises poly(L-lactic acid), and both fibers further comprise sodium acetate. In some embodiments, the physical properties of skin may be matched in a scaffold that comprises at least one continuous polymer fiber, wherein the continuous fiber comprises poly(L-lactide-co-caprolactone) plus poly(propylene glycol) and sodium acetate.

Uses Involving Cardiac Tissue

In some embodiments, the scaffolds are used to repair, regenerate and/or replace damaged cardiac tissue. One use is for the regeneration of damaged cardiac tissue. Cardiac tissue is primarily a highly oxidative, striated muscle tissue composed of cardiac myocytes. Damage to cardiac tissue can be caused by trauma, surgical incisions, tumor involvement, myocardial infarction, coronary heart disease, cardiomyopathy, ischemic heart disease, etc. Cardiac tissue is capable of repair and/or regeneration but it is unable to do so efficiently over large gaps or defects.

The scaffolds described herein can serve as a replacement for known means of cardiac tissue repair including surgical sutures, which are currently a popular form of treatment for defects of cardiac tissue but are far from perfect.

In some embodiments, the scaffolds may be used to repair cardiac tissue at one or more locations where it is damaged or otherwise contains a defect and is no longer in continuity. The scaffolds may be used in all situations involving discontinuous and/or damaged cardiac tissue. In some embodiments, the scaffolds are used where the defect gap is large enough to either greatly hinder or prevent direct regeneration of cardiac tissue. In some embodiments, the scaffolds are contacted with a defect gap in cardiac tissue and at least partially bridge the defect gap and enhance and direct the regeneration of cardiac tissue into the defect gap.

In some embodiments, the scaffolds are placed and/or contacted with a defect gap such that a single layer of a scaffold, comprising diametrically patterned polymer fibers, contacts the defect site and the remaining layers of the scaffold do not contact the defect. In some embodiments, the diametrically patterned fibers in contact with the defect promote rapid cell and tissue growth from the entire periphery toward the center of the defect and/or toward the convergence region of the scaffold.

In various embodiments, the scaffolds are used as an onlay either on top of, or underneath, the cardiac tissue in order to bridge the wound or defect. In some embodiments, the scaffolds are inserted directly into the wound or defect. In some embodiments, the scaffolds are put in contact with a wound or defect so that a layer of diametrically aligned fibers contacts the wound or defect. In some embodiments, the scaffolds are sutured in place.

In various embodiments, the polymer content of the scaffolds is adjusted to match the architecture and physical properties of cardiac tissue. Cardiac tissue is composed mainly of the proteins actin and myosin. Accordingly, the mechanical properties of cardiac tissue can correlate to the average properties of both actin and myosin. The observed elastic modulus of the lateral wall of the myocardium has been shown to be about 3.40 kPa-3.78 kPa. In some embodiments, the polymer content of the scaffolds can be adjusted to closely match an elastic modulus of about 3.40 kPa-3.78 kPa. In some embodiments, the polymer content of the scaffolds can be adjusted to closely match the physical properties of cardiac tissue. In some embodiments, the physical properties of cardiac tissue may be matched in a scaffold that comprises at least two continuous polymer fibers, wherein the first of the two continuous fibers comprises poly(L-lactide-co-caprolactone) plus poly(propylene glycol) the second of the two continuous fibers comprises poly(L-lactic acid), and both fibers further comprise sodium acetate. In some embodiments, the physical properties of cardiac tissue may be matched in a scaffold that comprises at least one continuous polymer fiber, wherein the continuous fiber comprises poly(L-lactide-co-caprolactone) plus poly(propylene glycol) and sodium acetate.

Implantation of the Scaffolds

In various aspects, methods of implanting fibrous polymer scaffolds are provided. The scaffolds may be implanted into a subject according to any method known in the art. These methods include, without limitation, implantation by topical application (e.g. non-invasive implantation such as by placing a scaffold on the surface of the skin), onlay implantation, sutured implantation, and other methods. In various embodiments, the scaffolds can be implanted using the methods described in Zerris, et al., "Repair of the Dura Mater With Processed Collagen Devices", *Journal of Biomedical Materials Research Part B: Applied Biomaterials*, published online 26 Apr. 2007 in Wiley InterScience (www.interscience.wiley.com). DOI: 10.1002/jbm.b.30831. In various embodiments, the scaffolds can be implanted using the methods described in Mello et al., "Duraplasty with biosynthetic cellulose: An experimental study", *J. Neurosurg.*, 86: 143-150 (1997).

In some embodiments, methods of implanting scaffolds comprise contacting a wound, injury or defect in a tissue of a subject with a scaffold. In some embodiments, methods of implanting scaffolds comprise contacting a wound, injury or defect in a tissue of a subject with a single layer of a fibrous polymer scaffold. In some embodiments, the polymer fibers comprising the layer in contact with the wound, injury or defect are diametrically aligned. In some embodiments, the scaffold in contact with the wound, injury or defect at least partially replaces the defect. In some embodiments, the scaffold in contact with the wound, injury or defect completely replaces the defect.

In various embodiments, methods of implanting scaffolds comprise contacting a wound, injury or defect with one or more scaffolds in an amount, and under conditions, sufficient to treat the injury. In some embodiments, the amount of scaffolds is the amount necessary to at least partially replace the wound, injury or defect. In some embodiments, the amount of scaffolds is the amount necessary to completely replace the wound, injury or defect. In some embodiments, the conditions comprise contacting at least one layer of diametrically aligned fibers with the wound, injury or defect in order to allow the diametrically aligned fibers to provide specific guidance cues that direct regenerating tissue efficiently along the diametrically aligned layer and into/across the wound, injury or defect.

In various embodiments, the layer that contacts the wound, injury or defect comprises diametrically patterned polymer fibers. In some embodiments, the convergence region of the diametrically patterned layer is positioned over the center of the tissue wound or defect. In some embodiments, the layer that contacts the wound, injury or defect is the first layer of a scaffold membrane.

The wound, injury or defect can be wounds of any type, injuries of any type, surgical incisions, biopsies, etc.

In some embodiments, contacting a wound, injury or defect with a scaffold comprises placing the scaffolds over the defect. In some embodiments, contacting a wound, injury or defect with a scaffold comprises placing the scaffolds completely within the boundaries of the wound, injury or defect. In some embodiments, contacting a wound, injury or defect with a scaffold comprises placing the scaffolds underneath the defect wound, injury or defect.

In various embodiments, the method also comprises securing the scaffolds in place. In some embodiments, securing the scaffolds in place comprises suturing the scaffolds in place. In some embodiments, the scaffolds are placed on top of the wound, injury or defect and sutured into place. In some embodiments, the scaffolds are placed underneath the wound, injury or defect and sutured into place. In some embodiments, the scaffolds are placed within the boundaries of the wound, injury or defect and sutured into place.

In some embodiments, methods of implanting the scaffolds to repair or replace a defect in a meninx are provided. In some embodiments, the scaffolds are implanted into a subject to repair a defect in the dura mater. In some embodiments, the defect is created by an injury or disease. In some embodiments, the defect in the dura mater is surgically created. In some embodiments, the method comprises exposing the dura mater by performing any number of standard surgical methods including, without limitation, frontotemporoparietal craniotomy. In some embodiments, a portion of the exposed dura mater is excised and removed to surgically create a defect in the dura mater.

In some embodiments, the methods comprise contacting the defect in the dura mater with one or more scaffolds. In some embodiments, the contacting comprises contacting the defect with a layer of diametrically patterned polymer fibers. In some embodiments, the contacting comprises using the scaffold to completely cover the dural defect. In some embodiments, the contacting comprises using the scaffold to partially cover the dural defect. In some embodiments, the convergence region of the diametrically patterned layer of fibers is positioned over the center of the dural wound or defect.

In some embodiments, the methods comprise contacting the dural defect with a scaffold, wherein the scaffold is placed on top of the defect, superficial to the dura mater. In some embodiments, the methods comprise contacting the dural defect with a scaffold, wherein the scaffold is placed underneath the defect, deep to the dura mater. In some embodiments, the methods comprise contacting the dural defect with a scaffold, wherein the scaffold is placed within the boundaries of the defect, on the same plane as the dura mater.

In some embodiments, the methods comprise completely covering the dural defect with a scaffold and suturing the scaffold in place. In some embodiments, the methods comprise partially covering the dural defect with a scaffold and suturing the scaffold in place. In some embodiments, the methods comprise placing the scaffold within the boundaries of the dural defect and suturing the scaffold in place. In some embodiments, the methods comprise placing the scaffold underneath the dural defect and suturing the scaffold in place.

Kits Including the Scaffolds

In various embodiments, the fibrous polymer scaffolds described herein can be included as part of a kit. These kits can comprise, inter alia, instructions, such as in the form of an instruction manual, that teach methods of the disclosure and/or that describe the use of the scaffolds as components of the kit. In some embodiments, the kits comprise at least one scaffold and instructions for using the scaffold. In some embodiments, the kits comprise at least one scaffold and instructions for implanting the scaffold in the brain of a subject. In some embodiments, the kit comprises at least one scaffold and instructions for implanting the scaffold in the spinal cord of a subject. In some embodiments, the kits comprise at least one scaffold and instructions for using the scaffold to repair or replace damaged dura mater. In some embodiments, the kits comprise at least one scaffold membrane and instructions for using the scaffold membrane.

In some embodiments, the kits indicate that the diametrically aligned fibers of a layer of the scaffolds can function by promoting directed outgrowth of tissue located at the periphery of a damaged or defective area and in contact with the diametrically aligned layer of the scaffolds, and by continuously guiding regenerating tissue into/across the damaged or defective area in the direction of the diametrically aligned fibers of the first layer and toward the center of the defect until the damage or defect is healed.

In some embodiments, the kits comprise at least one scaffold and instructions for using the scaffold to repair wounds, injuries or defects by promoting the regeneration of anatomical biological components. The anatomical biological components can include, without limitation, abdominal wall, amniotic sac, bladder, blood vessels, brain, cardiac tissue, fascia, gingival tissue, intestine, ligaments, meningeal tissue, mucous membranes, muscle, nerves, skin, spinal cord, stomach and tendons.

The kits can include instructions for using the scaffolds in situations where one or more biological components or tissues are damaged or otherwise contain a defect and are no longer in continuity. In some embodiments, the kits indicate that the scaffolds can be used where the damage or defect is large enough to either greatly hinder or prevent direct regeneration of a biological component or tissue. In some embodiments, the kit indicates that the scaffolds can at least partially bridge the damage or defect and enhance and direct the regeneration of the biological component or tissue into/across the damage or defect.

In some embodiments, the kits indicate that a damaged or defective area of a biological component or tissue can be contacted with the scaffolds such that a layer of the scaffolds containing diametrically patterned polymer fibers contacts the damaged or defective site and the remaining layers of the scaffolds do not contact the damaged or defective area. In some embodiments, the kits can indicate that the convergence region of the diametrically patterned fiber layer can be positioned over the center of the wound defect to direct tissue growth from the periphery toward the center of the defect.

In some embodiments, the kits comprise at least one scaffold membrane and indications that the scaffold membrane is sided, in that the scaffold has one side comprising diametrically patterned fibers and another side comprising randomly oriented fibers. In some embodiments, the instructions include directions for placing a diametrically aligned layer of fibers present in the scaffold membrane in contact with a tissue. In some embodiments, the instructions include directions for placing a diametrically aligned layer of fibers present in a scaffold membrane in contact with a tissue and positioning the convergence region of the scaffold membrane over the center of the tissue defect. In some embodiments, the tissue is meningeal tissue.

In various embodiments, the kits indicate that the scaffolds can be shaped and sized by the user to match the specific requirements of the subject's wound, injury or defect. In some embodiments, the kit includes scaffold membranes that are largely circular in shape and indicates that the scaffolds may be sized to completely cover, or to partially cover, the subject's wound, injury or defect. In various embodiments, the kit indicates that the scaffolds can be used to patch large wounds, injuries or defects.

In some embodiments, the kit indicates that the wounds, injuries or defects to be patched can have a length selected from greater than 1 cm, greater than 2 cm, greater than 3 cm, greater than 4 cm, greater than 5 cm, greater than 6 cm, greater than 7 cm, greater than 8 cm, greater than 9 cm, greater than 10 cm, greater than 15 cm, greater than 20 cm, greater than 25 cm, greater than 30 cm. In some embodiments, the kit indicates that the wounds, injuries or defects to be patched can have a length selected from less than 30 cm, less than 25 cm, less than 20 cm, less than 15 cm, less than 10 cm, less than 9 cm, less than 8 cm, less than 7 cm, less than 6 cm, less than 5 cm, less than 4 cm, less than 3 cm, less than 2 cm, or less than 1 cm.

In some embodiments, the kit indicates that the wounds, injuries or defects to be patched can have a width selected from greater than 1 cm, greater than 2 cm, greater than 3 cm, greater than 4 cm, greater than 5 cm, greater than 6 cm, greater than 7 cm, greater than 8 cm, greater than 9 cm, greater than 10 cm, greater than 15 cm, greater than 20 cm, greater than 25 cm, greater than 30 cm. In some embodiments, the kit indicates that the wounds, injuries or defects to be bridged can have a width selected from less than 30 cm, less than 25 cm, less than 20 cm, less than 15 cm, less than 10 cm, less than 9 cm, less than 8 cm, less than 7 cm, less than 6 cm, less than 5 cm, less than 4 cm, less than 3 cm, less than 2 cm, or less than 1 cm.

In some embodiments, the kit indicates that the wounds, injuries or defects to be patched can have a diameter selected from greater than 1 cm, greater than 2 cm, greater than 3 cm, greater than 4 cm, greater than 5 cm, greater than 6 cm, greater than 7 cm, greater than 8 cm, greater than 9 cm, greater than 10 cm, greater than 15 cm, greater than 20 cm, greater than 25 cm, greater than 30 cm. In some embodiments, the kit indicates that the wounds, injuries or defects to be bridged can have a diameter selected from less than 30 cm, less than 25 cm, less than 20 cm, less than 15 cm, less than 10 cm, less than 9 cm, less than 8 cm, less than 7 cm, less than 6 cm, less than 5 cm, less than 4 cm, less than 3 cm, less than 2 cm, or less than 1 cm.

In various embodiments, the kits indicate that the scaffolds described herein can be used as an onlay either on top of, or underneath, a wound, injury or defect. In some embodiments, the kits indicate that the scaffolds can be placed within the boundaries of a wound, injury or defect. In some embodiments, the kits indicate that the scaffolds can be placed within the boundaries of discontinuous tissue to bridge a wound, injury or defect gap. In some embodiments, the kits indicate that the scaffolds can be sutured in place.

In some embodiments, the scaffolds in the kits are marked so as to allow a user to differentiate between a side comprising diametrically patterned polymer fibers and a side comprising unaligned polymer fibers.

In some embodiments, the scaffolds described herein are included as a component of a kit to be used to replace or repair a severed or damaged meninx, or one or more severed or damaged meninges. In some embodiments, the kit is for use in the regeneration of damaged dura mater in the brain of a subject. The kits can comprise, inter alia, an instruction manual that teaches the use of the scaffolds of the disclosure in the regeneration of the dura mater of the brain.

In some embodiments, the kit is for use in the regeneration of damaged dura mater in the spine or spinal cord of a subject. The kits can comprise, inter alia, an instruction manual that teaches the use of the scaffolds of the disclosure in the regeneration of the dura mater of the spine or spinal cord.

In some embodiments, the scaffolds described herein are included as a component of a kit to be used to replace or repair severed or damaged fascia. In some embodiments, the kit is for use in the regeneration of damaged fascia in a subject. These kits can comprise, inter alia, an instruction manual that teaches the use of the scaffolds of the disclosure in the regeneration of the fascia.

In some embodiments, the scaffolds described herein are included as a component of a kit to be used to replace or repair severed or damaged skin. In some embodiments, the kit is for use in the regeneration of damaged skin in a subject. These kits can comprise, inter alia, an instruction manual that teaches the use of the scaffolds of the disclosure in the regeneration of the skin.

In some embodiments, the scaffolds described herein are included as a component of a kit to be used to replace or repair severed or damaged cardiac tissue. In some embodiments, the kit is for use in the regeneration of damaged cardiac tissue in a subject. These kits can comprise, inter alia, an instruction manual that teaches the use of the scaffolds of the disclosure in the regeneration of the cardiac tissue.

Creation of Fibrous Polymer Scaffolds

Rotational Assemblies

The present disclosure provides technology that adapts the electrospinning process to directly fabricate fibrous polymer scaffolds wherein at least one layer comprises diametrically patterned fibers. In various embodiments, the fibers can be formed by using the electrospinning apparatus and motor assemblies as described in International Patent Publication No. WO 2007/090102. In various embodiments, the fibers can be formed using the electrospinning apparatus and assemblies described in U.S. Non-Provisional patent application Ser. No. 12/575,432.

Figure 2:
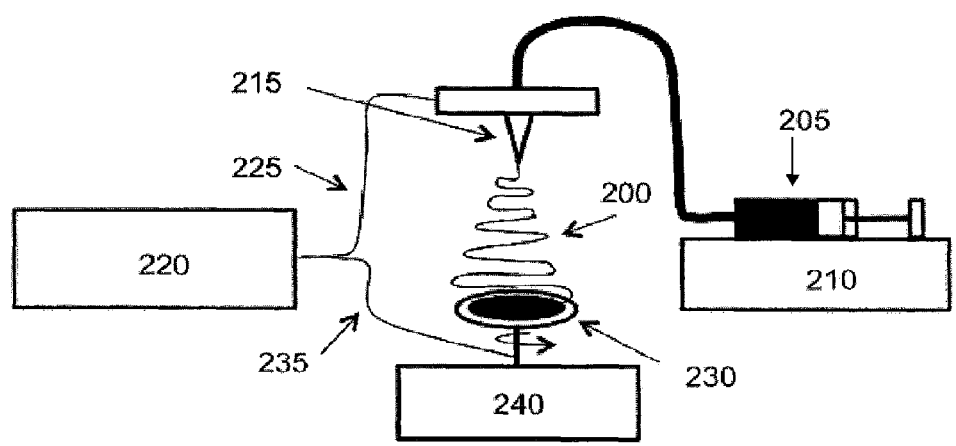
FIG. 2 depicts an electrospinning assembly with a rotational disk collector according to the present disclosure.

An electrospinning apparatus is shown in FIG. 2, which depicts an electrospinning apparatus capable of producing the fibrous polymer scaffolds described herein. A polymer solution, which contains polymer dissolved in a solvent, is contained within a syringe assembly 205. The syringe assembly 205 is part of a syringe pump 210 assembly in which a computer controls the rate at which the polymer solution exits the syringe 205 by controlling pressure or flow rate. Optionally, different flow rates can be provided and controlled to selected spinnerets 215. The flow rate can be changed to suit the desired physical characteristics of the polymer scaffolds, i.e., membrane thickness, layer thickness, fiber diameter, etc. The syringe pump 210 assembly feeds the polymer solution to a syringe needle, also referred to as a spinneret 215, that sits on a platform. The spinneret 215 has a tip geometry which allows for jet formation and transportation of the polymer stream 200, without interference. An electrical charge of magnitude ranging from about 10 kV to about 30 kV is applied to the spinneret 215 by a high voltage power supply 220 through a wire 225.

The spinneret 215 is positioned such that a jet of polymer solution 200 is directed towards a rotating collecting disk 230. The disk 230 is electrically charged with a polarity opposite that of the spinneret 215 at a magnitude ranging from about 1 kV to about 10 kV such that an electric field is created between the charged spinneret 215 and the collecting disk 230. Alternatively, the disk 230 may be electrically grounded rather than oppositely charged. The electric field causes a jet of the polymer solution 200 to be ejected from the spinneret 215 and spray toward the collecting disk 230, forming micro- or nanometer diameter polymer fibers that deposit on the surface of the disk 230.

The collecting disk 230 is attached to a drill chuck in the frame of the electrospinner via a connecting mandrel on the back of the disk, and the drill chuck is connected either to a high voltage power supply 220 or to electrical ground via a wire 235. The drill chuck is also attached to a non-conducting bearing, and the entire collector assembly (non-conducting bearing, drill chuck, and collecting disk 230) is connected to a motor 240. The motor 240 is linked to a speed control which controls the rate at which the motor spins the collector assembly. Optionally, different spin rates can be provided. The spin rate may be changed to suit the desired physical characteristics of the polymer scaffolds, i.e., membrane thickness, layer thickness, fiber diameter, etc.

During the electrospinning process, the spinneret 215 can be optionally traversed parallel to the surface of the collecting disk 230. The traversing motion of the spinneret 215 can be specifically controlled to produce specific amounts of fiber deposition at various points or regions on the collecting disk 230. The traversing motion can also be used to increase the overall area of fiber deposition on the collecting disk.

The alignment of the fibers depositing on the collector is directly influenced by the arrangement, geometries, and electrical charges of the various elements within the electrospinning area, including the needle platform, the collector itself and other nearby components. Using a disk collector of uniform geometry and electrical charge (as in FIG. 3A), and an electrospinning area that is free from additional electrical charges, the fibers in the electric field are free to whip in all directions, thereby depositing on the disk with random alignment. To obtain nanofibers or nanofiber layers having more complex types of alignment, such as diametrical alignment, more complex electrospinning assemblies may be employed.

Multi-Component Rotational Assemblies and Fibrous Scaffolds

In various embodiments, a multi-component rotational disk assembly device is disclosed that can provide diametrical alignment of fibers.

Figure 3:
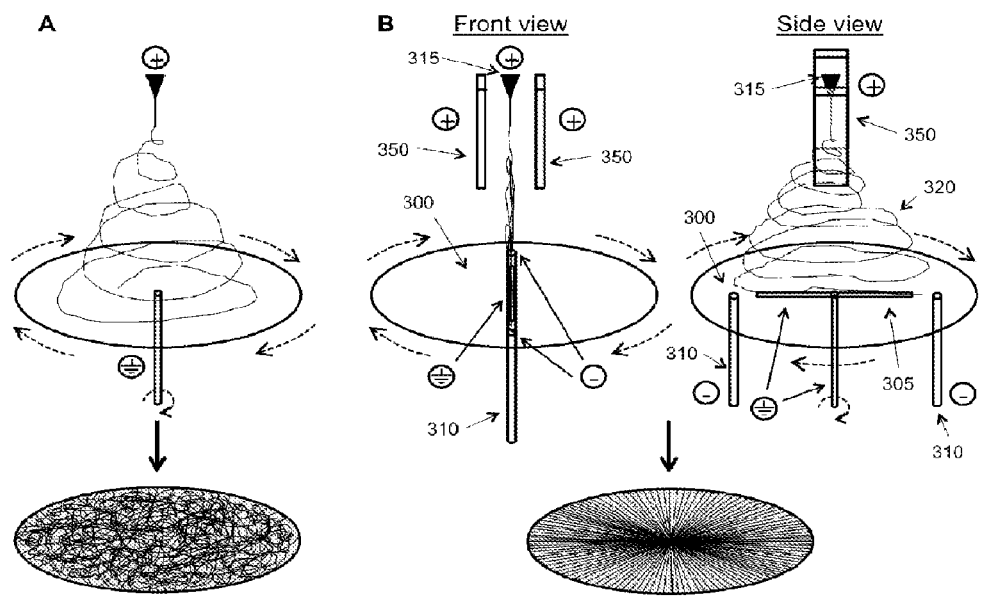
FIG. 3A is a simple disk rotational assembly for collecting a first layer of unaligned polymer fibers produced by an electrospinning process according to the present disclosure. A resulting unaligned nanofiber membrane is also depicted.
FIG. 3B depicts a front view and a side view of another rotational disk assembly for collecting a first layer of diametrically patterned nanofibers produced by an electrospinning process according to the present disclosure. The process incorporates electrically charged conductive arms near the spinneret to restrict lateral whipping of the nanofiber and also uses electrically charged or grounded conductive components in contact with the back of the collecting disk to guide diametrical nanofiber deposition.

To produce diametrically patterned fibers, additional components can be added to the rotating disk electrospinning assembly. An example of a multi-component disk assembly is depicted in FIG. 3B. The collector 300 comprises a thin, electrically-insulating circular disk positioned in front of three electrically conductive elements: one rectangular strip 305 in the center and two flanking mandrels 310 positioned a set distance away from each end of the strip.

The conductive components in the electrospinning setup can be electrically charged as depicted in FIG. 3B: the spinneret 315 can be positively charged, the mandrels 310 can be negatively charged, and the strip 305 can be grounded. The multi-component collector assembly can be used to create both a first layer of diametrically aligned fibers and one or more subsequent layers of differentially (i.e., unaligned) fibers without changing any electrospinning conditions. After electrospinning a first layer of diametrically aligned fibers, a time delay can be used in which a critical density of the diametrically aligned fibers covers the region over the conductive strip 305, after which unaligned fibers can be deposited.

In various embodiments, the two outer electrically conducting mandrels 310 and the center conducting strip 305 can be constructed of any conductive material, such as stainless steel. The two outer mandrels 310 can be grounded or charged. The center strip 305 can be charged, grounded, or a floating potential. An electrically insulating material is used for the disk 300 in front of the conducting components. In various embodiments the electrically insulating material may be nylon, polyurethane, polyvinylidene fluoride (PVDF), polyaryletheretherketone (PEEK), polytetrafluoroethylene (PTFE) or Teflon™ (various fluoropolymers), or poly(vinyl chloride) (PVC). If polymer material is used for the insulating regions, it can have varying thickness to customize the insulating properties.

The dimensions of the various components in the collector assembly may vary to accommodate the desired nanofiber deposition. Component conditions that may be altered include, without limitation: the diameter of the conducting mandrels 310, the length of the conducting strip 305, the spacing between the strip 305 and the mandrels 310, and the diameter of the insulating disk 300.

In various aspects, during operation, the multi-component disk assembly is rotated around its central axis and the outer mandrels 310 are electrically charged oppositely to the polymer solution 320 being released from the spinneret 315. For example, the polymer solution 320/spinneret 315 may be positively charged, and the outer mandrels 310 negatively charged. Alternatively, the polymer solution 320/spinneret 315 may be negatively charged and the outer mandrels 310 positively charged. Alternatively, the outer mandrels 310 may be grounded.

With reference to FIG. 3B, diametrically aligned fibers deposit across the length of the conductive strip 305 spanning between the conducting mandrels 310. The fibers form an arc spanning between the points of the two conducting mandrels 310. The arcing fibers have the opposite charge to mandrels 310. The arcing fibers lose their charge shortly after deposition and settle onto the disk 300 across the center strip 305 in a diametrically aligned manner. There is thus a constant deposition of arcing fibers and a constant settling of diametrical fibers onto the collecting disk 300 during electrospinning. Eventually, as the depositing fibers form a layer of increasing electrical insulation on the collector 300, the fibers no longer arc between the conducting mandrels 310. The diametrically aligned fibers thus form on the surface of the insulating disk 300 between the conducting mandrels 310 and over the conducting strip 305.

Figure 4:
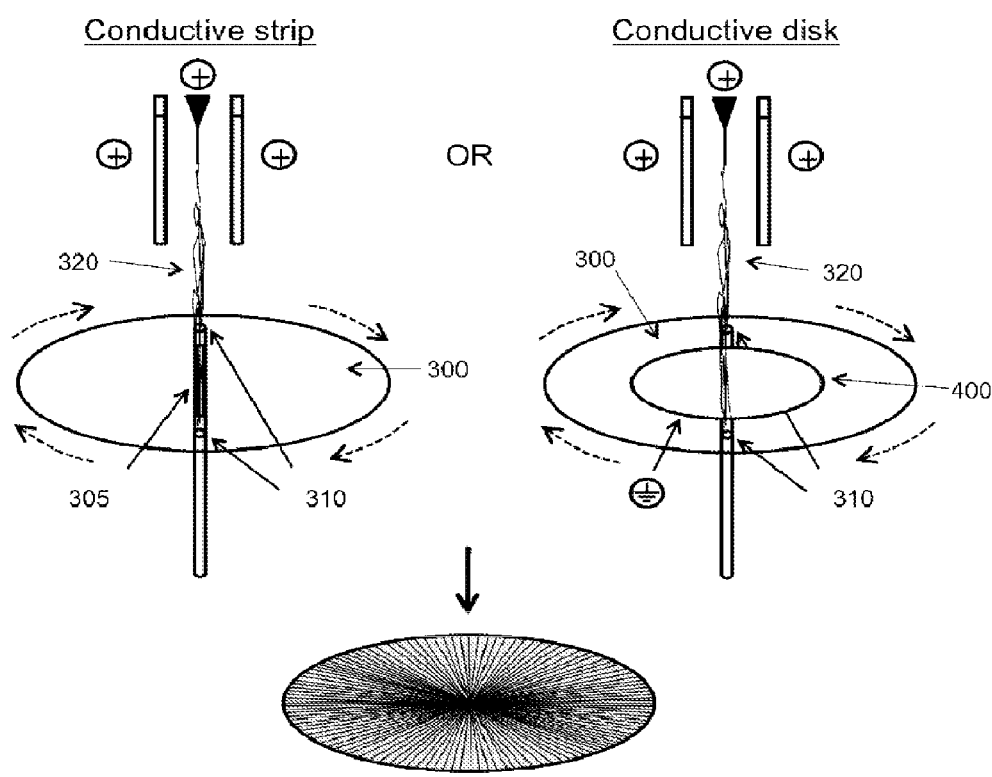
FIG. 4 depicts another rotational disk assembly for collecting a first layer of diametrically patterned nanofibers according to the present disclosure. The figure shows that, in certain embodiments, a grounded conductive element may either be a thin conductive strip located behind the rotating disk or a conductive circular disk element affixed to the front of the large rotating disk.

Alternatively, the strip 305 behind the insulating disk 300 can be replaced with a conductive disk 400 centered on the front of the insulating disk 300 as depicted in FIG. 4 and the polymer solution 320 produces fibers having comparable diametrical alignment. Like the strip 305, the disk 400 can be constructed of any conductive material, such as stainless steel. The dimensions (i.e., diameter) of the disk 400 may be adjusted to suit the desired size of the deposition area and resulting scaffold. The depositing diametrical fibers span between the conducting mandrels 310 and deposit across the diameter of the conductive disk 400.

Figure 5:
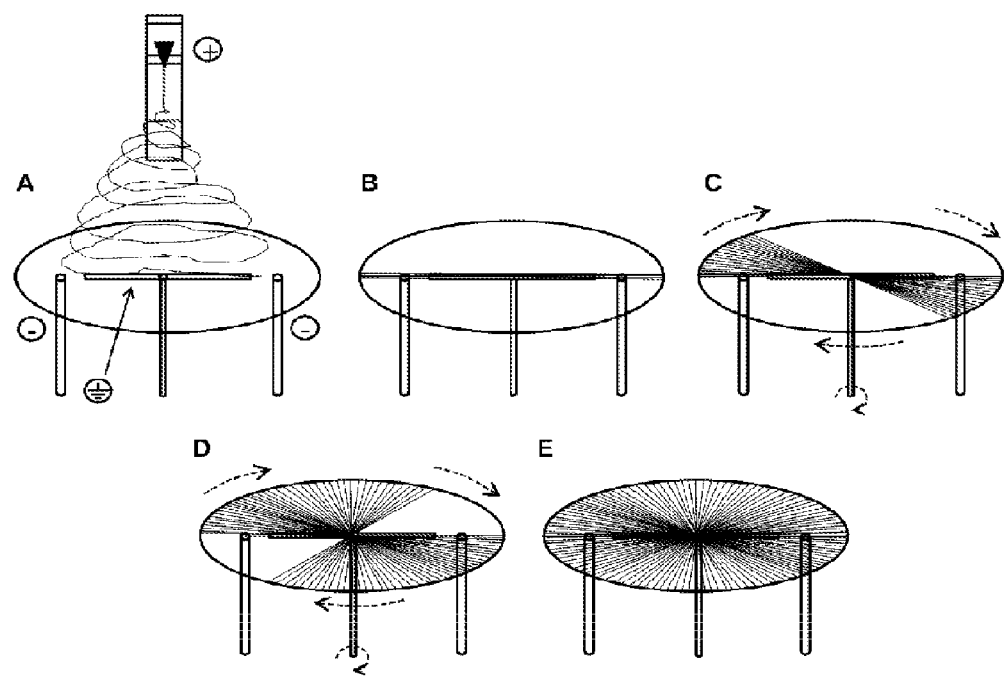
FIG. 5A-E depicts an example of a step-by-step process in which diametrically patterned nanofibers are deposited evenly on a collector assembly via rotation of the collector according to the present disclosure.

In some embodiments, the disk collector is rotated about its central axis during the electrospinning process to produce even deposition of the diametrically patterned fibers, as in FIG. 5.

It will be understood that additional regions or components within this rotating disk system can be used so long as insulating regions are used to separate adjacent conductive regions. For example, in certain embodiments, some of the conductive regions in a multi-component disk embodiment are neither grounded nor charged.

Figure 6:
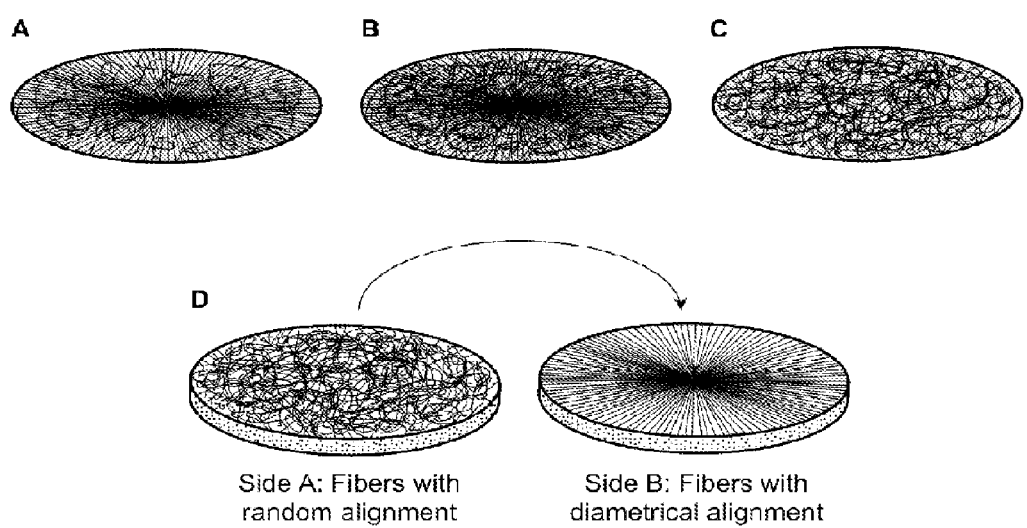
FIG. 6A-C depicts an example of a secondary layer of unaligned fibers being deposited onto a first layer of diametrically patterned fibers according to the present disclosure.
FIG. 6D Depicts an example of a nanofiber membrane having a first layer of diametrically patterned fibers and a second layer of unaligned fibers according to the present disclosure.

With reference to FIG. 6, upon the diametrically aligned fibers reaching a critical density through the electrospinning process, the subsequent deposition of fibers through the same rotation rate and potential applied to the mandrels, strip, and spinneret results in the formation of a second layer of fibers having a different orientation from the first diametrically aligned fibers.

In certain embodiments, the second layer of fibers can be randomly aligned, with no prevalent alignment axis (i.e., no net alignment or direction). Alternatively if, after the diametrically aligned layer has deposited, the configuration of the collecting disk is altered sufficiently, the depositing fibers can be uniaxially aligned. This uniaxial alignment can be achieved by removing the insulating disk from the current assembly and placing it onto a multi-component conveyor belt or drum assembly as described in U.S. Patent Publication No. 2010/0233115. By varying the geometry and charges of the components in the electrospinning area as described, different layers of nanofiber alignment can be achieved within a single scaffold, including random alignment, uniaxial alignment, and diametrically patterned alignment.

In some embodiments, the electrospinning components can be rearranged during the electrospinning process without interruption of the polymer fiber such that the resulting scaffold comprises a single, unbroken polymer fiber. Because of the connection between layers via the unbroken polymer fiber, the different layers cannot be delaminated (i.e. separated completely), or shift along their axis without breaking the single fiber. Accordingly, a multilayer layer scaffold can be constructed that does not readily allow delamination of the layers.

Alternatively, if desired, multilayer scaffolds can be constructed wherein the flow of the polymer solution is stopped at the end of one layer and started at the beginning of the next layer, resulting in a broken polymer fiber, or multiple individual fibers. In such instances, the mechanical continuity between the layers depends at least in part on the electrospinning gap time between the layers.

In one embodiment the continuous or non-continuous layers of fibers may be formed of the same polymer solution. In another embodiment, the continuous or non-continuous layers of fibers may be formed of two or more different polymer solutions. A series of different polymer solutions can be sequentially fed through the same tube into the same electrospinner jet to create a continuous flow even while changing the composition of the solution used to spin fibers.

During the electrospinning process, the spinneret that dispenses the solution may either remain stationary or may move laterally, parallel to the collecting surface of the disk. The spinneret can move in any direction depending upon the desired fiber alignment pattern and scaffold thickness. The spinneret may also encircle the scaffold and/or spray upward from the bottom of the scaffold. The spinneret and mandrel keep the polymer solution moving to ensure substantially even layers of fibers deposited throughout the shape of the scaffold. However, depending upon the specific application, in some embodiments it may be desirable for parts of the scaffold to be thicker than others and the spinneret movement or collector rotation can be adjusted accordingly to accommodate a scaffold of differential thickness.

Figure 7:
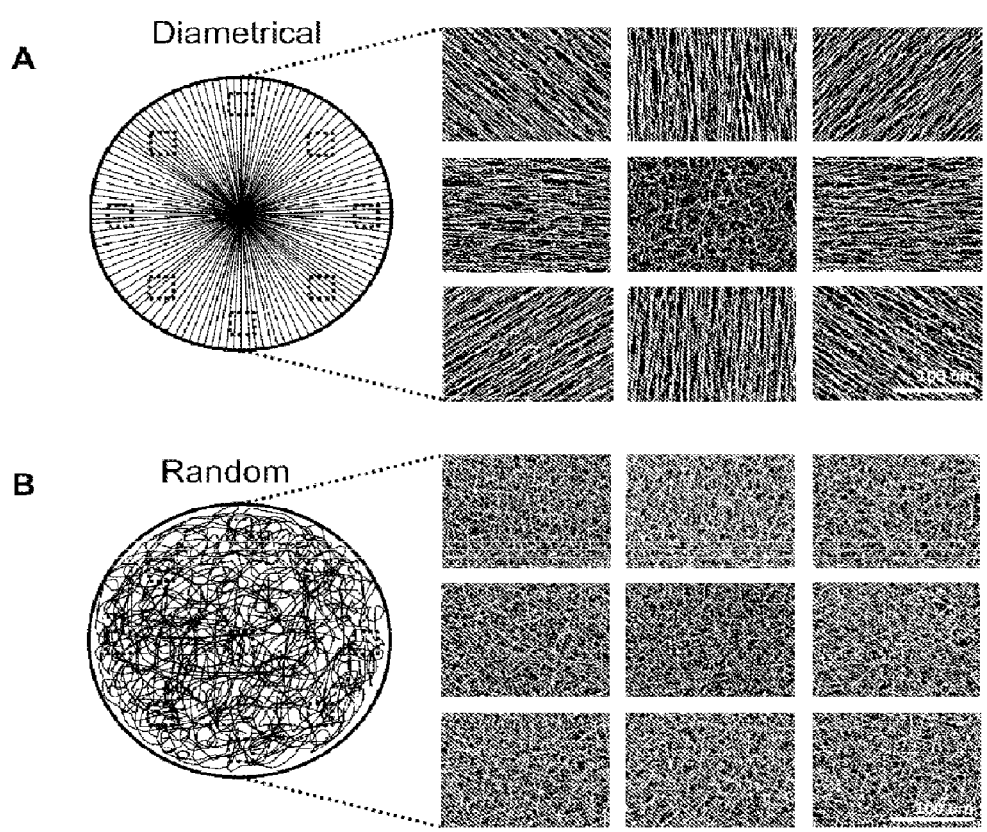
FIG. 7A depicts scanning electron microscopy images of nanofibers from a membrane having a layer of diametrically patterned fibers made according to Example 6 of the present disclosure.
FIG. 7B depicts scanning electron microscopy images of nanofibers from a membrane having a layer of unaligned (i.e. random) fibers made according to Example 6 of the present disclosure.

An example of a first layer of diametrically patterned polymer fibers in a fibrous polymer scaffold, which can be produced using any of the electrospinning apparatuses and techniques described herein, is depicted in FIG. 7A. An example of a second layer of unaligned or randomly oriented polymer fibers in a fibrous polymer scaffold, which can be produced using any of the electrospinning apparatuses and techniques described herein, is depicted in FIG. 7B.

Rotational Assemblies with Conductive Arms

In various embodiments, a rotational assembly device can includes one or more conductive arms such as, for example, those disclosed in U.S. Patent Publication No. 2010/0233115.

The conductive arms are electrically conductive components that can be attached to any of the electrospinning apparatuses disclosed herein. When electrically charged, the conductive arms can be used to repel an electrospinning polymer fiber. Therefore, the direction of polymer fiber deposition can be controlled via the use of one or more conductive arms. In some embodiments, conductive arms can be used to guide the deposition of an electrospinning fiber into a diametrical alignment with respect to a collecting surface. The conductive arms may be used to create fiber alignment on a simple single-component collector or may be used to further enhance alignment on a multi-component collector.

Under typical electrospinning conditions, a positively charged polymer fiber is ejected from a spinneret away from a positively charged spinneret-holder plate, and toward a negatively charged collector (e.g. a disk or other collector).

This is typically done at a distance away from the collector such that there is an air gap between the tip of the spinneret and the collector, through which the polymer fiber travels (see, e.g., FIG. 3A). In the air gap between the spinneret and the collector, the nascent polymer fiber is free to move as it proceeds through the air gap to the collector. It is typical for the polymer fiber to move erratically, in several directions, as it is guided generally by the electric field from the spinneret to the collector.

By introducing additional, positively charged elements such as conductive arms into the vicinity of the electrospinning fiber, the direction of deposition of the polymer fiber can be controlled. The positively charged polymer fiber is repelled from the positive charge of the conducting arms and will thus tend to move in a direction away from the positively charged conducting arms toward a negatively charged element. Alternatively, if the polymer fiber is negatively charged, the conductive arms can be likewise negatively charged to repel and control the fiber.

An example of an apparatus with a pair of positively charged conducting arms is shown in FIG. 3B. In the depicted embodiment, the conductive arms 350 are attached to a spinneret 315 platform, also known as a spinneret holder plate. In the depicted embodiment, the dimensions of the arms 350 are equal. In various embodiments, the conductive arms 350 may be attached to the spinneret-holder plate itself, or may be free-standing elements, existing apart from the spinneret-holder plate.

As shown in FIG. 3B, the conductive arms 350 extend downward from the spinneret 315, toward the desired collector 300, which in the depicted embodiment is a multi-component disk. The conductive arms 350 thus extend into the air gap between the spinneret 315 and the collector 300. During electrospinning, a positive charge is applied to the spinneret-holder plate. When the conductive arms 350 are in direct contact with the spinneret-holder plate, the positive charge is also imparted to the conductive arms 350. A positively charged polymer fiber 320 is ejected from a spinneret tip 315 as described previously. The polymer fiber 320 proceeds through the air gap between the conductive arms 350, toward the disk 300 assembly, which has negatively charged components. Because the conductive arms 350 are positively charged, the positively charged polymer fiber 320 will be repelled by the charge of the conductive arms 350 as it travels from the spinneret tip 315 to the collector 300.

The means of attaching the conductive arms to the spinneret holder plate can be varied. In some embodiments, the conductive arms can be attached to the plate by a clip. In other embodiments, the conductive arms can be attached to the plate by any other mechanical means including, for example, by welding them to the plate, by screwing them into place at the plate, or by other means of attachment. In some embodiments, the conductive arms are not attached to the plate itself, but are rather present in the air gap by some other means including, for example, by a stand that holds each of the conductive arms in place at the air gap.

Any number of conductive arms can be employed. In some embodiments, a single conductive arm is attached to a spinneret-holder plate in an electrospinning apparatus. In some embodiments, two conductive arms are attached to a spinneret-holder plate in an electrospinning apparatus. In some embodiments, three conductive arms are attached to a spinneret-holder plate in an electrospinning apparatus. In some embodiments, four conductive arms are attached to a spinneret-holder plate in an electrospinning apparatus. In some embodiments, five or more conductive arms are attached to a spinneret-holder plate in an electrospinning apparatus. In some embodiments, a single conductive arm is introduced into the air gap in the vicinity of a spinneret-holder plate in an electrospinning apparatus, but is not connected to the plate. In some embodiments, two conductive arms are introduced into the air gap in the vicinity of a spinneret-holder plate in an electrospinning apparatus, but are not connected to the plate. In some embodiments, three conductive arms are introduced into the air gap in the vicinity of a spinneret-holder plate in an electrospinning apparatus, but are not connected to the plate. In some embodiments, four conductive arms are introduced into the air gap in the vicinity of a spinneret-holder plate in an electrospinning apparatus, but are not connected to the plate. In some embodiments, five or more conductive arms are introduced into the air gap in the vicinity of a spinneret-holder plate in an electrospinning apparatus, but are not connected to the plate.

The position and/or orientation of the conductive arms can be altered to prevent the polymer fiber from moving in one or more specific directions and to encourage the polymer fiber to move in one or more other directions as described in U.S. Patent Publication No. 2010/0233115. In some embodiments, the conductive arms are oriented such that they direct the polymer fiber to move and/or deposit along a diametrical axis or axes of a collector. For example, as shown in FIG. 3B, by positioning the inner surfaces of the conductive arms 350 such that they flank both the spinneret 315 and the conducting strip 305 of a multi-component disk collector in an orientation that is both parallel to the long axis of the strip 305 and orthogonal to the surface of the collector 300, the whipping of the fiber 320 is restricted between the arms 350 and is encouraged along the long axis of the strip 305, thereby producing diametrical alignment of the fibers on the collector 300.

The shape and size of the conductive arms can be altered. In some embodiments, the conductive arms are rectangular in shape. In some embodiments, the conductive arms are oval in shape. In some embodiments, the conductive arms are square in shape. In some embodiments, more than one conductive arm is used and each arm is independently a shape selected from rectangular, square and oval.

In some embodiments, the conductive arms have a length of greater than 1 cm, greater than 2 cm, greater than 3 cm, greater than 4 cm, greater than 5 cm, greater than 6 cm, greater than 7 cm, greater than 8 cm, greater than 9 cm, greater than 10 cm, greater than 11 cm, greater than 12 cm, greater than 13 cm, greater than 14 cm, greater than 15 cm, greater than 16 cm, greater than 17 cm, greater than 18 cm, greater than 19 cm, or greater than 20 cm. In some embodiments, the conductive arms have a length of less than 20 cm, less than 19 cm, less than 18 cm, less than 17 cm, less than 16 cm, less than 15 cm, less than 14 cm, less than 13 cm, less than 12 cm, less than 11 cm, less than 10 cm, less than 9 cm, less than 8 cm, less than 7 cm, less than 6 cm, less than 5 cm, less than 4 cm, less than 3 cm, less than 2 cm, or less than 1 cm.

In some embodiments, the conductive arms have a width of greater than 0.1 cm, greater than 0.2 cm, greater than 0.3 cm, greater than 0.4 cm, greater than 0.5 cm, greater than 0.6 cm, greater than 0.7 cm, greater than 0.8 cm, greater than 0.9 cm, greater than 1 cm, greater than 2 cm, greater than 3 cm, greater than 4 cm, greater than 5 cm, greater than 6 cm, greater than 7 cm, greater than 8 cm, greater than 9 cm, or greater than 10 cm. In some embodiments, the conductive arms have a width of less than 10 cm, less than 9 cm, less than 8 cm, less than 7 cm, less than 6 cm, less than 5 cm, less than 4 cm, less than 3 cm, less than 2 cm, less than 1 cm, less than 0.9 cm, less than 0.8 cm, less than 0.7 cm, less than 0.6 cm, less than 0.5 cm, less than 0.4 cm, less than 0.3 cm, less than 0.2 cm, or less than 0.1 cm.

In some embodiments, the conductive arms have a thickness of greater than 0.1 cm, greater than 0.2 cm, greater than 0.3 cm, greater than 0.4 cm, greater than 0.5 cm, greater than 0.6 cm, greater than 0.7 cm, greater than 0.8 cm, greater than 0.9 cm, greater than 100 cm, greater than 1.1 cm, greater than 1.2 cm, greater than 1.3 cm, greater than 1.4 cm, greater than 1.5 cm, greater than 1.6 cm, greater than 1.7 cm, greater than 1.8 cm, greater than 1.9 cm, or greater than 2.0 cm. In some embodiments, the conductive arms have a thickness of less than 2.0 cm, less than 1.9 cm, less than 1.8 cm, less than 1.7 cm, less than 1.6 cm, less than 1.5 cm, less than 1.4 cm, less than 1.3 cm, less than 1.2 cm, less than 1.1 cm, less than 1.0 cm, less than 0.9 cm, less than 0.8 cm, less than 0.7 cm, less than 0.6 cm, less than 0.5 cm, less than 0.4 cm, less than 0.3 cm, less than 0.2 cm, or less than 0.1 cm.

In various embodiments, the electrically conducting arms can be constructed of any conductive material. Conductive materials can include metals such as, for example, aluminum, copper, silver, gold, iron, nickel, titanium and alloys including, without limitation, steels, bronze, brass and conductive polymers such as polyaniline, polypyrrole, polyacetylene, polythiopene. In some embodiments, the conducting arms are constructed of the same material as the collector used in the electrospinning apparatus.

By deliberately placing the conductive arms within the electrospinning area, the overall electric field within the electrospinning area in any electrospinning apparatus, inclusive of those disclosed herein, can be altered. The conducting arms can thus be used to guide the movement of a polymer fiber during electrospinning. In various embodiments, the conductive arms can be used to improve the overall alignment of the polymer fibers deposited in a scaffold. In some embodiments, two rectangular shaped conductive arms can be employed in an electrospinning apparatus such that a flat face of each conductive arm is oriented opposite the other, as depicted in FIG. 3B. As shown in the embodiment depicted in FIG. 3B, the presence of the conductive arms allows for greater control of the direction of polymer fiber movement, and this the direction of polymer fiber deposition along a collector.

Differences in spinneret height can be used to help control the degree of polymer fiber alignment when conductive arms are employed. As noted herein, the distance between the spinneret tip and the top surface of the collector can have an effect on the resulting deposition of the polymer fibers along a collector. In various aspects, conductive arms can be employed with an electrospinning apparatus when the spinneret tip is positioned at any height above the collector. In some embodiments, the conductive arms can be employed when the spinneret tip is positioned at lower heights. In some embodiments, conductive arms can be used to direct polymer fiber alignment and deposition when the spinneret tip is positioned greater than 5 cm, greater than 6 cm, greater than 7 cm, greater than 8 cm, greater than 9 cm, greater than 10 cm, greater than 11 cm, greater than 12 cm, greater than 13 cm, greater than 14 cm, greater than 15 cm, greater than 16 cm, greater than 17 cm, greater than 18 cm, greater than 19 cm, greater than 20 cm, greater than 21 cm, greater than 22 cm, greater than 23 cm, greater than 24 cm, greater than 25 cm, greater than 26 cm, greater than 27 cm, greater than 28 cm, greater than 29 cm, or greater than 30 cm above the collector. In some embodiments, conductive arms can be used to direct polymer fiber alignment and deposition when the spinneret tip is positioned less than 30 cm, less than 29 cm, less then 28 cm, less than 27 cm, less than 26 cm, less than 25 cm, less than 24 cm, less than 23 cm, less than 22 cm, less than 21 cm, less than 20 cm, less than 19 cm, less than 18 cm, less than 17 cm, less than 16 cm, less than 15 cm, less than 14 cm, less than 13 cm, less than 12 cm, less than 11 cm, less than 10 cm, less than 9 cm, less than 8 cm, less than 7 cm, less than 6 cm, or less than 5 cm above the collector. In some embodiments, conductive arms can be used to direct polymer fiber alignment and deposition when the spinneret tip is positioned approximately 15 cm above the collector. In some embodiments, conductive arms can be used to direct polymer fiber alignment and deposition when the spinneret tip is positioned approximately 12 cm above the collector. In some embodiments, conductive arms can be used to direct polymer fiber alignment and deposition when the spinneret tip is positioned approximately 11 cm above the collector. In some embodiments, conductive arms can be used to direct polymer fiber alignment and deposition when the spinneret tip is positioned approximately 10 cm above the collector. During a typical electrospinning process, at lower spinneret heights alignment of polymer fibers is more difficult because the fibers do not have sufficient time to arch in advance of deposition and thus the fibers tend to deposit in a more random orientation. While not wishing to be limited to any particular theory or embodiment, it is believed that, at lower spinneret heights, the conductive arms make up for a lack of arching fibers in terms of overall alignment by controlling the direction of fiber alignment for a greater distance across the air gap between the spinneret tip and the collector. In some embodiments, the conductive arms can be employed to contain the movement of the polymer fiber for a larger fraction of its travel across the air gap from the spinneret tip to the collector.

The conductive arms alter the overall electric field in the electrospinning area to manipulate fiber movement and deposition. However, differences in the electric field in the electrospinning area also cause differences in the minimum required voltage to achieve an electrospinning fiber. The electrospinning process and required voltages can be specifically controlled by varying the size and geometry of the conductive arms, and thus, manipulating the induced electric field. In some embodiments, two conducting arms having a width of from 0.25 cm-2.0 cm are used during electrospinning. In some embodiments, two conductive arms of 1.5 cm width are used during electrospinning. In some embodiments, two conductive arms of 0.5 cm width are used during electrospinning. In some embodiments, the voltage required for electrospinning can be reduced by using conductive arms with a narrow width.

Fiber alignment can be altered within the various layers of a single scaffold by altering the orientation of the conductive arms for each layer accordingly. For example, during a single electrospinning run, the orientation of the conductive arms can be changed. During a single electrospinning run, conductive arms can be added or removed at various points. In some embodiments, the orientation of the conductive causes the fibers to deposit along the diametrical axes of the collector during electrospinning, as depicted, for example, in FIG. 3B. In some embodiments, the orientation of the conductive arms is changed during electrospinning. In some embodiments, conductive arms are removed at the start of a particular layer. In some embodiments, conductive arms are added at the start of a particular layer.

Polymer fiber alignment is dependent on the orientation of the conductive arms during electrospinning. In some embodiments, the inner surfaces of the arms that flank the spinneret are oriented parallel to the diametrical axes of the collector and orthogonal to the surface of the collector during electrospinning and the polymer fibers in the resulting layer of the scaffold are deposited parallel to the diametrical axes of the collector. In various embodiments, the inner surfaces of the conductive arms are oriented parallel or perpendicular to a particular single axis of the collector and orthogonal to the surface of the collector during electrospinning and the polymer fibers in the resulting layer of the scaffold are uniaxially aligned. In various embodiments, the conductive arms are removed from the electrospinning area and the polymer fibers in the resulting area are randomly aligned.

In various aspects, the conductive arms can be used during electrospinning to improve polymer fiber alignment in a scaffold. In some embodiments, conductive arms can be used in an electrospinning apparatus having a simple single-component disk collector (such as the one as in FIG. 3A) to improve fiber alignment by orienting the inner surfaces of the conductive arms parallel to the diametrical axes of the collector and orthogonal to the surface of the collector. In some embodiments, conductive arms can be used in conjunction with an electrospinning apparatus having a more complex multi-component disk collector (such as the one as in FIG. 3B) to improve fiber alignment further by orienting the conductive arms parallel to the axis of alignment formed by the conductive collector components. In some embodiments, the conductive arms can be used to continue producing fibers with diametrical or uniaxial alignment even after the initial fibers have already created an insulating layer on the surface of the collector.

EXAMPLES

The following examples describe in detail the preparation and properties of certain fibrous polymer scaffolds, and apparatuses and methods used for their preparation. It will be apparent to those skilled in the art that many modifications, both to materials and methods, may be practiced without departing from the scope of the disclosure.

Although the electrospinning apparatuses and differentially aligned fibrous scaffold fabrication methods may be performed with other electrospinning systems, designs and techniques, a description of various functional systems is provided below.

Example 1

Production of a Layer of Randomly Oriented Polymer Fibers

To produce a fibrous scaffold, an electrospinning assembly was used as depicted in FIG. 2. First, a polymer solution used to form the fibers was loaded into a syringe and bubbles were eliminated. The polymer solution was prepared within a chemical hood and the solution source and loaded syringe were stored upright to reduce bubbles. A piece of polytetrafluoroethylene (PTFE) (i.e., Teflon™) tube was cut to a sufficient length to connect the syringe pump and the spinneret platform, while minimizing the distance between them.

Male and female luer-lock connectors were attached to the tube. A 25 g stainless steel needle was attached to the female luer-lock connector on the tube. The syringe was attached to the male connector on the tube. All luer-lock connections were tightly sealed.

The syringe assembly was attached to the syringe pump. The syringe pump modulated the pressure and flow of the polymer solution to the spinneret while preventing blockage. The spinneret was attached to a slot in the needle platform. The syringe plunger was pushed manually until the polymer solution reached the needle reservoir. The syringe pump panel was pushed and locked to contact the syringe plunger. The flow rate, syringe size and total solution volume were adjusted via the pump digital display.

The spinneret platform was adjusted to the appropriate position to optimize the distance between the tip of the spinneret and the surface of the collector substrate. The spinneret assembly was stationary and centered during the fiber deposition process as polymer solution was allowed to pass through the spinneret tip.

Alignment of polymer fibers depositing on a collector during electrospinning is directly influenced by the arrangement, geometries, and electrical charges of the various elements within the electrospinning area, including the needle platform, the collector itself and other nearby components. In this example, an electrically grounded collector with a uniform circular geometry was used as depicted in FIG. 3A. In this example, the collector was a stainless steel disk (13.5 cm diameter) with a thin circular disk of polyvinyldifluoride (0.03" thick, 13.5 cm diameter) secured on top. The spinneret assembly was stationary and centered during the fiber deposition process as polymer solution was allowed to pass through the positively charged spinneret tip during the electrospinning process. The collector was connected to a motorized rotational assembly via a rod and the collector was rotated at a constant speed to ensure even deposition of the fibers. Randomly oriented fibers were deposited on the polyvinyldifluoride surface of the collector.

Example 2

Production of a Layer of Diametrically Patterned Polymer Fibers

To produce diametrically patterned polymer fibers, an electrospinning assembly as depicted in FIG. 3B was utilized as shown. The collector was a thin circular disk of polyvinyldifluoride (0.03" thick, 13.5 cm diameter) positioned in front of three electrically conductive stainless steel elements: one rectangular strip (5.0 cm length, 2.0 mm width) in the center and two flanking mandrels (3.0 mm diameter) positioned 1.0 cm away from each end of the strip. Two rectangular stainless steel conductive arms (7 cm length, 2 mm width) were also placed on either side the spinneret (each 2.75 cm away) parallel to the orientation of the strip behind the polyvinyldifluoride disk.

The conductive components in the electrospinning setup were electrically charged as depicted in FIG. 3B: the spinneret and arms were positively charged, the mandrels were negatively charged, and the strip was grounded. The spinneret assembly was stationary and centered during the fiber deposition process as polymer solution was allowed to pass through the positively charged spinneret tip. The polyvinyldifluoride disk was connected to a motorized rotational assembly via a rod passing through the center of the conductive strip. The polyvinyldifluoride disk was rotated at a constant speed to ensure even deposition of the fibers while the strip and mandrels behind the disk remained stationary. Diametrically patterned fibers were deposited on the surface of the collector.

In another trial, the strip behind the polyvinyldifluoride disk was replaced with a stainless steel disk (5.0 cm diameter) placed in front of the collector as depicted in FIG. 4 and fibers were produced having comparable diametrical alignment. FIG. 5 presents a step-by-step depiction of the rotational motion of the collector utilized in this example that resulted in a uniform layer of diametrically patterned fibers.

Example 3

Production of a Multiple Layer Scaffold

A fibrous scaffold having multiple layers was created using the electrospinning assemblies described herein. The electrospinning assembly was first arranged as in Example 2 for generating diametrically patterned fibers in a first layer of the scaffold. Rotation of the collector assembly was started. The negative polarity power supply was turned on, set to −6 V, and connected to the mandrels behind the disk to impart a negative charge to them.

The syringe pump was activated to allow the flow of the polymer solution. When a droplet of the polymer solution had formed at the tip of the spinneret, a positive polarity power supply was connected to the spinneret assembly including the conductive arms, and turned on in order to impart a positive charge to the polymer solution and arms. The positive voltage was incrementally increased until a jet of polymer solution formed and a Taylor cone stabilized.

The positive and negative voltages were adjusted as necessary to ensure even fiber deposition on the surface of the collector. The Taylor cone was stabilized at the tip of the spinneret so that the cone where the fiber jet extended out toward collector substrate did not change in size. The voltage was decreased if the cone was observed to decrease in size. The voltage was increased if the cone was observed to increase in size.

A first layer of diametrically patterned fibers was allowed to form on the surface of the collector. The spinneret assembly was stationary and centered during formation of the diametrically patterned layer of fibers as the polymer solution was allowed to pass through the spinneret tip and diametrically patterned fibers formed as shown in FIG. 5.

After electrospinning the diametrically patterned layer to the desired thickness, the polymer flow rate was stopped, the power supplies were turned off, the collector rotation was stopped, and the polyvinyldifluoride disk with deposited fibers was transferred onto the front of a conductive stainless steel disk as described in Example 1. The conductive mandrels were removed from the collector area and the conductive arms were removed from the spinneret assembly.

Rotation was then started for the new collector assembly and the polymer flow rate was turned back on. Negative voltage was applied to the collector and positive voltage was applied to the spinneret assembly, as before. Randomly oriented fibers were deposited as a second layer on top of the diametrically patterned fibers during this second electrospinning step as shown in FIG. 6.

During production of the randomly oriented layer of fibers, the spinneret assembly was offset with respect to the center of the collector surface to create a more even thickness for the overall multilayer scaffold. Electrospinning proceeded until the desired thickness of the randomly oriented fiber layer was achieved.

After electrospinning was complete, the positive and negative power supplies, collector rotation motor, and syringe pump were stopped simultaneously. The resulting fibrous scaffold had a first layer of diametrically patterned fibers and a second layer of randomly oriented fibers as shown in FIG. 6.

Example 4

Production of a Fibrous Scaffold Having Randomly Oriented Fibers Made Using Poly(L-Lactide-Co-Caprolactone) with Poly(Propylene Glycol)

A fibrous scaffold having a single layer of randomly oriented fibers was created using the electrospinning processes described herein. A polymer solution of poly(L-lactide-co-caprolactone) (PLCL), having a molar weight ratio of 70:30 lactide:caprolactone (Purac Biomaterials, Amsterdam Netherlands), sodium acetate (Sigma-Aldrich St. Louis, Mo.) and poly(propylene glycol) (PPG) (Acros Organics, NJ) dissolved in hexafluoroisopropanol (Matrix Scientific, Columbia, S.C.) was used to fabricate scaffolds, as described herein. The concentration of PLCL, sodium acetate and PPG was such that the final polymer fiber composition was 92.6% poly(L-lactide-co-caprolactone), 6.2% poly(propylene glycol), and 1.2% sodium acetate.

The electrospinning assembly was arranged as described in Example 1. The polymer solution was loaded onto a syringe pump and delivered to the spinneret at a rate of 3 ml/hr. The spinneret was centered and positioned a distance of 13.5 cm from the stainless steel and polyvinyldifluoride collector disk assembly. The collector disk assembly was electrically grounded and rotated at 20 RPM. The electrospinning process was started by charging the polymer solution with a positive high voltage power supply set at +16 kV. The electrospinning process proceeded for 20 minutes.

After electrospinning was complete, the positive high voltage power supply, collector rotation motor, and syringe pump were stopped simultaneously. The fibrous scaffold was air dried for 48 hr and then removed from the polyvinyldifluoride collector disk. The resulting fibrous scaffold had a layer of randomly oriented fibers and a thickness of 180 µm.

Example 5

Production of a Fibrous Scaffold Having Diametrically Patterned Fibers Made Using Poly(L-Lactide-Co-Caprolactone) with Poly(Propylene Glycol)

A fibrous scaffold having a single layer of diametrically patterned fibers was created using the electrospinning processes described herein. A polymer solution of poly(L-lactide-co-caprolactone) (PLCL), having a molar weight ratio of 70:30 lactide:caprolactone (Purac Biomaterials, Amsterdam Netherlands), sodium acetate (Sigma-Aldrich St. Louis, Mo.) and poly(propylene glycol) (PPG) (Acros Organics, NJ) dissolved in hexafluoroisopropanol (Matrix Scientific, Columbia, S.C.) was used to fabricate scaffolds, as described herein. The concentration of PLCL, sodium acetate and PPG was such that the final polymer fiber composition was 92.6% poly(L-lactide-co-caprolactone), 6.2% poly(propylene glycol), and 1.2% sodium acetate.

The electrospinning assembly was setup as described in Example 2. The polymer solution was loaded onto a syringe pump and delivered to the spinneret at a rate of 1 ml/hr. The spinneret assembly including the conducting arms was centered and positioned a distance of 13 cm from the collector disk assembly. Two conducting arms were used as shown in FIG. 3B. Each arm had a length of 7 cm and a width of 0.9 cm. The spacing between the arms was 7 cm, with the needle positioned directly in between. The stainless steel mandrels were positioned such that the mandrel ends were in contact with the back surface of the polyvinyldifluoride disk and spaced 7 cm horizontally apart from each other. A metal strip having length of 5 cm was centered within the 7 cm space between the mandrel ends and made to contact the back surface of the polyvinyldifluoride disk as illustrated in FIG. 3B. The metal mandrels were charged with a negative high voltage power supply set to −6 kV. The metal strip was electrically grounded. The polyvinyldifluoride disk was rotated at 20 RPM around its center axis. The electrospinning process was started by charging the polymer solution with a positive high voltage power supply set to +17.5 kV. The electrospinning process proceeded for 20 minutes.

After electrospinning was complete, the positive and negative high voltage power supplies, collector rotation motor, and syringe pump were stopped simultaneously. The fibrous scaffold was removed from the polyvinyldifluoride collector disk. The resulting fibrous scaffold had a layer of diametrically patterned fibers and a thickness of 30 μm.

Example 6

Production of a Multilayer Fibrous Scaffold Having a First Layer of Diametrically Patterned Fibers and a Second Layer of Unaligned Fibers Made Using Poly(L-Lactide-Co-Caprolactone) with Poly(Propylene Glycol)

A fibrous scaffold having a first layer of diametrically patterned fibers and a second layer of unaligned fibers was created using the electrospinning processes described herein. A polymer solution of poly(L-lactide-co-caprolactone) (PLCL), having a molar weight ratio of 70:30 lactide:caprolactone (Purac Biomaterials, Amsterdam Netherlands), sodium acetate (Sigma-Aldrich St. Louis, Mo.) and poly(propylene glycol) (PPG) (Acros Organics, NJ) dissolved in hexafluoroisopropanol (Matrix Scientific, Columbia, S.C.) was used to fabricate scaffolds, as described herein. The concentration of PLCL, sodium acetate and PPG was such that the final polymer fiber composition was 92.6% poly(L-lactide-co-caprolactone), 6.2% poly(propylene glycol), and 1.2% sodium acetate.

The first layer of diametrically patterned fibers was created using the electrospinning process as described in Example 5. After the electrospinning process was completed, the fibrous scaffold having a first layer of diametrically patterned fibers remained on the polyvinyldifluoride disk. The polyvinyldifluoride disk was removed from the collector assembly and attached to a stainless steel disk as described in Example 1. The conducting arms were removed from the spinneret assembly and the metal strip and metal mandrels were removed from the collector disk assembly.

The stainless steel disk with the attached polyvinyldifluoride disk was re-attached to the collector assembly. The spinneret assembly was offset horizontally 2 cm from the center point of the polyvinyldifluoride disk assembly, to allow for uniform fiber deposition across the polyvinyldifluoride disk. The polymer solution delivery was re-started at a flow rate of 3 ml/hr. The collector assembly was electrically grounded and rotated at 20 RPM. The electrospinning process was started by charging the polymer solution with a positive high voltage power supply set to +16 kV. Electrospinning proceeded for 45 minutes.

After electrospinning was complete, the positive high voltage power supply, collector rotation motor, and syringe pump were stopped simultaneously. The fibrous scaffold was removed from the polyvinyldifluoride disk assembly. The resulting bi-layered fibrous scaffold had a first layer of diametrically patterned fibers and a second layer of unaligned fibers. The scaffold thickness was 200 μm at the edges and 240 μm at the center. Scanning Electron Microscopy (SEM) images in FIGS. 7A and 7B confirm the expected alignment of the fibers at various regions on the nanofiber membrane. On the surface of the membrane designed to have randomly oriented fibers, SEM confirms that the fibers are randomly oriented as shown in FIG. 7B. On the side of the membrane designed to have diametrically patterned fibers, SEM shows that fibers at various regions around the periphery are diametrically aligned towards the convergence region of the membrane (all periphery areas were ~2 cm from the center of the membrane) as illustrated in FIG. 7A. SEM from the convergence region shows fibers overlapping at various angles, as expected, in FIG. 7A.

Example 7

Production of a Multilayer Fibrous Scaffold Having a First Layer of Diametrically Patterned Fibers Made Using Poly(L-Lactide-Co-Caprolactone) with Poly(Propylene Glycol) and a Second Layer of Unaligned Fibers Made Using Poly(L-Lactic Acid)

A fibrous scaffold having a first layer of diametrically patterned PLCL fibers and a second layer of unaligned poly (L-lactide) (PLLA) fibers is created using the electrospinning processes described herein. A polymer solution of poly(L-lactide-co-caprolactone) (PLCL), having a molar weight ratio of 70:30 lactide:caprolactone (Purac Biomaterials, Amsterdam Netherlands), sodium acetate (Sigma-Aldrich St. Louis, Mo.) and poly(propylene glycol) (PPG) (Acros Organics, NJ) dissolved in hexafluoroisopropanol (Matrix Scientific, Columbia, S.C.) is used to fabricate the first PLCL fiber layer, as described herein. The concentration of PLCL, sodium acetate and PPG is such that the final polymer fiber composition is 92.6% poly(L-lactide-co-caprolactone), 6.2% poly(propylene glycol), and 1.2% sodium acetate. A polymer solution of PLLA (Sigma Aldrich, St. Louis, Mo.) and sodium acetate (Sigma-Aldrich St. Louis, Mo.) dissolved in hexafluoroisopropanol (Matrix Scientific, Columbia, S.C.) is used to fabricate the second PLLA fiber layer, as described herein. The concentration of PLLA and sodium acetate is such that the final polymer fiber composition is 98.7% PLLA, and 1.3% sodium acetate.

The first layer of diametrically patterned PLCL fibers is created using the electrospinning process as described in Example 5. After the electrospinning process is completed, the fibrous scaffold having a first layer of diametrically patterned fibers remains on the polyvinyldifluoride disk. The polyvinyldifluoride disk is removed from the collector assembly and attached to a stainless steel disk as described in Example 1. The conducting arms are removed from the spinneret assembly and the metal strip and metal mandrels are removed from the collector disk assembly.

The stainless steel disk with the attached polyvinyldifluoride disk is re-attached to the collector assembly. The PLLA polymer solution is loaded onto the syringe pump and delivered to the spinneret. The spinneret assembly is offset horizontally 2 cm from the center point of the polyvinyldifluoride disk assembly, to allow for uniform fiber deposition across the polyvinyldifluoride disk. The PLLA polymer solution delivery is started at a flow rate of 1 ml/hr. The collector assembly is electrically grounded and rotated at 20 RPM. The electrospinning process is started by charging the polymer solution with a positive high voltage power supply set to +16 kV. The electrospinning process proceeds for 20 minutes.

After electrospinning is complete, the positive high voltage power supply, collector rotation motor, and syringe pump are stopped simultaneously. The fibrous scaffold is removed from the polyvinyldifluoride disk assembly. The resulting bi-layered fibrous scaffold has a first layer of diametrically patterned 92.6% PLCL, 6.2% PPG, and 1.2% sodium acetate fibers and a second layer of unaligned 98.7% PLLA and 1.3% sodium acetate fibers.

Example 8

Production of a Multilayer Fibrous Scaffold Having a First Layer of Diametrically Patterned Fibers and a Second Layer of Unaligned Fibers Made Using Poly(L-Lactide-Co-Caprolactone) with Poly(Propylene Glycol) in an Uninterrupted Production Process A fibrous scaffold having a first layer of diametrically patterned fibers and a second layer of unaligned fibers is created using the electrospinning processes described herein. A polymer solution of poly(L-lactide-co-caprolactone) (PLCL), having a molar weight ratio of 70:30 lactide:caprolactone (Purac Biomaterials, Amsterdam Netherlands), sodium acetate (Sigma-Aldrich St. Louis, Mo.) and poly(propylene glycol) (PPG) (Acros Organics, NJ) dissolved in hexafluoroisopropanol (Matrix Scientific, Columbia, S.C.) is used to fabricate scaffolds, as described herein. The concentration of PLCL, sodium acetate and PPG is such that the final polymer fiber composition is 92.6% poly(L-lactide-co-caprolactone), 6.2% poly(propylene glycol), and 1.2% sodium acetate.

The first layer of diametrically patterned fibers is created using the electrospinning process as described in Example 5. After 20 minutes of electrospinning the diametrically patterned fiber layer, the electrospinning process is not stopped. The conducting arms of the spinneret assembly are receded from the spinneret assembly to remove their influence on the trajectory of the electrospinning jet. The conducting metal strip and negatively charged mandrel ends at the back of the collector disk assembly are receded until they no longer are in contact with the back surface of the disk. The negative high voltage power supply connected to the mandrels is turned off. The spinneret assembly is offset horizontally 2 cm from the center point of the polyvinyldifluoride disk. The flow rate of the polymer solution is increased to 3 ml/hr and the positive voltage is adjusted to maintain a stable Taylor cone and electrospinning jet. The electrospinning process proceeds for an additional 20 minutes.

After electrospinning is complete, the positive high voltage power supply, collector rotation motor, and syringe pump are stopped simultaneously. The fibrous scaffold is removed from the polyvinyldifluoride disk assembly. The resulting bi-layered fibrous scaffold has a first layer of diametrically patterned fibers and a second layer of unaligned fibers, wherein at least one fiber spans both the first and second layers of the fibrous polymer scaffold.

Example 9

Production of a Multilayer Fibrous Scaffold Having a First Layer of Diametrically Patterned Fibers and a Second Layer of Uniaxially Aligned Fibers Made Using Poly(L-Lactide-Co-Caprolactone) with Poly(Propylene Glycol)

A fibrous scaffold having a first layer of diametrically patterned fibers and a second layer of uniaxially aligned fibers is created using the electrospinning processes described herein. A polymer solution of poly(L-lactide-co-caprolactone) (PLCL), having a molar weight ratio of 70:30 lactide:caprolactone (Purac Biomaterials, Amsterdam Netherlands), sodium acetate (Sigma-Aldrich St. Louis, Mo.) and poly(propylene glycol) (PPG) (Acros Organics, NJ) dissolved in hexafluoroisopropanol (Matrix Scientific, Columbia, S.C.) is used to fabricate scaffolds, as described herein. The concentration of PLCL, sodium acetate and PPG is such that the final polymer fiber composition is 92.6% poly(L-lactide-co-caprolactone), 6.2% poly(propylene glycol), and 1.2% sodium acetate.

The first layer of diametrically patterned fibers is created using the electrospinning process as described in Example 5. After the electrospinning process is completed, the fibrous scaffold having a single layer of diametrically patterned fibers remains on the polyvinyldifluoride disk.

The polyvinyldifluoride disk with the fibrous scaffold is removed from the collector assembly and attached to the surface of a conveyor belt assembly as described in U.S. Patent Publication No. 2010/0233115. The conveyor belt is 11 cm wide and made of polyvinyldifluoride. The center 7 cm wide region of the belt is covered with a 0.002" thick stainless steel shim. The conveyor belt is attached to a ⅛" diameter rotating mandrel at the top end and a belt tensioner at the bottom end. The rotating mandrel is an electrically insulating ceramic mandrel coated with electrically conducting stainless steel such that the central 10 cm section of the mandrel is bare ceramic and the two flanking regions are stainless steel coated. The conveyor belt is positioned around the mandrel such that the stainless steel coating of the mandrel overlaps 0.5 cm under the ends of the polyvinyldifluoride belt. The top end of the conveyor belt assembly is positioned 12 cm below the electrospinner spinneret. The spinneret assembly's conductive arms are positioned such that they are perpendicular to the long axis of the rotating mandrel.

The stainless steel coated regions of the rotating mandrel are charged with a negative high voltage power supply set to −6 kV. The belt is rotated at 20 RPM. The flow rate of the PLCL polymer solution is set to 1 ml/hr. The electrospinning process is started by charging the polymer solution with a positive high voltage power supply set to +15 kV. The electrospinning process proceeds for 20 minutes. During the electrospinning process the fibers align uniaxially across the width of the 7 cm stainless steel section of the conveyor belt. The process deposits a fiber of uniaxially aligned fibers on top of the diametrically patterned fiber layer on the polyvinyldifluoride disk.

After electrospinning is complete, the positive and negative high voltage power supplies, collector rotation motor, and syringe pump are stopped simultaneously. The fibrous scaffold is removed from the polyvinyldifluoride disk and conveyor belt assembly. The resulting bi-layered fibrous scaffold has a first layer of diametrically patterned fibers and a second layer of uniaxially aligned fibers.

Example 10

Production of a Multilayer Fibrous Scaffold Having a First Layer of Diametrically Patterned Fibers Made Using Poly(L-Lactide-Co-Caprolactone) with Poly(Propylene glycol) and a Second Layer of Uniaxially Aligned Fibers Made Using Poly(L-Lactic Acid)

A fibrous scaffold having a first layer of diametrically patterned PLCL fibers and a second layer of uniaxially aligned PLLA fibers is created using the electrospinning processes described herein. A polymer solution of poly(L-lactide-co-caprolactone) (PLCL), having a molar weight ratio of 70:30 lactide:caprolactone (Purac Biomaterials, Amsterdam Netherlands), sodium acetate (Sigma-Aldrich St. Louis, Mo.) and poly(propylene glycol) (PPG) (Acros Organics, NJ) dissolved in hexafluoroisopropanol (Matrix Scientific, Columbia, S.C.) is used to fabricate the first fibrous scaffold layer, as described herein. The concentration of PLCL, sodium acetate and PPG is such that the final polymer fiber composition is 92.6% poly(L-lactide-co-caprolactone), 6.2% poly(propylene glycol), and 1.2% sodium acetate. A polymer solution of PLLA (Sigma Aldrich, St. Louis, Mo.) and sodium acetate (Sigma-Aldrich St. Louis, Mo.) dissolved in hexafluoroisopropanol (Matrix Scientific, Columbia, S.C.) is used to fabricate the second PLLA fiber layer, as described herein. The concentration of PLLA and sodium acetate is such that the final polymer fiber composition is 98.7% PLLA, and 1.3% sodium acetate.

The first layer of diametrically patterned fibers is created using the electrospinning process as described in Example 5. After the electrospinning process is completed, the fibrous scaffold comprising diametrically patterned fibers remains on the polyvinyldifluoride disk.

The polyvinyldifluoride disk with the fibrous scaffold is removed from the collector assembly and attached to the surface of a conveyor belt assembly as per Example 9. The conveyor belt is 11 cm wide and comprises polyvinyldifluoride. The center 7 cm wide region of the belt is covered with a 0.002" thick stainless steel shim. The conveyor belt is attached to a ⅛" diameter rotating mandrel at the top end and a belt tensioner at the bottom end. The rotating mandrel is an electrically insulating ceramic mandrel coated with electrically conducting stainless steel such that the central 10 cm section of the mandrel is bare ceramic and the two flanking regions are stainless steel coated. The conveyor belt is positioned around the mandrel such that the stainless steel coating of the mandrel overlaps 0.5 cm under the ends of the polyvinyldifluoride belt. The top end of the conveyor belt assembly is positioned 12 cm below the electrospinner spinneret. The spinneret assembly's conductive arms are positioned such that they are perpendicular to the long axis of the rotating mandrel.

The stainless steel coated regions of the rotating mandrel are charged with a negative high voltage power supply set to −6 kV. The belt is rotated at 20 RPM. The PLLA polymer solution is loaded onto the syringe pump and delivered to the spinneret at a flow rate of 1 ml/hr. The electrospinning process is started by charging the polymer solution with a positive high voltage power supply set to +15 kV. The electrospinning process proceeds for 20 minutes. During the electrospinning process the PLLA fibers align uniaxially across the width of the 7 cm stainless steel section of the conveyor belt. The process deposits a fiber of uniaxially aligned PLLA fibers on top of the diametrically patterned PLCL fiber layer on the polyvinyldifluoride disk.

After electrospinning is complete, the positive and negative high voltage power supplies, collector rotation motor, and syringe pump are stopped simultaneously. The fibrous scaffold is removed from the polyvinyldifluoride disk and conveyor belt assembly. The resulting bi-layered fibrous scaffold has a first layer of diametrically patterned PLCL fibers and a second layer of uniaxially aligned PLLA fibers.

Example 11

In Vitro Wound Healing Assay Demonstrating the Effectiveness of Diametrically Patterned Nanofibers for Influencing Cell Migration and Closing Gap Defects To test the efficacy of diametrically patterned nanofibers for enhancing cell migration and wound healing, an in vitro model was used. Nanofiber membranes having a first layer of diametrically patterned fibers and a second layer of unaligned fibers were produced as described in example 6. Each membrane was cut into a 2×2 cm square with the convergence region of the diametrical fibers positioned at the center of the square. Membranes having either uniaxially or randomly oriented fiber layers were used as controls. A circular disk (1 cm D) was placed onto the center of each membrane in order to prevent cell attachment underneath and human mesenchymal stem cells (MSCs) were then seeded at confluency on the membranes around the periphery of each disk. Following attachment of the cells to the nanofibers, each disk was removed leaving an initial circular gap defect, a simulated wound, where no cells were present.

Immediately prior to seeding, MSCs were stained using DiI cell tracker (Invitrogen, Carlsbad, Calif.) to determine the initial "wound" edges and to monitor the progression of "wound" coverage. Samples were maintained for 7 days, during which time the cells migrated from the periphery of each gap defect "wound" towards the center. Samples were then fluorescently stained for total actin using Alexa Fluor 488 phalloidin (Invitrogen, Carlsbad, Calif.) to view the cytoskeletal structure of the cells within the wound area.

Figure 8:
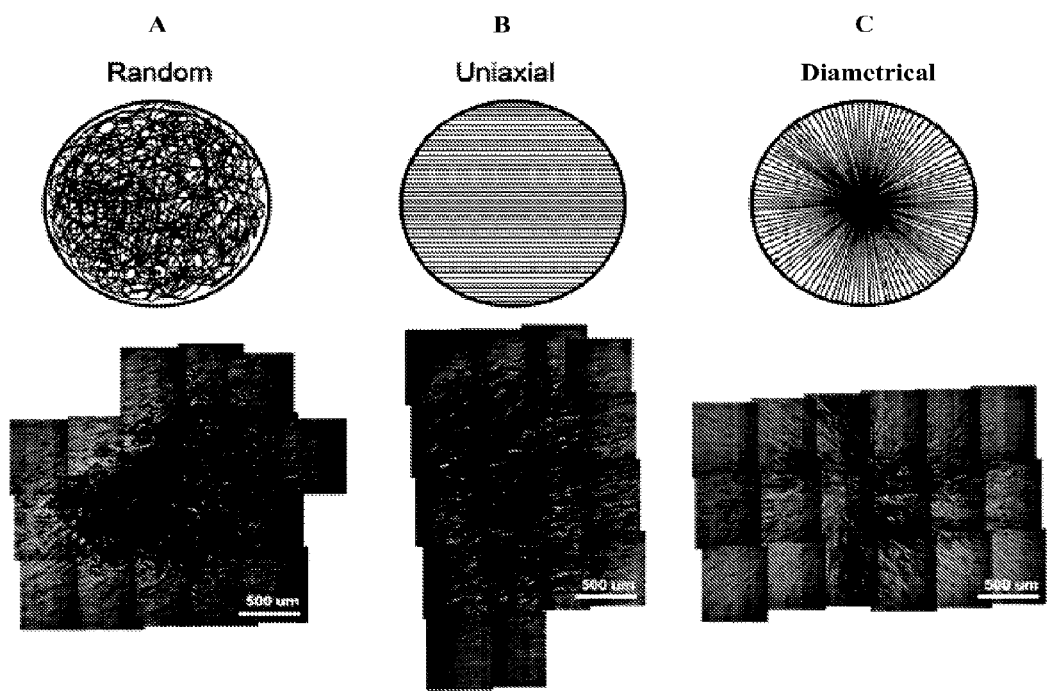
FIGS. 8A, 8B and 8C depict fluorescent microscopy images of cellular migration and wound coverage of mesenchymal stem cells on nanofiber membranes in an in vitro wound healing experiment performed pursuant to Example 11. Cells were seeded onto membranes having different types of nanofiber alignment (8A: random, 8B: uniaxial, 8C: diametrical) and were allowed to migrate into an induced gap defect. Fluorescent staining of the cellular cytoskeleton shows enhanced wound coverage on membranes with diametrically patterned fibers.

FIG. 8 depicts the cellular wound coverage on the various nanofiber membranes. On randomly oriented nanofibers, the MSC population showed a correspondingly random orientation and the wound coverage after 7 days was distinctly incomplete with very few cells reaching the center of the wound. The uniaxially aligned fibers induced corresponding uniaxial alignment of the cells and the wound coverage was much greater. However, the elongated shape of the wound on day 7 indicates that cell migration was much faster along the axis of fiber alignment than perpendicular to that axis. On the diametrically patterned fibers, the cells oriented toward the center of the wound at all points around the periphery, and migration was subsequently enhanced toward the center from all directions. Wound coverage on the diametrical fibers was nearly complete after 7 days with only a few small areas remaining uncovered.

Example 12

Tensile Testing of a Multilayer Fibrous Scaffold Having a First Layer of Diametrically Patterned Fibers and a Second Layer of Unaligned Fibers Made Using Poly(L-Lactide-Co-Caprolactone) with Poly(Propylene Glycol)

To investigate the mechanical properties of nanofibrous membranes with various fiber orientation, nanofiber membranes were produced as described herein. One set of samples was produced having a first layer of diametrically patterned fibers and a second layer of randomly oriented fibers. Another set of samples was produced having a first layer of uniaxially aligned fibers and a second layer of randomly aligned fibers.

Figure 9:
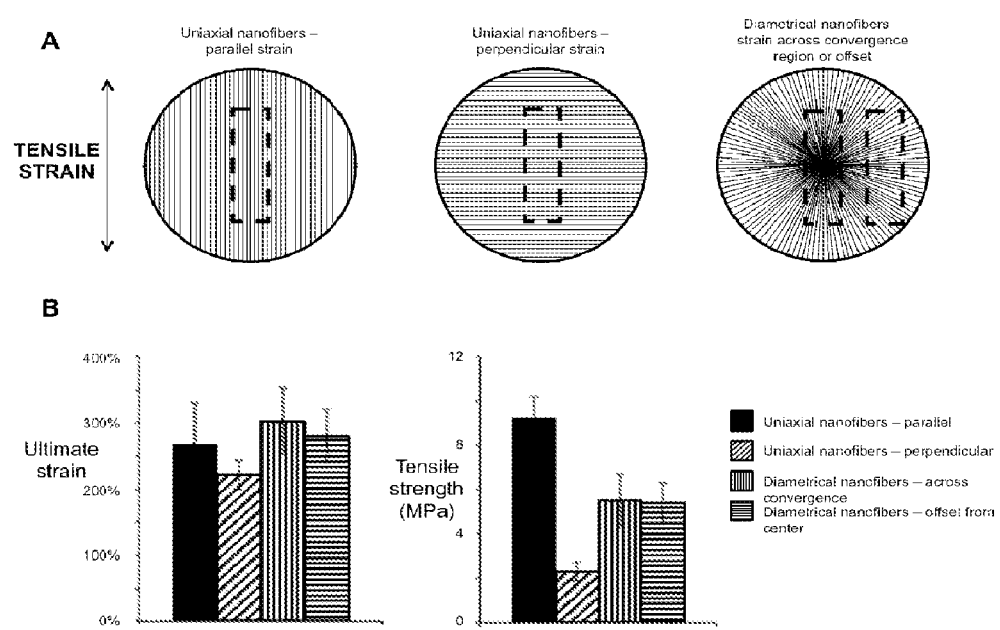
FIG. 9A depicts test samples used for mechanical testing of nanofiber membranes with varying degrees of alignment according to Example 12 of the present disclosure.
FIG. 9B depicts the mechanical properties of the nanofiber membrane test samples shown in FIG. 9A as determined by tensile testing according to Example 12 of the present disclosure.

Samples were subjected to uniaxial load using a Chatillon TCD225 Series Digital Force Tester equipped with a 100 N load cell and a pair of Universal Wedge Grips (GF-9 series, rated to 2.5 kN) (Ametek, Inc., Paoli, Pa.). Each sample was cut to 6×1 cm and fully wetted in Sorensen's buffer (pH 7.4) prior to loading in order to better simulate physiological conditions. Due to their inherent structural anisotropy, the nanofibrous samples were cut and tested under various orientations as depicted by the dashed lines in FIG. 9A. Samples with a first layer of uniaxially aligned fibers were tested with the tensile load oriented either parallel or perpendicular to the primary axis of fiber alignment. Samples with a first layer of diametrically patterned fibers were tested with tensile load either oriented directly across the convergence region of the membrane or offset 2 cm from the convergence region as depicted in FIG. 9A. Ultimate tensile stress and strain were calculated from the load-at-failure, elongation and cross sectional area measurements.

Mechanical test results in FIG. 9B indicate no significant difference in ultimate sample elongation for the various test conditions. However, tensile strength data show that samples with uniaxially aligned fibers were much stronger along the axis of alignment than perpendicular to that axis, which corresponds to the anisotropic nature of the fiber architecture. Conversely, the tensile strength of the samples with diametrically patterned fibers was roughly intermediate between the strengths either parallel or perpendicular to the uniaxial fibers. Additionally, the tensile strength for the diametrically patterned samples was approximately the same when the sample was tested across the convergence region of the diametrical fibers or offset from the convergence region. These results demonstrate that the mechanical properties of the nanofibrous membranes depend on the fiber orientation and architecture, and that these properties can be specifically tailored by controlling the electrospinning process.

While illustrative embodiments of the disclosure are disclosed herein, it will be appreciated that numerous modifications and other embodiments may be devised by those skilled in the art. For example, the features for the various embodiments can be used in other embodiments. Therefore, it will be understood that the appended claims are intended to cover all such modifications and embodiments that come within the spirit and scope of the present disclosure.

What is claimed is:

1. A fibrous polymer scaffold, comprising a first layer and second layer of polymer fibers wherein the fibers of the first layer are diametrically patterned and the fibers of the second layer are randomly or uniaxially oriented.

2. The fibrous polymer scaffold of claim 1, wherein at least one polymer fiber in the first layer and at least one polymer fiber in the second layer is the same polymer fiber that is continuous between the layers.

3. The fibrous polymer scaffold of claim 1, wherein the polymer fibers of the first layer comprise a material selected from: an aliphatic polyester, a poly(alkylene) oxide, poly(L-lactic acid), 70/30 L-lactide/e-caprolactone co-polymer, poly(caprolactone), poly(DL-lactide-co-caprolactone), poly(D-lactide-co-caprolactone), poly(L-lactide-co-caprolactone), poly(lactide-co-glycolic acid), poly(vinylpyrrolidine), poly(dimethylsiloxane), poly(lysine), collagen, laminin, fibronectin, elastin, alginate, fibrin, hyaluronic acid, proteoglycans, polypeptides, polysaccharides, silk fibroin, poly(ethylene-co-vinyl) alcohol, poly(vinyl) alcohol, poly(ethylene)glycol, poly(propylene)glycol, poly-L-lactide-co-glycolide-co-ε-caprolactone, poly(tetrafluoroethylene), poly(dioxanone), polyglactin 910, poly(urethanes), poly(ester urethane), poly(ether urethane), poly(trimethylene carbonate), poly(glycerol sebacate), poly(pyrrole), poly(acetylene), poly(hydroxyalkanoates), and copolymers and combinations thereof.

4. The fibrous polymer scaffold of claim 1, wherein the scaffold is a membrane.

5. The fibrous polymer scaffold of claim 1, further comprising an additive selected from poly(propylene glycol), poly(ethylene oxide), triethyl citrate, glycerol, poly(ethylene glycol), and combinations thereof.

6. The fibrous polymer scaffold of claim 5, wherein the additive is poly(propylene glycol).

7. The fibrous polymer scaffold of claim 1, further comprising a salt selected from NaCl, $KH_2PO_4$, $K_2HPO_4$, $KIO_3$, KCl, $MgSO_4$, $MgCl_2$, $NaHCO_3$, $CaCl_2$, sodium acetate, salt of acetic acid, salt of ascorbic acid, salt of citric acid, salt of lactic acid, salt of glycolic acid, and combinations thereof.

8. The fibrous polymer scaffold of claim 7, wherein the salt is sodium acetate.

9. The fibrous polymer scaffold of claim 1, wherein the polymer fibers comprise poly(L-lactide-co-caprolactone), poly(propylene glycol) and sodium acetate.

10. The fibrous polymer scaffold of claim 1, further comprising a cell.

11. The fibrous polymer scaffold of claim 1, further comprising a biomolecule.

12. A method of treating an injury or enhancing tissue growth in a subject, comprising: applying a fibrous polymer scaffold comprising a first layer of diametrically patterned polymer fibers such that:
   (i) the first layer contacts a defect in a tissue of the subject; and
   (ii) a convergence region of the first layer is placed in contact with the center of the defect.

13. The method of claim 12, wherein the injury comprises a defect in a tissue selected from abdominal wall, amniotic sac, bladder, blood vessels, brain, cardiac tissue, fascia, gingival tissue, intestine, ligaments, meningeal tissue, mucous membranes, muscle, nerves, skin, spinal cord, stomach and tendons.

14. A kit for the repair of wounds, surgical incisions or biopsies comprising:
   (i) a fibrous polymer scaffold comprising a first layer of diametrically patterned polymer fibers; and
   (ii) instructions for using the scaffold to repair wounds, surgical incisions or biopsies by promoting the regeneration of at least one anatomical biological component selected from abdominal wall, amniotic sac, bladder, blood vessels, brain, cardiac tissue, fascia, gingival tissue, intestine, ligaments, meningeal tissue, mucous membranes, muscle, nerves, skin, spinal cord, stomach and tendons.

* * * * *